US012605167B2

(12) United States Patent

Schers et al.

(10) Patent No.: US 12,605,167 B2

(45) Date of Patent: Apr. 21, 2026

(54) SURGICAL SYSTEM FOR CUTTING AN ANATOMICAL STRUCTURE ACCORDING TO AT LEAST ONE TARGET PLANE

(71) Applicant: DePuy Ireland Unlimited Company, Ringaskiddy (IE)

(72) Inventors: Jonathan Schers, Gieres (FR); Daniel Girardeau-Montaut, Gieres (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 1051 days.

(21) Appl. No.: 17/053,067

(22) PCT Filed: Apr. 25, 2019

(86) PCT No.: PCT/EP2019/060674

§ 371 (c)(1),
(2) Date: Nov. 4, 2020

(87) PCT Pub. No.: WO2019/219348

PCT Pub. Date: Nov. 21, 2019

(65) Prior Publication Data

US 2021/0068845 A1      Mar. 11, 2021

(30) Foreign Application Priority Data

May 14, 2018   (EP) .................................... 18305590

(51) Int. Cl.
*G06F 17/00* (2019.01)
*A61B 17/14* (2006.01)
(Continued)

(52) U.S. Cl.
CPC .......... *A61B 17/154* (2013.01); *A61B 17/142* (2016.11); *A61B 34/20* (2016.02);
(Continued)

(58) Field of Classification Search
CPC ..... A61B 17/154; A61B 17/142; A61B 34/20; A61B 34/30; A61B 34/70; A61B 90/50;
(Continued)

(56) References Cited

U.S. PATENT DOCUMENTS 10,368,878 B2 * 8/2019 Lavallee ................ A61B 34/70
10,441,294 B2 * 10/2019 Lavallee ................ B25J 9/0009
(Continued)

FOREIGN PATENT DOCUMENTS

CA        2953335 C  *  1/2021 ............. G06F 18/00
CN        102778848 A    11/2012
(Continued)

OTHER PUBLICATIONS

Robotic-assisted revision total knee arthroplasty: a novel surgical technique (Year: 2023).*

(Continued)

*Primary Examiner* — Ronnie M Mancho

(74) *Attorney, Agent, or Firm* — Condo Roccia Koptiw LLP

(57) ABSTRACT

A surgical system for cutting an anatomical structure (F, T) of a patient according to at least one target plane defined in a coordinate system of the anatomical structure comprises: (i) a robotic device (100) comprising: —an end effector comprising a cutting tool or a cutting block, —an actuation unit (4) comprising from three to five motorized degrees of freedom, attached to the end effector, configured for adjusting a position and orientation of the cutting tool or cutting block relative to each target plane, (ii) a passive articulated lockable holding arm (5) supporting the actuation unit (4); (iii) a tracking unit (200) configured to determine in real time the pose of the cutting plane with respect to the coordinate system of the anatomical structure, the tracking unit comprising a tracker configured to be rigidly attached to (Continued)

the actuation unit and a tracker configured to be rigidly attached to the end effector; (iv) a control unit (300) configured to determine the pose of the cutting plane with respect to the target plane and to control the actuation unit so as to bring the cutting plane into alignment with the target plane.

24 Claims, 33 Drawing Sheets

(51) Int. Cl.

| | |
|---|---|
| *A61B 17/15* | (2006.01) |
| *A61B 34/00* | (2016.01) |
| *A61B 34/20* | (2016.01) |
| *A61B 34/30* | (2016.01) |
| *A61B 17/00* | (2006.01) |
| *A61B 34/10* | (2016.01) |
| *A61B 90/50* | (2016.01) |

(52) U.S. Cl.
CPC .............. *A61B 34/30* (2016.02); *A61B 34/70* (2016.02); *A61B 2017/00115* (2013.01); *A61B 2017/00123* (2013.01); *A61B 2034/104* (2016.02); *A61B 2034/2055* (2016.02); *A61B 2034/2074* (2016.02); *A61B 2034/304* (2016.02); *A61B 90/50* (2016.02)

(58) Field of Classification Search
CPC ........... A61B 2017/00115; A61B 2017/00123; A61B 2034/104; A61B 2034/2055; A61B 2034/2074; A61B 2034/304; A61B 17/14; A61B 2034/2059; A61B 2090/508; A61B 34/25; A61B 90/11; A61B 90/39; A61B 17/1675; A61B 17/02
USPC ........................................................ 700/245
See application file for complete search history.

(56) References Cited

U.S. PATENT DOCUMENTS

| | | | |
|---|---|---|---|
| 11,607,229 B2 * | 3/2023 | Lavallee | A61F 2/38 |
| 2007/0137372 A1 * | 6/2007 | Devengenzo | G16H 40/67 |
| | | | 74/490.01 |
| 2010/0331855 A1 | 12/2010 | Zhao et al. | |
| 2011/0130761 A1 | 6/2011 | Plaskos et al. | |
| 2011/0295109 A1 | 12/2011 | Lavallee et al. | |
| 2013/0172906 A1 | 7/2013 | Olson et al. | |
| 2014/0088410 A1 | 3/2014 | Wu | |
| 2016/0135816 A1 * | 5/2016 | Lavallee | B25J 9/0009 |
| | | | 606/88 |
| 2016/0242858 A1 | 8/2016 | Moctezuma De La Barrera et al. | |
| 2016/0354162 A1 | 12/2016 | Yen et al. | |
| 2020/0073358 A1 * | 3/2020 | Dedkov | G06T 7/74 |
| 2021/0353311 A1 * | 11/2021 | Lavallee | A61B 34/20 |
| 2021/0361295 A1 * | 11/2021 | Lavallee | A61B 34/20 |
| 2024/0293130 A1 * | 9/2024 | Lavallee | A61B 17/02 |

FOREIGN PATENT DOCUMENTS

| | | | | | |
|---|---|---|---|---|---|
| CN | 105431102 A | 3/2016 | | | |
| CN | 110076774 A | 8/2019 | | | |
| JP | 2015-534480 A | 12/2015 | | | |
| JP | 2018-506352 A | 3/2018 | | | |
| WO | WO 2007-045810 A2 | 4/2007 | | | |
| WO | WO 2007-136768 A2 | 11/2007 | | | |
| WO | WO-2007149183 A2 * | 12/2007 | ........... | B25J 9/1697 |
| WO | WO 2012-131658 A1 | 10/2012 | | | |
| WO | WO 2014-139023 A1 | 9/2014 | | | |
| WO | 2014-198784 A1 | 12/2014 | | | |
| WO | 2016/109886 A1 | 7/2016 | | | |
| WO | WO 2016-126914 A1 | 8/2016 | | | |
| WO | WO 2017-206920 A1 | 12/2017 | | | |
| WO | 2018-112025 A1 | 6/2018 | | | |

OTHER PUBLICATIONS

Robot-Assisted Total Knee Arthroplasty: (Year: 1986).*
Robot-Assisted Total Knee Arthroplasty Investigation of the Feasibility and Accuracy of the Robotic Process (Year: 1986).*

\* cited by examiner

SURGICAL SYSTEM FOR CUTTING AN ANATOMICAL STRUCTURE ACCORDING TO AT LEAST ONE TARGET PLANE

CROSS REFERENCE TO RELATED APPLICATIONS

This application is a national stage application of International Application No. PCT/EP2019/060674, filed on Apr. 25, 2019. International Application No. PCT/EP2019/060674 claims priority to and the benefit of European Application No. 18305590.4, filed May 14, 2018. The entire contents of each of these applications are incorporated herein by reference.

TECHNICAL FIELD

The disclosure relates to a robotic system for cutting an anatomical structure of a patient according to at least one target plane.

BACKGROUND

Total knee arthroplasty typically requires cutting both the femoral epiphysis and tibial epiphysis in order to remove the damaged bone and cartilage and install a knee prosthesis.

To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has to be made on the tibia T along plane T1.

In order for the surgeon to carry out all these planes accurately and in a reduced time, computer assisted systems have been developed.

For example, document WO 2014/198784 teaches a surgical system comprising a handheld device that includes:
    a base designed to be held in a user's hand,
    an end-effector for mounting a burr intended to mill a planned volume of a part of a patient's body,
    an actuation unit connected to said base and said end-effector for moving the burr with respect to the base in order to treat said planned volume,
    a support unit connected to the base or to the end-effector which provides a partial mechanical link between the base or the end-effector and the part to be treated.
The system also comprises a tracking unit which is configured to determine in real time the pose of at least one of the burr, the end-effector and the base with respect to the part to be treated.
    A control unit of the system is configured to:
    (a) compute in real time an optimized path of the burr or of the end-effector with respect to the base depending on said measured pose,
    (b) detect whether said computed path of the burr or of the end-effector can be achieved without changing the pose of the base, and, if this is not the case, determine a possible repositioning of the base with respect to the part to be treated,
    (c) configure the actuation unit so as to move the end-effector according to said computed path, and (d) iterate steps (a) to (c) until the planned volume has been treated.
    A user interface is used to indicate feedback information to the user.

However, even if the robot described in this document is very efficient for milling a body part, the design with an actuation unit in the form of a planar five-bar linkage as illustrated in document WO 2014/198784 is not optimal for cutting a body part with a saw. Indeed, the degrees of freedom provided by the actuation unit are not suited to the plurality of cutting planes to achieve in knee arthroplasty using a saw mechanism coincident with each plane to be cut.

Document US 2011/0130761 teaches a robotic system dedicated to guiding a saw in order to carry out several cuts on a femur in total knee arthroplasty. The system comprises a navigation system that locates in position and orientation trackers attached to the bone and instruments.

The system comprises a seat rigidly attached to the femur by at least one pin.

An adjustment system comprising two screws is attached to the seat via a ball and socket joint.

The cutting block, which comprises a slot intended to guide a saw blade within a cutting plane, is attached to an arm that supports two motors.

The arm is pivotally mounted on the adjustment system, the orientation of the arm relative to the seat being adjustable by the two screws of the adjustment system.

The arm is rotatable relative to the seat about a first rotation axis by a first motor, the cutting block is rotatable relative to the arm relative to a second rotation axis by the second motor, both rotation axes being parallel to each other.

In use, the seat is rigidly fixed to the femur by the at least one pin, then the position of the first and second rotation axes is modified by the adjustment device which is operated manually by the surgeon, with visual feedback from the navigation system.

Once a suitable position has been found, the trackers attached to the cutting block are removed and the cutting block is no longer navigated.

Then, the motors are operated to move the cutting block about two rotational axes. The surgeon then cuts the bone along each desired cutting plane using a saw received in the cutting block. Thus, the system is not able to detect or compensate in real time a potential misalignment of the cutting block slot relative to the target planes.

A major drawback of such a system is that the rigid fixation of the seat to the femur is quite invasive since it requires implanting large pins into the bone to bear the weight of the robot and compensate for forces exerted during sawing by the saw inserted in the cutting block carried by the robot. Large pins used to carry an important weight and react to important strengths can potentially generate bone fracture. In addition, weight and strengths can lead to motion of the pins in the bone, which will impact significantly the accuracy of the system.

Besides, the rotational axes have to be adjusted very precisely in order to achieve all the target planes. However, this adjustment is difficult and prone to errors or inaccuracy because it is done manually and is only assisted by a visual feedback provided by the navigation system. If the cutting plane slightly moves during sawing because of forces exerted by the user or saw, it would be very difficult for the user to detect it and to correct those adjustments manually.

Moreover, if the pins are not placed in a correct location because of surgical constraints, anatomical constraints, or misuse, the robot will not be able to position the cutting block so that all the cuts can be reached and it will be necessary to reposition the pins in the bone at a slightly different location, which is difficult.

In addition, this system does not allow to carry out the tibial cut while the seat is fixed to the femur, and therefore another specific device is necessary to perform cuts on the tibia, which takes additional time, additional pins, additional systems and efforts.

SUMMARY

The disclosed embodiments provide a surgical system intended to guide a cutting tool to cut an anatomical bony structure of a patient according to at least one target plane, which does not require any invasive attachment to the patient's bone while controlling precisely the position and orientation of a cutting tool to reach the target plane.

Accordingly, the surgical system comprises:

(i) a robotic device comprising:

an end effector comprising a cutting tool or a cutting block, an actuation unit comprising from three to five motorized degrees of freedom, attached to the end effector, configured for adjusting a position and orientation of the cutting tool or cutting block relative to each target plane, (ii) a passive articulated lockable holding arm supporting the actuation unit;

(iii) a tracking unit configured to determine in real time the pose of the cutting plane with respect to the coordinate system of the anatomical structure, the tracking unit comprising a tracker configured to be rigidly attached to the actuation unit and a tracker configured to be rigidly attached to the end effector;

(iv) a control unit configured to determine the pose of the cutting plane with respect to the target plane and to control the actuation unit so as to bring the cutting plane into alignment with the target plane, wherein the control unit is configured to implement a control loop comprising the following steps:

(S1) determining poses of the actuation unit, the end effector and the anatomical structure using localization information provided by the tracking unit;

(S2) computing a deviation between the cutting plane and the target plane;

if the deviation is less than a threshold, allowing operation of the cutting tool and returning to step (S1) to determine a new pose of the actuation unit, end effector and anatomical structure;

if the deviation is greater than or equal to the threshold, projecting (i.e. expressing) (S3) the cutting plane and the target plane in the coordinate system of the actuation unit, (S4) computing a correction matrix between a plane attached to an output of the actuation unit and the cutting plane;

(S5) updating the target plane with the correction matrix computed in step (S4);

(S6) computing a new attitude of the actuation unit to align the cutting plane with the updated target plane, and determining the movements to be applied by the motors of the actuation unit;

activating the actuation unit to apply said movements.

By "holding arm" is meant an articulated arm made of at least two segments and that can be locked in a given position. The holding arm is attached to a stable structure of the operating room, such as an operating table, a leg holder, or a mobile cart with blocked wheels.

By "actuation unit" is meant a series of rigid segments linked together by motorized degrees of freedom. The actuation unit is rigidly attached to the extremity of the holding arm. The actuation unit is controlled by a control unit.

By "planar mechanism" is meant a mechanism that constrains an object to move only inside a plane, with at least two degrees of freedom. For example, a planar mechanism can be made of two degrees of translation and one degree of rotation.

By "cutting tool" is meant a saw, a burr, a laser, or a high-pressure water jet, that are able to perform cuts in a bone. For knee surgery, the cutting tool is generally made of a power unit that carries and activates an oscillating saw blade.

By "anatomical structure" is meant in the present text a substantially rigid structure, such as a bone or cartilage, or a joint formed of two or more bones.

By "pose" is meant, in the present text, the 3D position and 3D orientation of a tool in up to six degrees of freedom. It is to be noted that depending on the application, a "pose" may not be necessary determined by all six degrees of freedom but only by one degree of freedom or a subset comprising less than six degrees of freedom.

By "alignment" of the cutting plane with a target plane, is meant in the present text that said cutting plane deviates from the target plane by a distance of less than 1 mm and an angle of less than 1°. Preferably, the cutting plane coincides perfectly with the target plane. To measure such a distance, a selected point of the target plane is projected onto the cutting plane, and the distance between the projected point and the target plane is measured. The selected point shall be in the vicinity of the anatomical structure to be cut. For example, the selected point may be an anatomical point of the anatomical structure, or the center of the anatomical structure to be cut, projected on the target plane.

According to an embodiment, the tracking unit is an optical tracking unit comprising a camera and optical trackers detectable by the camera.

The camera is advantageously configured to operate at a frequency at least twice greater than the frequency at which the control unit is configured to implement each iteration of the control loop (e.g. each sequence of steps (S1) to (S6)).

According to an embodiment, the camera is configured to operate at a frequency greater than 200 Hz, preferably greater than 300 Hz.

According to an embodiment, the control unit is configured to implement each iteration of the control loop at a frequency greater than 50 Hz, preferably greater than 100 Hz.

According to an embodiment, the control unit is configured to implement the control loop including an additional step comprising, between steps (S1) and (S2), assessing whether a current pose of the actuation unit can be computed based on the localization information provided by the tracking unit.

Advantageously, the control unit may be further configured to implement the control loop including an additional step comprising storing the current pose of the actuation unit in a memory of the control unit and implementing step (S2) with said current pose of the actuation unit if said current pose can be determined.

The control unit may be further configured to implement the control loop including, if the current pose of the actuation unit cannot be determined, an additional step of assessing whether a previous pose of the actuation unit is stored in the memory of the control unit.

According to an embodiment, the control unit is further configured to implement the control loop including, if said previous pose of the actuation unit is stored in the memory of the control unit, using said previous pose to implement step (S2).

The control unit may also be configured to implement the control loop including, if no previous pose is stored in the memory of the control unit, implementing again step (S1).

According to an embodiment, the control unit is configured to implement the control loop including, between steps (S4) and (S5), computing a norm of the correction matrix and comparing said norm with a determined threshold.

Advantageously, the control unit is configured to implement the control loop including, if the norm is smaller than the threshold, implementing step (S5) using said correction matrix.

The control unit may be further configured to stop the actuation unit if the norm is greater than the threshold.

According to an embodiment, the control unit is configured to determine whether the pose of the actuation unit used in steps (S2) to (S4) is a previously stored pose, and:

if said pose is a previously stored pose, erase said previously stored pose from the memory and return to step (S1);

if said pose is the current pose of the actuation unit, output an error.

According to an embodiment, the robotic device comprises a light emitter configured to be activated by the control unit to emit light when the norm of the correction matrix is greater than the threshold.

According to an embodiment, the control unit is configured to output a message to a user to check that the tracker of the actuation unit is in a field of view of the camera.

According to an embodiment, the surgical system comprises:

(i) a robotic device comprising:

an end effector comprising a cutting tool or a cutting block, an actuation unit comprising from three to five motorized degrees of freedom, attached to the end effector, configured for adjusting a position and orientation of the cutting tool or cutting block relative to each target plane, (ii) a passive articulated lockable holding arm supporting the actuation unit;

(iii) a tracking unit configured to determine in real time the pose of the cutting plane with respect to the coordinate system of the anatomical structure, the tracking unit comprising a tracker configured to be rigidly attached to the actuation unit and a tracker configured to be rigidly attached to the end effector;

(iv) a control unit configured to determine the pose of the cutting plane with respect to the target plane and to control the actuation unit so as to bring the cutting plane into alignment with the target plane, wherein the control unit is configured to implement a control loop comprising the following steps:

computing a deviation between the cutting plane and the target plane based on relative poses of the actuation unit, the end effector and the anatomical structure provided by the tracking unit;

allowing operation of the cutting tool if the deviation is less than a threshold;

computing a correction matrix between a plane attached to an output of the actuation unit and the cutting plane if the deviation is greater than the threshold;

updating the target plane with the computed correction matrix;

computing a new attitude of the actuation unit to align the cutting plane with the updated target plane.

Advantageously, in the case of knee arthroplasty, the implementation of all the tibial and femoral cuts can be made with the patient's leg in the same position and without substantially moving the system.

BRIEF DESCRIPTION OF THE DRAWINGS

Other features, embodiments and advantages of the exemplary embodiments will be apparent from the detailed description that follows, based on the appended drawings wherein.

DETAILED DESCRIPTION

The following description is focused on knee surgery, in particular total knee arthroplasty (TKA), in which case the anatomical structure to be cut is a joint formed of the femur and the tibia.

However, the invention is not limited to this specific application, but can be applied to various applications. In general, the embodiments can be used in any surgical intervention requiring at least one osteotomy step. In particular but not limited to, the concepts could also be implemented in the following surgical applications: unicompartmental knee arthroplasty (UKA), tibial or femoral osteotomy, patella resurfacing, hallux valgus surgery, hip surgery for cutting the proximal femur, shoulder surgery for cutting the humeral head, spine surgery for correcting deformities and performing an osteotomy of the vertebral body, ankle surgery, maxillofacial surgery.

As will be explained in further detail below, the device is used in a context in which at least one target plane along which the anatomical structure has to be cut is planned before performing the cut(s).

Planning of at least one target plane is performed using patient's pre-operative images (e.g. CT, MRI, Ultrasound images, 2D or 3D X-rays in combination with statistical shape models, PET, etc.) or intra-operative 3D data (e.g. intra-operative CT or CBCT, intra-operative MRI, Ultrasound images, 2D or 3D intra-operative X-ray images, geometric data provided by localizing systems and providing 3D points, clouds of 3D points, surfaces reconstructed from clouds of 3D points, etc.), or both.

Multiple computer-assisted surgery methods exist to register the target plane with a coordinate system attached to the anatomical structure to be cut, using images or geometric patient data collected during surgery.

Typically, intra-operative images or data are used to register pre-operative images in a unique coordinate system attached to the anatomical structure, and usually represented by a tracker that can use any of computer assisted surgery technologies (optical tracker made of reflective markers, optical tracker made of active LEDs, electromagnetic trackers made of coils, combination of inertial sensors, ultrasonic sensors, RFID sensors, etc.).

Using any of these conventional computer-assisted surgery methods results in that the target planes have a known geometric representation in a coordinate system attached to the anatomical structure to be cut, and whose movements are tracked in real-time by a tracking unit as it will be detailed below. Typically, the surgical planning step for total knee surgery results in five target planes defined in a coordinate system attached to a tracker fixed to the femur and one target plane defined in a coordinate system attached to a tracker fixed to the tibia.

Figure 1:
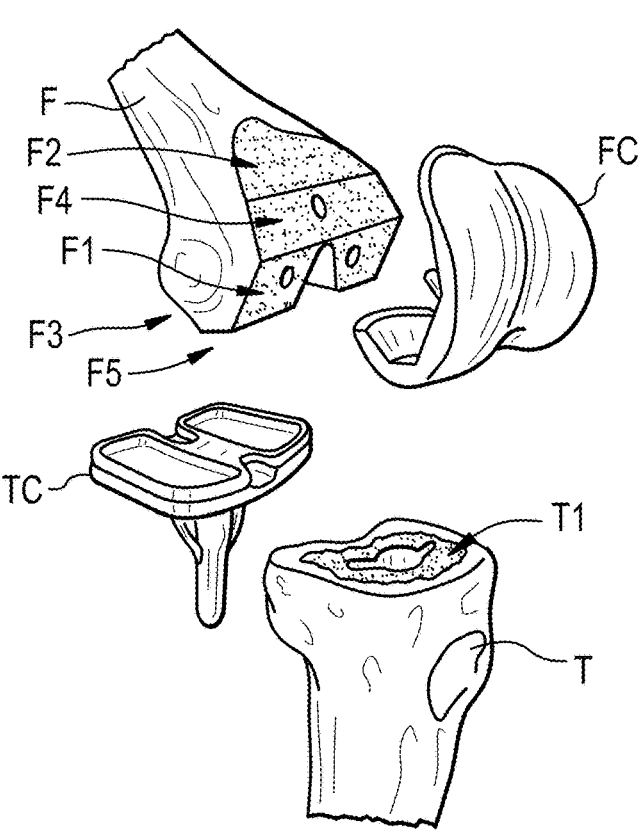
FIG. 1 schematically illustrates the cuts to be made into a femur and a tibia in order to implant a knee prosthesis.
Figure 2:
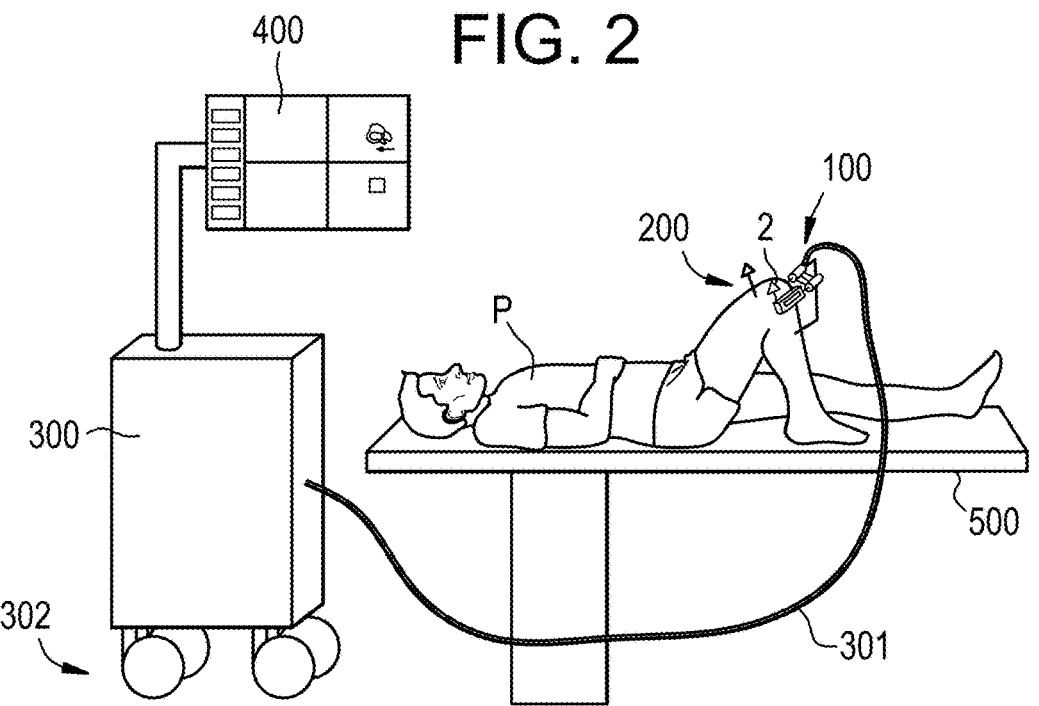
FIG. 2 shows an overview of a surgical system according to the disclosure.

FIG. 2 shows an overview of a surgical system.

A patient P is lying on an operating table 500, e.g. in view of total knee arthroplasty (TKA).

To that end, a cutting tool, such as a saw 2, which is intended to cut the tibial and femoral bones along at least one target plane—preferably, a plurality of target planes—is used by a user such as a surgeon.

According to an embodiment, the cutting tool is held by an end effector attached to the robotic device 100 and constrained in each target plane by an actuation unit 4 (not shown in FIG. 2, but better seen in subsequent drawings). Alternatively, a cutting block comprising at least one slot is held by the end effector and constrained in each target plane by an actuation unit, and the cutting tool is freely manipulated by the surgeon through the slot which defines a guiding plane.

The robotic device 100 is connected to a control unit 300 that controls the actuation unit.

Said control unit typically comprises power supply, AC/DC converters, motion controllers to power the motors of the actuation unit, fuses, real-time control system interface circuits.

The system also comprises a tracking unit 200, such that the relative pose of the robotic device, the end effector and the anatomical structure to be cut is tracked in real time and is shared between a real time control unit and a planning system.

At least one coordinate system is attached to the anatomical structure while at least one coordinate system is attached to the end effector and another one to the robotic device.

The tracking unit measures the relative motions between both coordinate systems in real time. Real time means high frequencies greater than twenty Hertz, preferably in the range of one hundred to five hundred Hertz, with low latency, ideally less than fifteen milliseconds.

The data obtained by the tracking unit are transferred to the control unit 300 via any suitable connection, with wires 301 or wireless, with low latency.

According to a preferred embodiment, the tracking unit is an optical tracking unit comprising a camera and optical trackers detectable by the camera.

The real-time control unit is able to carry out the proposed real-time control algorithms at a reasonably high frequency with low additional latency in order to compensate small relative movements between the anatomical structure and the robotic device.

Preferably, the camera is configured to operate at a frequency at least twice greater than the frequency at which the control unit is configured to implement the control algorithms.

According to a preferred embodiment, the camera is configured to operate at a frequency greater than 200 Hz, preferably greater than 300 Hz, e.g. 330 Hz. The control unit is configured to implement the control algorithms at a frequency greater than 50 Hz, preferably greater than or equal to 100 Hz.

For a surgical robotic device, and more generally for any system relying on one or several motors, different performance requirements must be defined in order to select the right motor type (e.g. motion speed, torque, positioning accuracy, etc.). Additional constraints or limitations may also be taken into account (dimensional capacity, available power supply, temperature, humidity, expected service life, etc.).

Since the robotic device is meant to perform real-time compensation of small movements, the velocity is one of the main criteria. During TKA surgery, the leg is held by the surgeon or an assistant, possibly with the help of wedges or pads (typically located below the foot and/or on the lateral side of the leg), and/or with a dedicated leg holder. Therefore, the amplitude of motion of the joint during the cuts is very limited. Typically, the femur knee center almost never moves of more than 3 centimeters. Besides, the robotic device is held by a holding arm and is thus not likely to move significantly during the cuts. However very small and fast displacements occur constantly (typically less than a few millimeters) due to vibrations for instance. Therefore, the motors are selected so as to be able to perform high accelerations in order for the robotic device to compensate for these small but fast movements almost in real time.

The motors of the robotic device are also able to support a potentially high load or forces applied on the end-effector. For instance, a robotic device configured for TKA may hold a surgical saw (whose weight is about 1.5 kg) and has to resist some normal forces applied by the user when handling the saw during the cut. These constraints define the minimum torque that must be supported/achieved by the motor in normal conditions.

In addition, especially for a compact robotic device, the size of the motors must remain limited. Hence, the skilled person selects suitable motors based on a compromise between high velocity, high torque and small footprint.

The real-time control unit computes in real time the position of the end effector with respect to a target plane depending on said measured pose.

In this figure, the connection is represented by a wire 301 but it may instead be wireless if the robotic device is battery-powered.

The control unit and tracking unit may be arranged in a cart 302 that can be moved in the operating room. They can be also mounted on separate carts, articulated holding arms, lighting systems, or the tracking unit can be also mounted directly on the anatomical structure or on some parts attached to the robotic device. For example, the end effector can rigidly support an electromagnetic emitter while electromagnetic sensors can be attached to the anatomical structure.

The system may also comprise a visual user interface 400 that is intended to display feedback information to a user and enable system configuration by the user. The feedback information may comprise:

indication(s) about a deviation (distance and/or angle) between the cutting plane and the target plane, before the anatomical structure is cut;

indication(s) about whether the target plane can be achieved with the current position of the robotic device;

directions to reposition the actuation unit with respect to the anatomical structure to be cut in order to allow the actuation unit to align the cutting plane with the target plane; and/or indication(s) about a deviation (distance and/or angle) between the cutting plane and the target plane, while the anatomical structure is being cut.

Said user interface 400 may advantageously comprise a screen, which may be located on a cart in the operating room, e.g. on the same cart 302 as the control unit and tracking unit, or on a separate cart, or attached to the walls or the celling of the operating room.

In addition to or instead of said screen, the user interface may comprise an indicator that is arranged on the robotic device itself to provide information to the user. Said indicator can be made of LEDs arranged to indicate arrows, numbers or letters, or a miniature display.

A surgical system wherein the control unit, tracking unit and/or user interface are embedded in the robotic device itself would still be within the scope of the invention, provided that the embedded units are powered by a sufficiently powerful power supply or battery and that their size and weight do not hinder the manipulation of the robotic device by the user. For example, micro cameras can be attached to the base of the actuation unit and markers can be attached to the anatomical structure and to the cutting tool.

According to an embodiment, the cutting tool is a surgical saw mounted on an end effector attached to the actuation unit. The saw 2 comprises a casing 23 and a saw blade 22 that oscillates in a determined plane (called "cutting plane") relative to the casing 23 (see in particular FIG. 3A). Thus, the saw blade can be operated to cut the anatomical structure according to a target plane without requiring any cutting block, provided that the actuation unit 4 constrains the saw in the target plane in real time. Usually, the cutting plane is parallel to the longitudinal axis of the casing and the saw blade oscillates on both sides of this axis; such a saw is known in the medical field as a "sagittal saw".

According to an embodiment, the end effector is connected to the output of the actuation unit by a planar mechanism. The casing is usually positioned relative to the planar mechanism so that the cutting plane is parallel to the plane of the planar mechanism.

In the absence of such a planar mechanism, it is considered that a virtual plane (called output plane in the following description) is attached to the output of the actuation unit.

According to an embodiment, the saw blade moves back and forth along the longitudinal axis of the casing; such a saw is known in the medical field as a «reciprocating saw». The casing is usually positioned relative to the planar mechanism so that the cutting plane is orthogonal to the plane of the planar mechanism.

According to an embodiment (see FIG. 25), the cutting tool is a burr 2'. Indeed, especially if the burr head is small (e.g. with a diameter of the order of three mm), the operation of the burr constrained in a cutting plane allows performing a planar cut. The burr tip can be spherical or cylindrical. Typically a cylindrical shape burr tip with a three mm diameter constrained by the planar mechanism to remain in a plane parallel to the cylinder axis will be rigid enough to make large cuts and small enough to perform fast cutting.

According to an embodiment (not illustrated), the cutting tool is a laser with a system to control the depth of penetration of the laser to avoid damaging soft tissues behind the bone.

According to another embodiment (not illustrated), the cutting tool can be a high-pressure water jet or any other device that creates cuts in an anatomical structure.

According to another embodiment, for cutting soft tissues, the cutting tool can be a scalpel or any electrically activated device such as a lancet.

In the drawings that are described below, the cutting tool is usually a saw, without any intended limitation of the invention.

The actuation unit advantageously comprises from three to five motorized degrees of freedom. The actuation unit is advantageously designed to be as light and compact as possible. In some embodiments, the actuation unit may comprise six degrees of freedom.

According to an embodiment, the actuation unit 4 has a serial architecture made of a plurality of mobile segments. The segments of the actuation unit are numbered 41, 42, 43 throughout the set of drawings. In some embodiments, the actuation unit has three motorized rotational degrees of freedom for adjusting the position and orientation of the cutting plane relative to each target plane. In other embodiments, the actuation unit has two motorized rotational degrees of freedom and one or two motorized translational degrees of freedom. Generally speaking, the actuation unit comprises from three to five motorized degrees of freedom, at least two of which being rotational degrees of freedom orthogonal to each other. In the present text, the term "axis" designates the geometric rotation or translation axis corresponding to said degree of freedom.

The segments and their components are integrated in an optimal way such that the robotic device remains as compact and light as possible while remaining strong enough to be able to hold the planar articulation and the cutting tool, as well as resisting to some normal pressure applied by the user when he/she manipulates the cutting tool.

In the present text, the axes and segments are numbered with increasing numbers starting from the base (i.e. the part of the robotic device that remains stationary while the robotic device works) and towards the cutting tool; this type of numbering is conventional for serial robotic architectures.

Preferably, the architecture of the actuation unit is made of three rotational degrees of freedom.

According to a preferred architecture, the segments are arranged such that the rotation axes of two adjacent segments (i.e. either the first and second axes or the second and third axes) are substantially parallel to each other, and the first axis is substantially orthogonal to the third axis. Preferably, the rotation axes of two adjacent segments are parallel to each other and the first axis is orthogonal to the third axis.

Figure 3A:
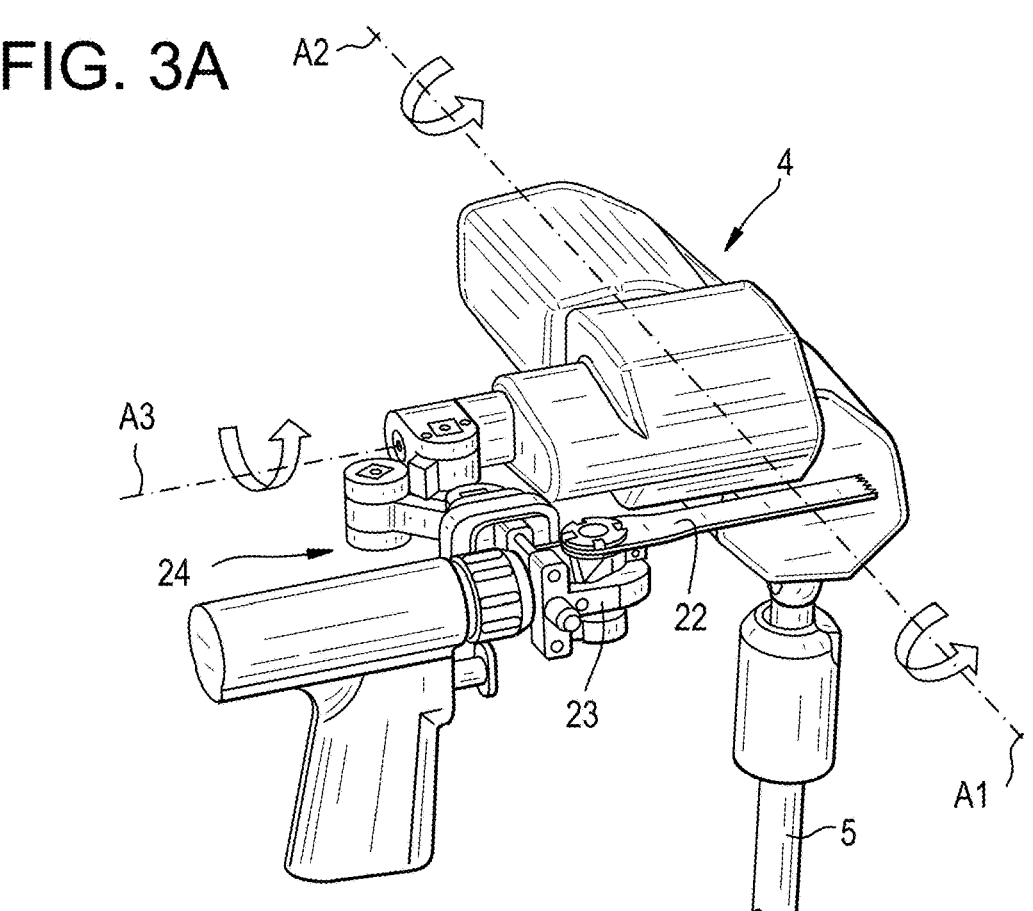
FIGS. 3A and 3B are perspective views of a robotic device according to a first embodiment.
Figure 3B:
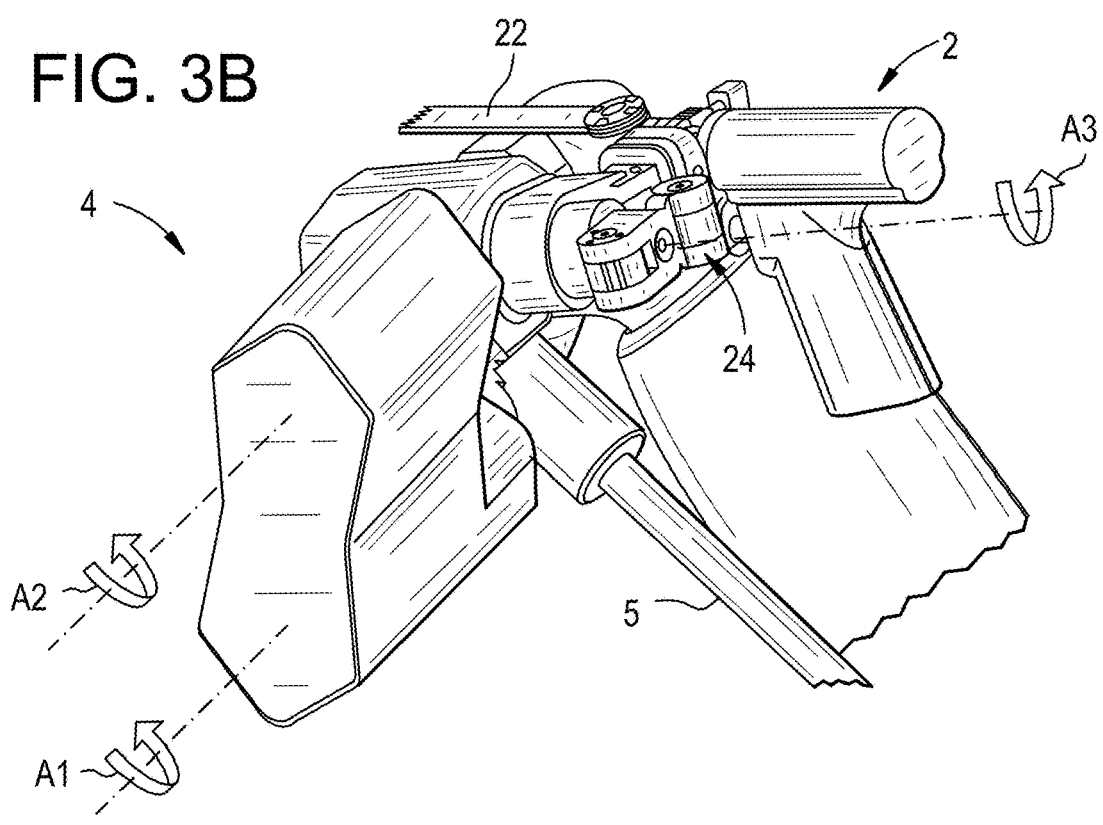

According to a preferred embodiment illustrated in FIGS. 3A-3B, the second axis A2 is parallel to the first axis A1 and the third axis A3 is orthogonal to the first and second axes. Advantageously, the distance between the first axis and the second axis is a fixed distance comprised between 80 and 100 mm. In such case, for application to TKA, the tibial cut and the femoral cuts can be made with a single initial position of the robotic device.

In use for knee arthroplasty (TKA, UKA, etc.), the robotic device may be placed on the medial (internal) or on the lateral (external) side of the leg of interest. The first rotation axis A1 is intended to be substantially orthogonal to the sagittal plane of the knee, and substantially located at the level of the medial or lateral epicondyle. For any application of the robotic device, it is possible to define some anatomical landmarks that are easy to identify and to use them for aligning the actuation unit in a ball park.

Figure 4:
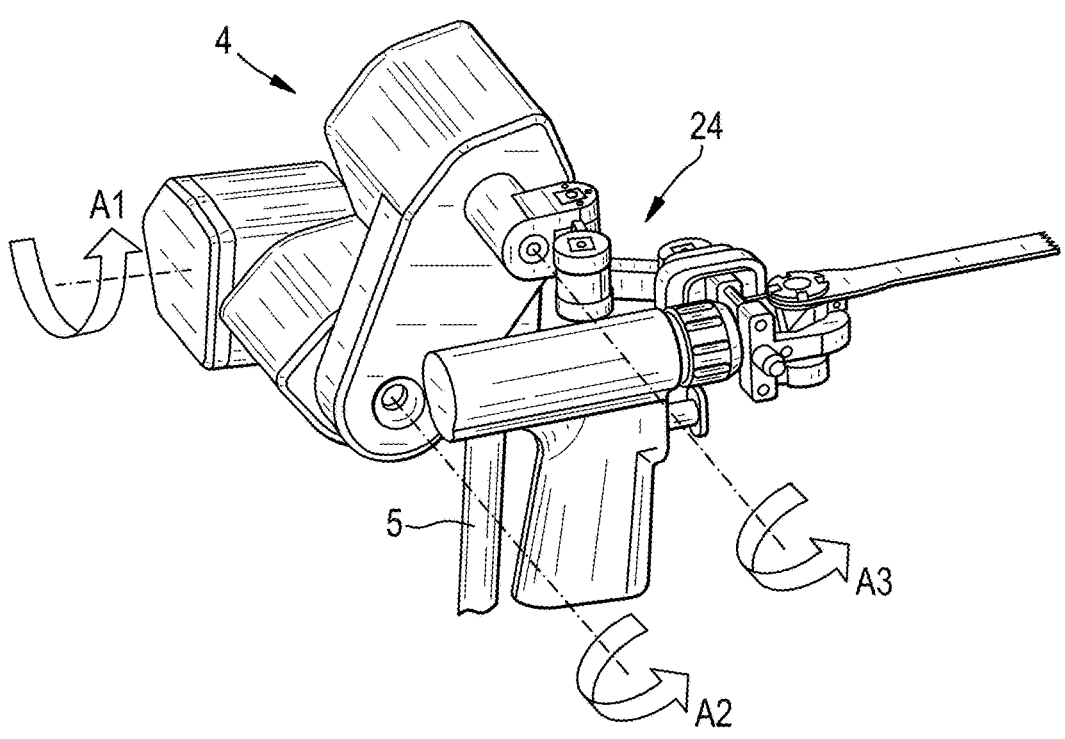
FIG. 4 is a perspective view of a robotic device according to a second embodiment.

According to an alternative embodiment illustrated in FIG. 4, the second axis A2 is substantially orthogonal to the first axis A1, and the third axis A3 is substantially parallel to the second axis. In a preferred implementation of this embodiment, the second axis A2 is orthogonal to the first axis A1, and the third axis A3 is parallel to the second axis.

In use, the first rotation axis is intended to be substantially parallel to the epicondylar axis of the knee, which is usually substantially parallel to the operating table and orthogonal to the leg axis.

Figure 5:
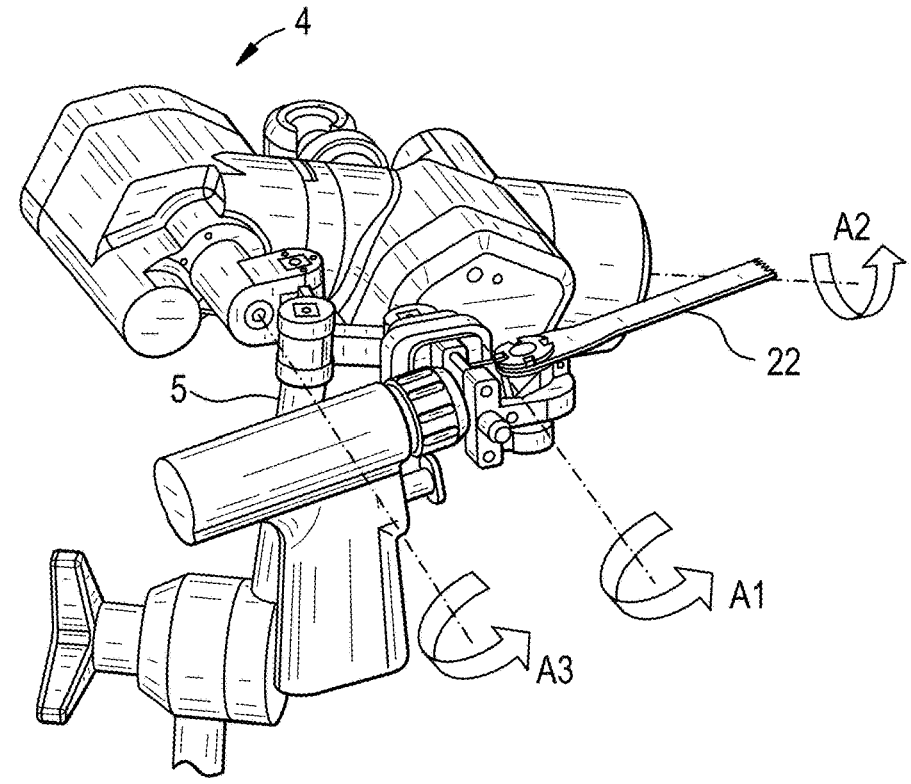
FIG. 5 is a perspective view of a robotic device according to a third embodiment.

According to another architecture illustrated in FIG. 5, the second axis A2 is substantially orthogonal to the first axis A1 and the third axis A3 is substantially orthogonal to the second axis A2. In a preferred implementation of this architecture, the second axis A2 is orthogonal to the first axis A1 and the third axis A3 is orthogonal to the second axis A2. The first axis A1 and third axis A3 are separated by a fixed distance.

As compared to the architecture of FIG. 5, the architecture of FIGS. 3A-3B has the following advantage: given the intended position of the first rotation axis relative to the knee, this architecture is well conditioned, meaning that small movements of the cutting plane can be achieved by small movements of the actuation unit for all intended target plane positions in the instance of knee arthroplasty procedure.

Advantageously, for application to knee arthroplasty (TKA, UKA, etc.), the dimension of the actuation unit is sufficient to enable performing all the femoral and tibial cuts without substantially moving the robotic device. In this respect, the architecture of FIG. 5 is preferred to the one of FIGS. 3A-3B and FIG. 4 since it provides a greater compacity of the actuation unit. In use, the architecture of FIG. 5 is still well conditioned for knee arthroplasty when the first axis is substantially aligned with the epicondylar axis of the femur.

Figure 6:
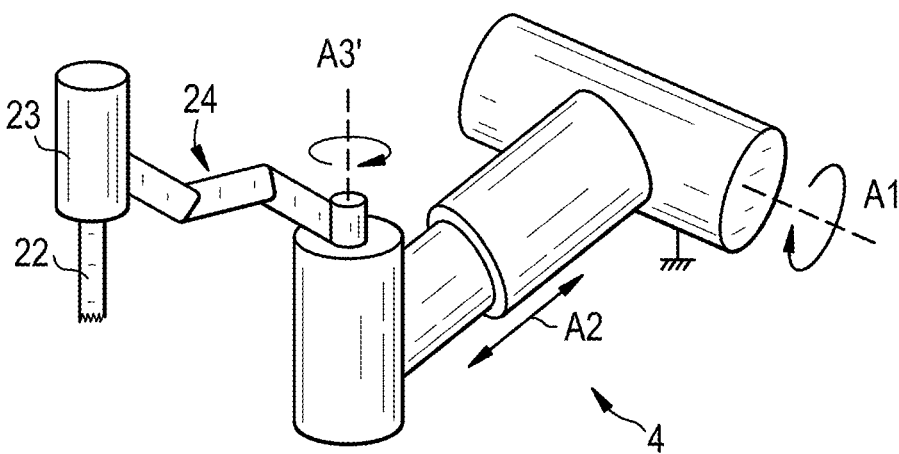
FIG. 6 is a schematic view of the architecture of the actuation unit according to a fourth embodiment.

According to an embodiment illustrated in FIG. 6, the actuation unit 4 comprises two motorized rotational degrees of freedom and one motorized translational degree of freedom, arranged as follows: a first axis A1 which is a rotation axis, a second axis A2 which is a translation axis substantially orthogonal (preferably orthogonal) to A1, and a third axis A3 which is a rotation axis substantially orthogonal (preferably orthogonal) to A1 and A2.

Figure 7:
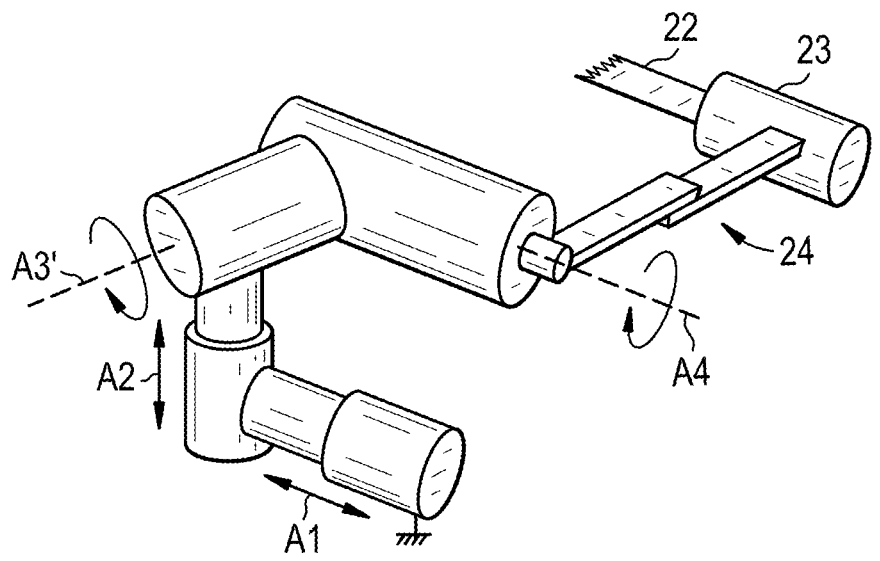
FIG. 7 is a schematic view of the architecture of the actuation unit according to a fifth embodiment.
Figure 8A:
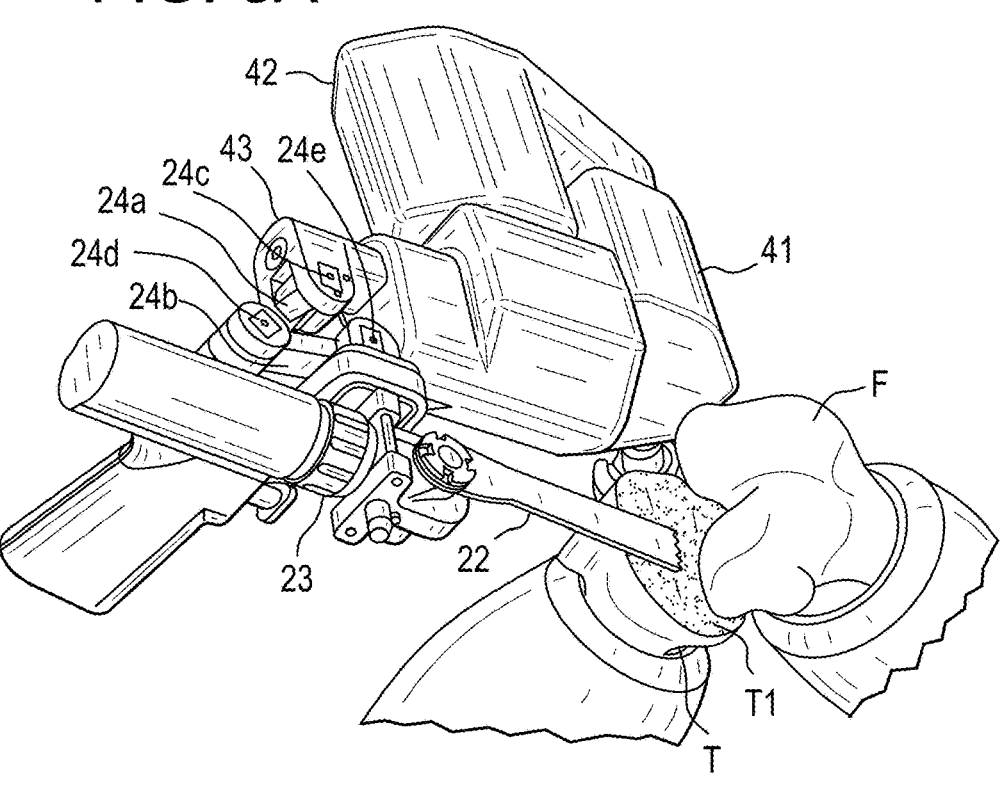
FIGS. 8A-8F show perspective views of a device as shown in FIGS. 3A-3B while carrying out the tibial cut, the distal cut, the anterior cut, the posterior cut, the anterior chamfer cut and the posterior chamfer cut, respectively.
Figure 8B:
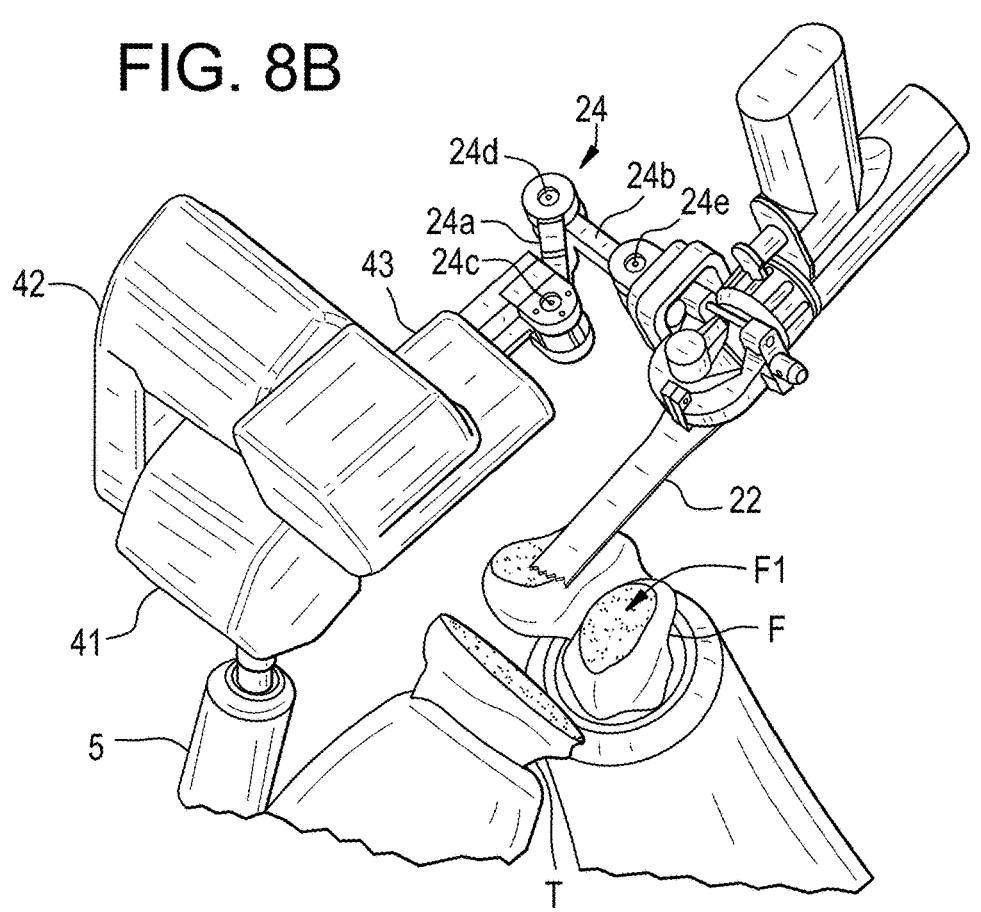
Figure 8C:
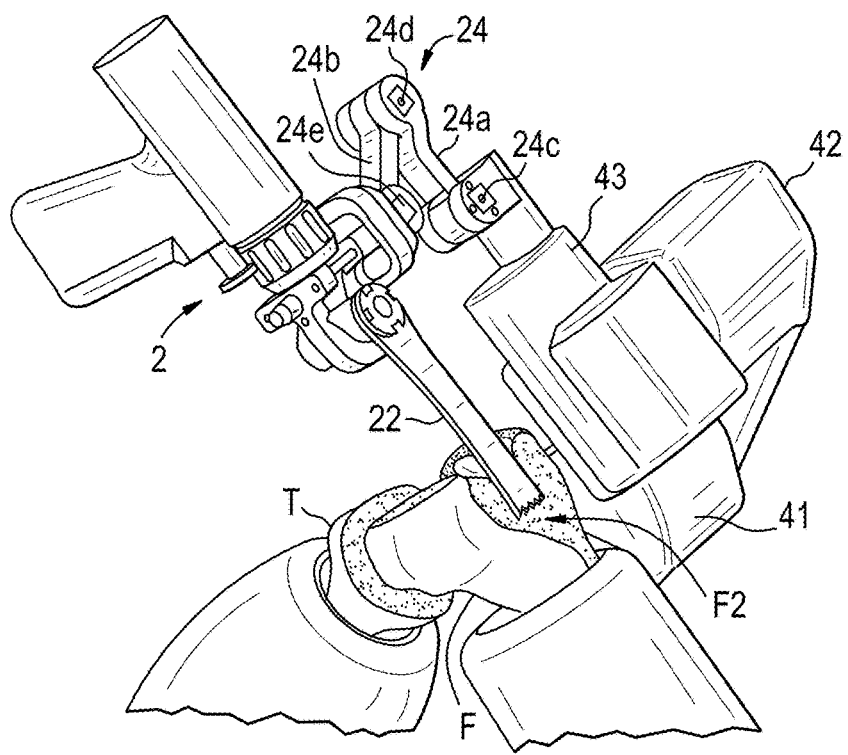
Figure 8D:
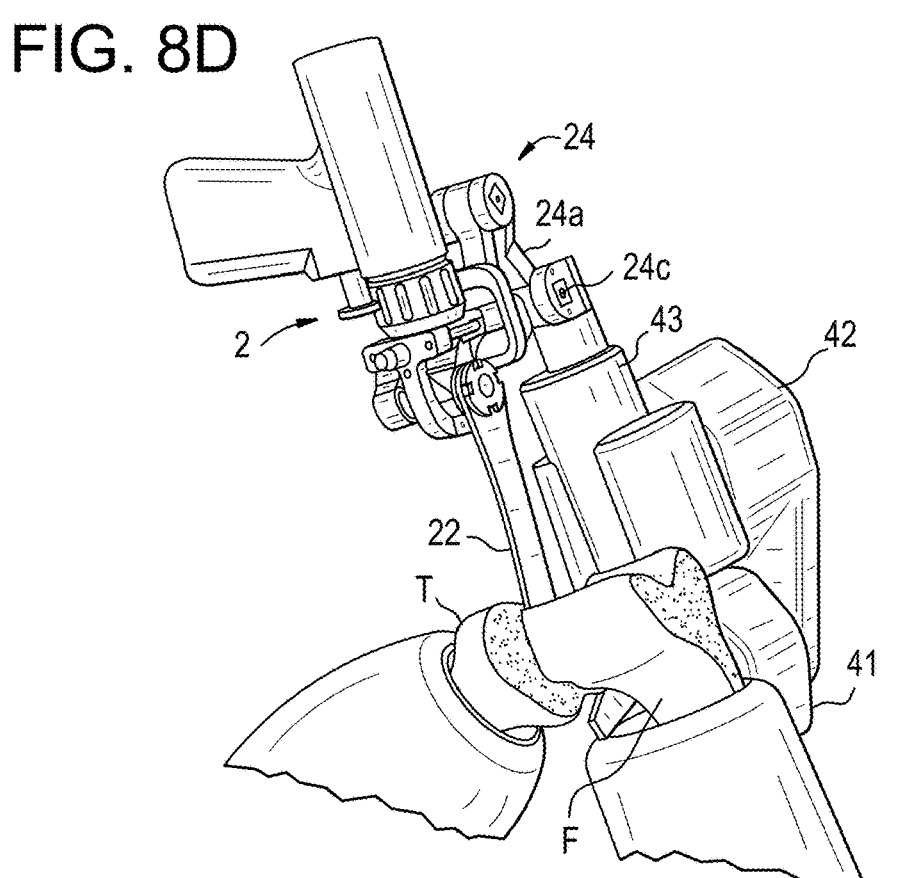
Figure 8E:
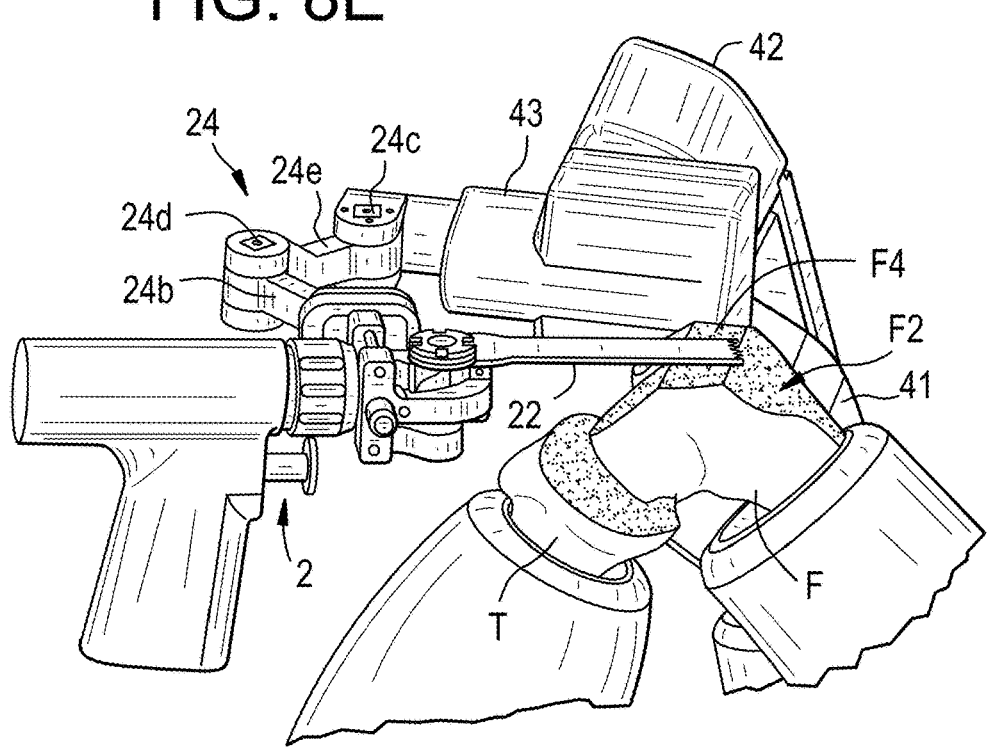
Figure 8F:
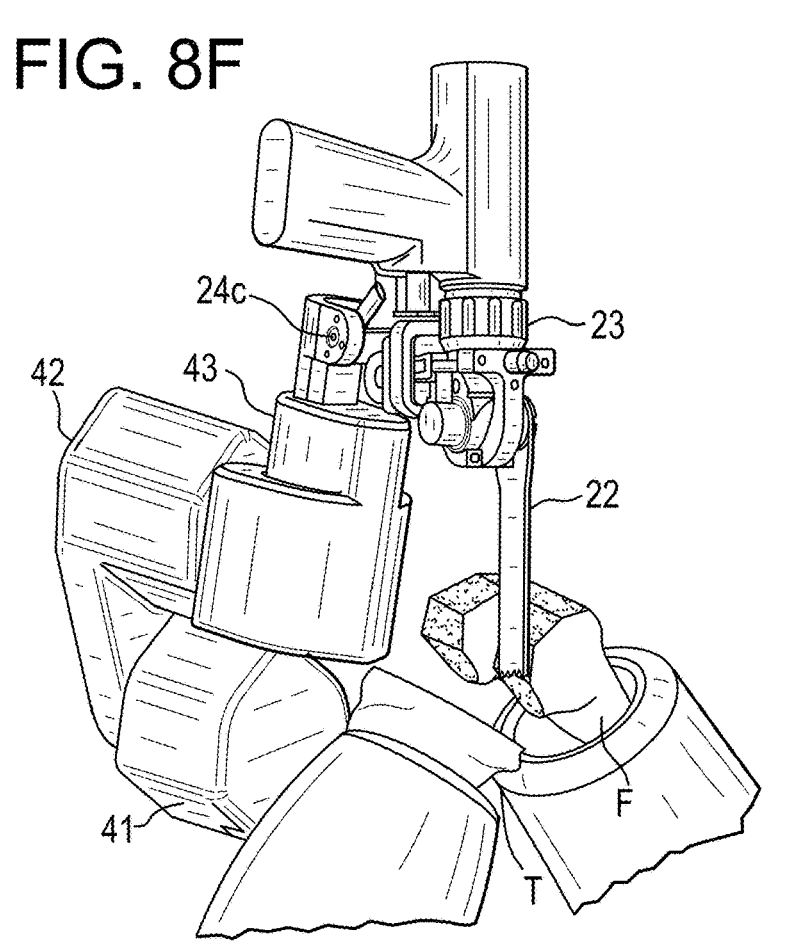

According to an embodiment illustrated in FIG. 7, the actuation unit 4 comprises two motorized rotational degrees of freedom and two motorized translational degrees of freedom, arranged as follows: a first axis A1 which is a translation axis, a second axis A2 which is a translation axis substantially orthogonal (preferably orthogonal) to A1, a third axis A3 which is a rotation axis substantially orthogonal (preferably orthogonal) to A1 and A2, and a fourth axis A4 which is a rotation axis substantially orthogonal (preferably orthogonal) to A3.

In some embodiments, the architecture of the actuation unit may enable additional movements—which can be motorized or not—within the cutting plane. By excluding six motorized degrees of freedom, the described embodiment distinguishes over large surgical robots by a lower inertia—especially according to the first axis—and thus a greater responsiveness required in particular to compensate for bone motion in real time.

As it will be explained in more details below, the actuation unit 4 is controlled by the control unit 300. The control unit may be integrated in the robotic device, or remote from the robotic device.

The cutting tool is coupled to the actuation unit by a planar mechanism designated under reference 24 throughout the set of drawings, the planar mechanism being configured to constrain the movement of the cutting tool within the cutting plane.

Advantageously, the cutting tool can be decoupled from the planar mechanism. Preferably, especially in the case where the cutting tool is not intended to receive a tracker, the attachment means for the cutting tool provides reproducible fixation.

Several different architectures exist to implement a planar mechanism. For example, the planar mechanism can be made of only one rotation axis and then one translation axis that carries the cutting tool along its longitudinal direction. Alternatively, the planar mechanism can be made of two orthogonal translation axes and then a rotational axis. According to another embodiment, the planar mechanism can be a slider in the form of an arch, including a rotation axis, and then a translation axis that carries the cutting tool.

According to an embodiment, the planar mechanism 24 is passive, meaning that the mechanism is not motorized and can be freely manipulated by the user. For example, in the embodiment shown in FIGS. 8A-8F, the passive mechanism 24 comprises segments 24a-24d linked by three parallel rotation axes 24e-24g which are orthogonal to the cutting plane. One advantage of such a passive mechanism is to preserve all the perceptions of the user when the saw is manipulated in the bone. For example, surgeons are used to freely manipulate a saw in a cutting block and to detect when the saw blade has reached the back of the bone by sensing changes in the bone resistance, and this perception is fully preserved with a passive planar mechanism that has very low friction at its joints.

Figure 26:
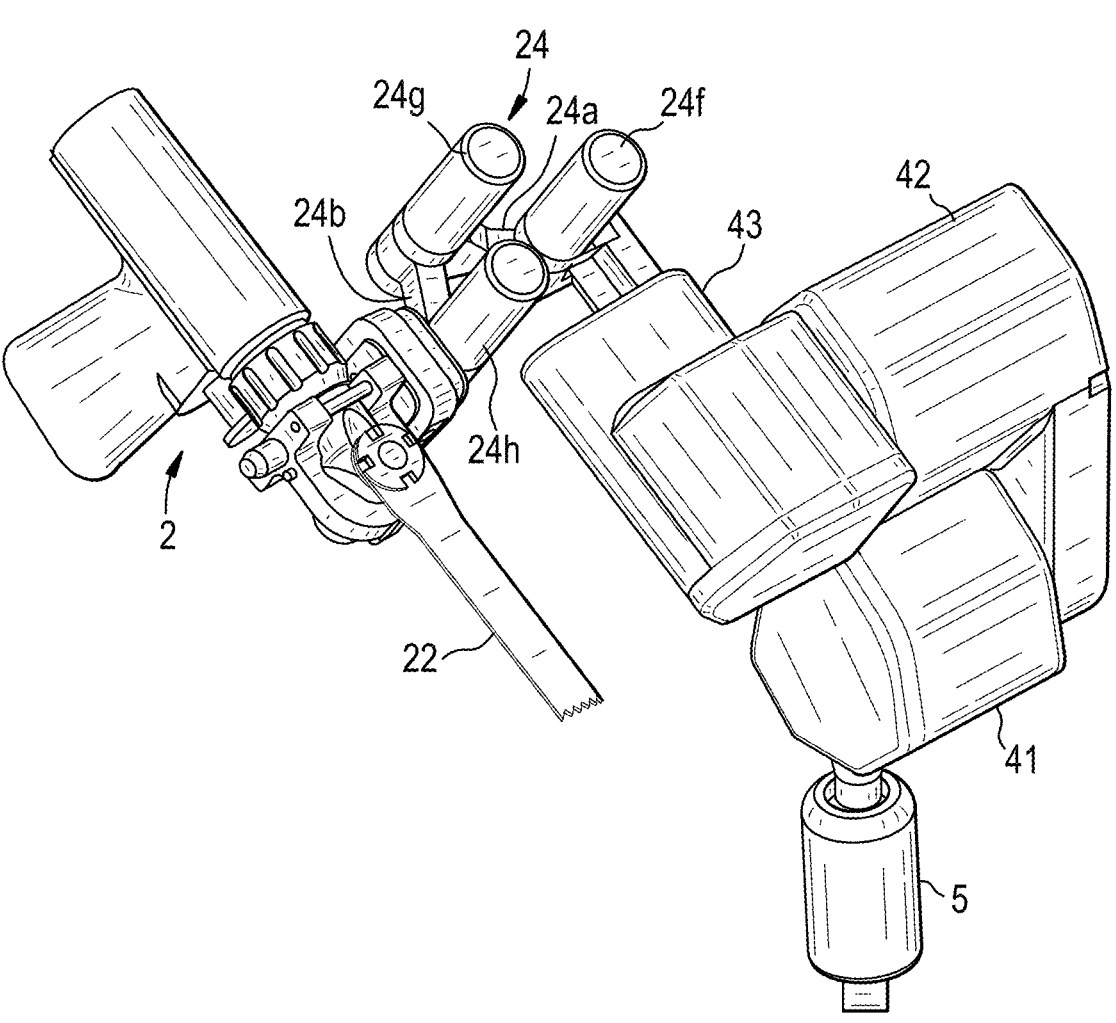
FIG. 26 shows an embodiment of a motorized planar mechanism.

Alternatively, the planar mechanism may also be at least partially active, i.e. comprising at least one motorized degree of freedom. If the planar mechanism is active, i.e. it comprises at least two motorized degrees of freedom (see FIG. 26), the cut(s) can be performed automatically. It is to be noted that said motorized degrees of freedom are all configured to move the cutting tool within the cutting plane.

Whatever the embodiment, the planar mechanism may comprise a locking system for locking each of its degrees of freedom once the cutting plane has been aligned with the target plane.

It is possible to make the actuation unit and planar mechanism sterile components, to be sterilized before each intervention. But, in a preferred embodiment, the actuation unit with its cables and equipped with the planar mechanism are covered by a single-use sterile drape. Additional components of the system can be also protected under the sterile drape. This has the advantage of facilitating and reducing cost of manufacturing and design, but also of being used easily for multiple consecutive surgeries without requiring re-sterilization of the device. The cutting tool itself is sterile, like any conventional surgical tool. Typically, it is sterilized before each intervention using autoclave. Different types of mechanical adaptors between the sterile drape and the cutting tool can be provided. Such adaptor does not require a very precise reproducible fixation if the saw contains a tracking element (described in more detail below), which increases the accuracy of the global system. The sterile drape covers the planar mechanism to facilitate the design and manufacturing of the device. For example, this design allows the use of ball-bearings mechanisms that would be difficult to autoclave.

The system comprises an articulated lockable holding arm 5 supporting the actuation unit and suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm 5 is made of several articulated segments using ball-and-socket joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the cutting tool and reaction forces caused by movements of the actuation unit.

According to an embodiment, the holding arm is passive.

Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm-possibly with a braking force as described above. If a new target position of the robotic device is defined, new braking volumes are defined, and the braking is adjusted based on said new volumes.

In an embodiment, the holding arm is equipped with weights to counterbalance the weight of the control unit, as it is commonly used for carrying and placing microscopes in the surgical field for example.

In an embodiment, the holding arm has a vertical translation with a spring mechanism to compensate for the weight of the global system, then it has a serial architecture with a large planar structure made of three parallel and vertical axes. Each axis is equipped with a locking system.

Figure 9:
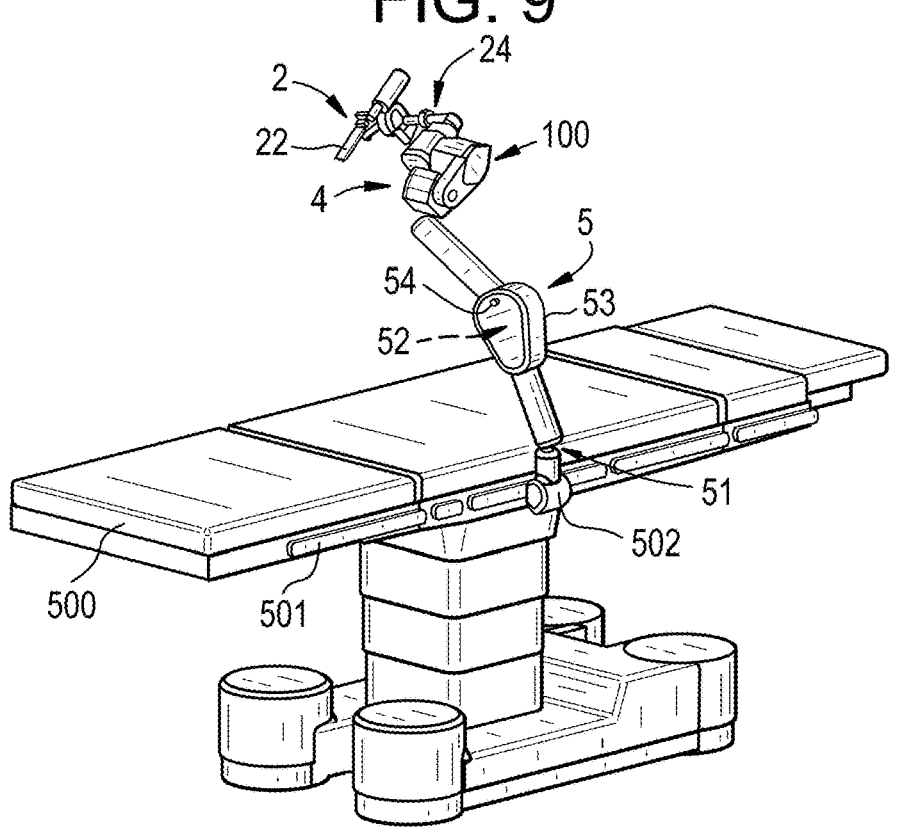
FIG. 9 illustrates an embodiment of the holding arm.

FIG. 9 illustrates an embodiment of the holding arm 5, which is fixed to a rail 501 of the operating table 500 by a clamp 502. The holding arm is formed of the following kinematic links, in a sequence starting from the clamp: a pivot link 51 and a ball joint 52. The central module 53 is provided with an actuator 54 that allows unlocking the holding arm when pushed. Alternatively, such an actuator could be arranged on a higher part of the holding arm so as to manipulate the arm and the robotic device easily in case the user wants to change the position of the robotic device relative to the anatomical structure.

Figure 10:
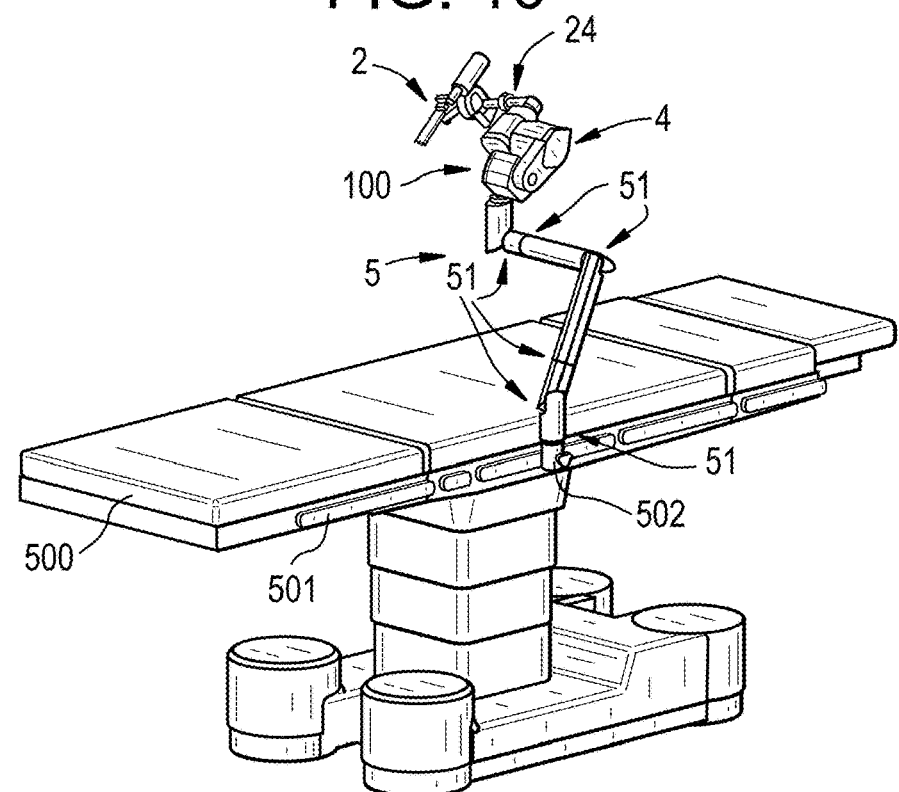
FIG. 10 illustrates another embodiment of the holding arm.

FIG. 10 illustrates another embodiment of the holding arm 5, which is fixed to a rail of the operating table 500 by a clamp 501. The holding arm is formed of six pivot links 51. The holding arm may be locked by an actuator (not shown).

Preferably, the connection between the holding arm and the actuation unit is as close as possible to the first segment of the actuation unit or to the center of gravity of the robotic device in order to minimize any lever-arm effect. The part of the actuation unit that is attached to the holding arm is called the base of the robotic device.

According to an embodiment, the first segment of the actuation unit may be fixed relative to the holding arm. In such case, the second segment of the actuation unit is necessarily mobile relative to the first segment. This architecture is advantageous in that it minimizes the weight of the moving components of the actuation unit. As a result, the robotic device may be more responsive, which is favorable to real time control of the cutting plane.

According to an embodiment, the first segment of the actuation unit may be mobile relative to the holding arm. In such case, the first and second segments are preferably embedded in a single housing.

Figure 11:
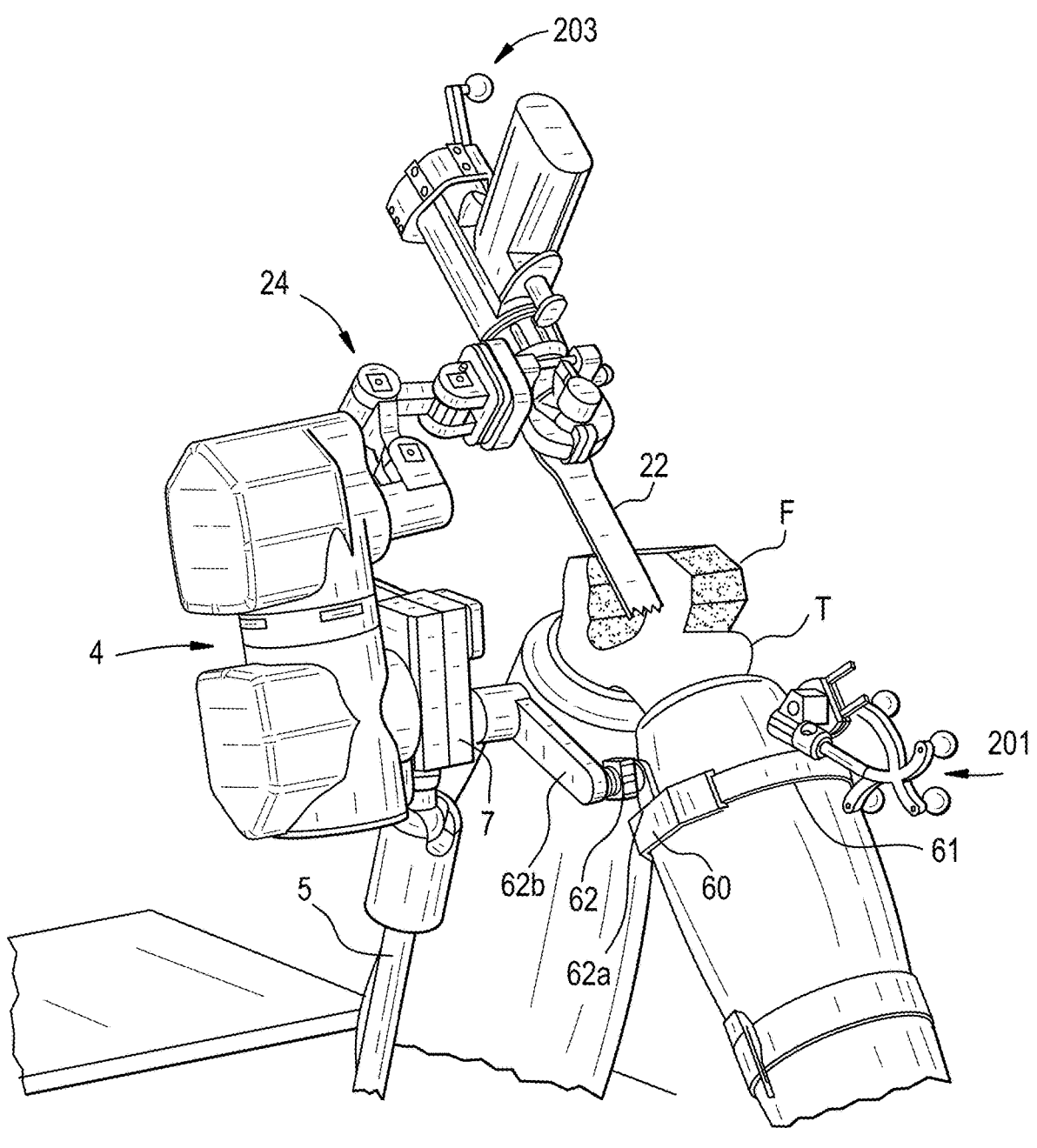
FIG. 11 illustrates an embodiment of a support unit attached to the tibia.

According to an embodiment, the device may further comprise a support unit configured to create a partial mechanical link between the actuation unit and the anatomical structure. The support unit may be attached directly or indirectly to the holding arm or to the actuation unit. In the latter case, the support unit may be attached to a fixed segment of the actuation unit (e.g. the first segment if it is fixed to the holding arm) or to a mobile segment of the actuation unit (freely rotatable about the axis of rotation of the segment relative to the holding arm). According to an embodiment that will be described below with reference to FIGS. 11 and 12, the support unit 6 may be attached to an intermediate part 7 removably attached to the holding arm 5 or to the actuation unit 4. This intermediate part 7 can be for example a sterile part to be placed over the sterile drape (not shown) to create a sterile connection between the support unit 6 and the holding arm or the actuation unit. The support unit is usually a sterile component. The connection between the support unit and the actuation unit or the holding arm can be established on the sterile drape via the intermediate part if the actuation unit is covered with a sterile drape. In case the robotic device is sterile, the support unit can be connected directly to the robotic device.

According to an embodiment, the support unit comprises at least one element intended to make contact with the anatomical structure to be cut or an area of the patient's body adjacent to the anatomical structure to be cut so as to provide a partial mechanical link between the actuation unit and the anatomical structure.

If a support unit is used, it is arranged so as not to hinder the movements required to carry out the surgical intervention. In particular, the support unit is arranged so as not to interfere with the movements of the robotic device to implement each cut.

Generally, the support unit comprises at least one element intended to be in contact with an anatomical structure (the anatomical structure to be cut or an anatomical structure adjacent thereto, e.g. the soft tissues surrounding a bone to be cut). This element 60 can be attached to the patient by at least one strap 61. To that end, this element may comprise at least one slot through which the strap extends. The strap can be flexible or semi-rigid (e.g. like fastening device for ski boots). The strap can be adjusted by any suitable means, such as fastening mechanisms, hoop-and-loop fasteners (also known as Velcro™), etc. Alternatively, the strap can be adhesive, or comprises at least one portion made of a high-friction coefficient material (e.g. soft thermoplastic, silicone) placed in contact with the anatomical structure.

Besides, the support unit 6 comprises a mechanical connection 62 between the base of the actuation unit (or the holding arm or the above-mentioned intermediate part) and the element of the support unit which is in contact with the anatomical structure. The connection can be activated when the robot is in use and deactivated when the surgeon needs to move the leg. According to an embodiment, said connection may be rigid. Alternatively, said connection can be articulated and lockable in at least one degree of freedom to adjust the distance between the robotic device and the patient, or to take into account the patient's morphology. Once the robotic device has been placed in the desired position and orientation, some degrees of freedom may remain free, provided that the support unit still allows limiting movements and vibrations of the anatomical structure relative to the actuation unit. This mechanical connection 62 may be made of at least two parts 62a, 62b detachable from one another, for example using a rapid fixation, latch or magnets. A first part 62a is attached to the element 60 of the support unit in contact with the anatomical structure; a second part 62b is attached to the base of the actuation unit or to the holding arm or to the above-mentioned intermediate part. Thus, the intermediate part, the actuation unit or the holding arm may be disconnected from the anatomical structure simply by releasing the mechanical connection, without any need to dismount the support unit from the patient. This is particularly useful in case the user wants to change the position or flexion of the leg during the intervention, e.g. in view of checking the ligament balancing or the postoperative alignment of the leg.

Figure 31A:
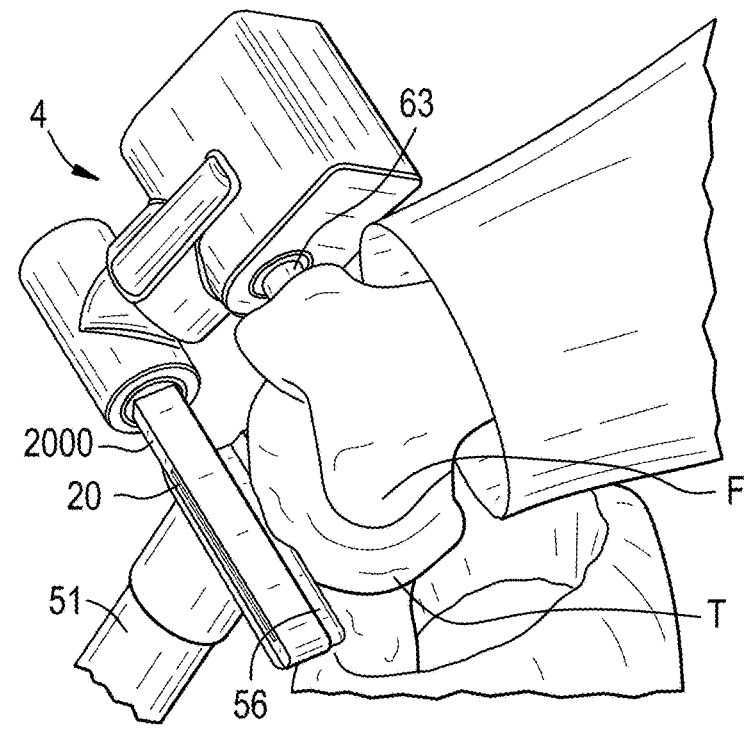
FIGS. 31A-31B show various embodiments of the support unit of the device.
Figure 31B:
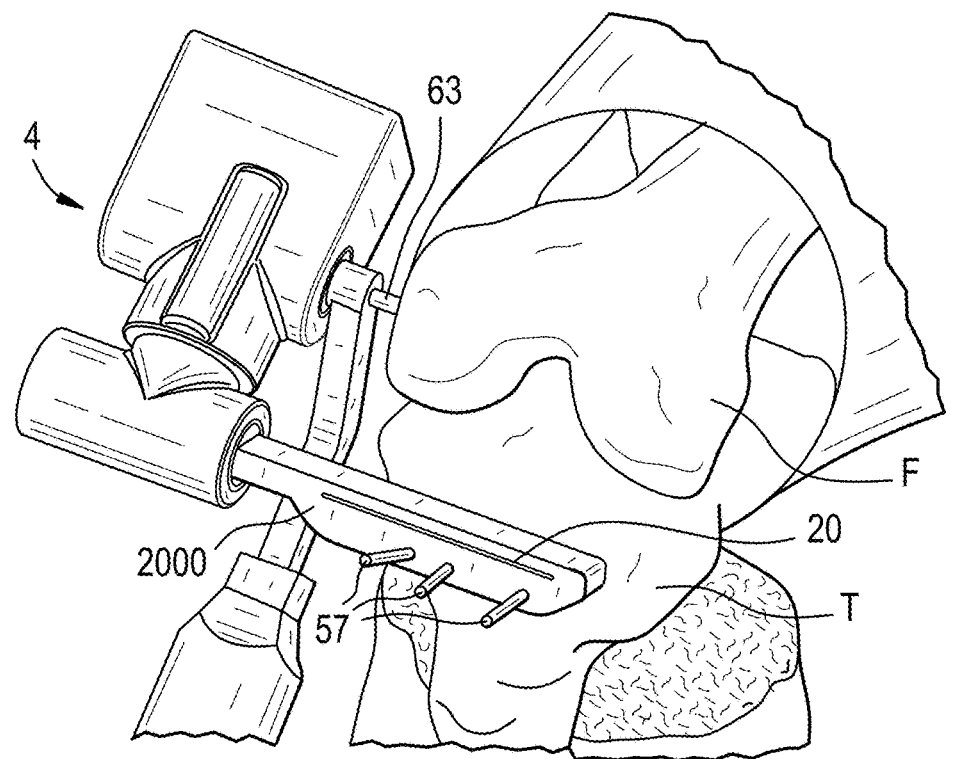

Optionally, the support unit may include, in combination with the above described components, one or several rods 63 intended to be in contact with the anatomical structure (see FIGS. 31A-31B). For example, in the case of TKA, such a rod could be in contact with the epicondyle. Said rod can be rigid or damped (using a spring member). Thus, without being rigidly attached to the bone, said rod allows maintaining a distance between the anatomical structure and the robotic device when the above-described strap is tightened in a determined direction.

In addition to or instead of the rod(s), the support unit may comprise at least one (active or passive) suction pad intended to stay in place on an anatomical structure (bone, skin or other soft tissue) in case of relative movement of the robotic device and the anatomical structure, and also to provide damping.

In a preferred embodiment, the support unit is attached around the leg.

Figure 12:
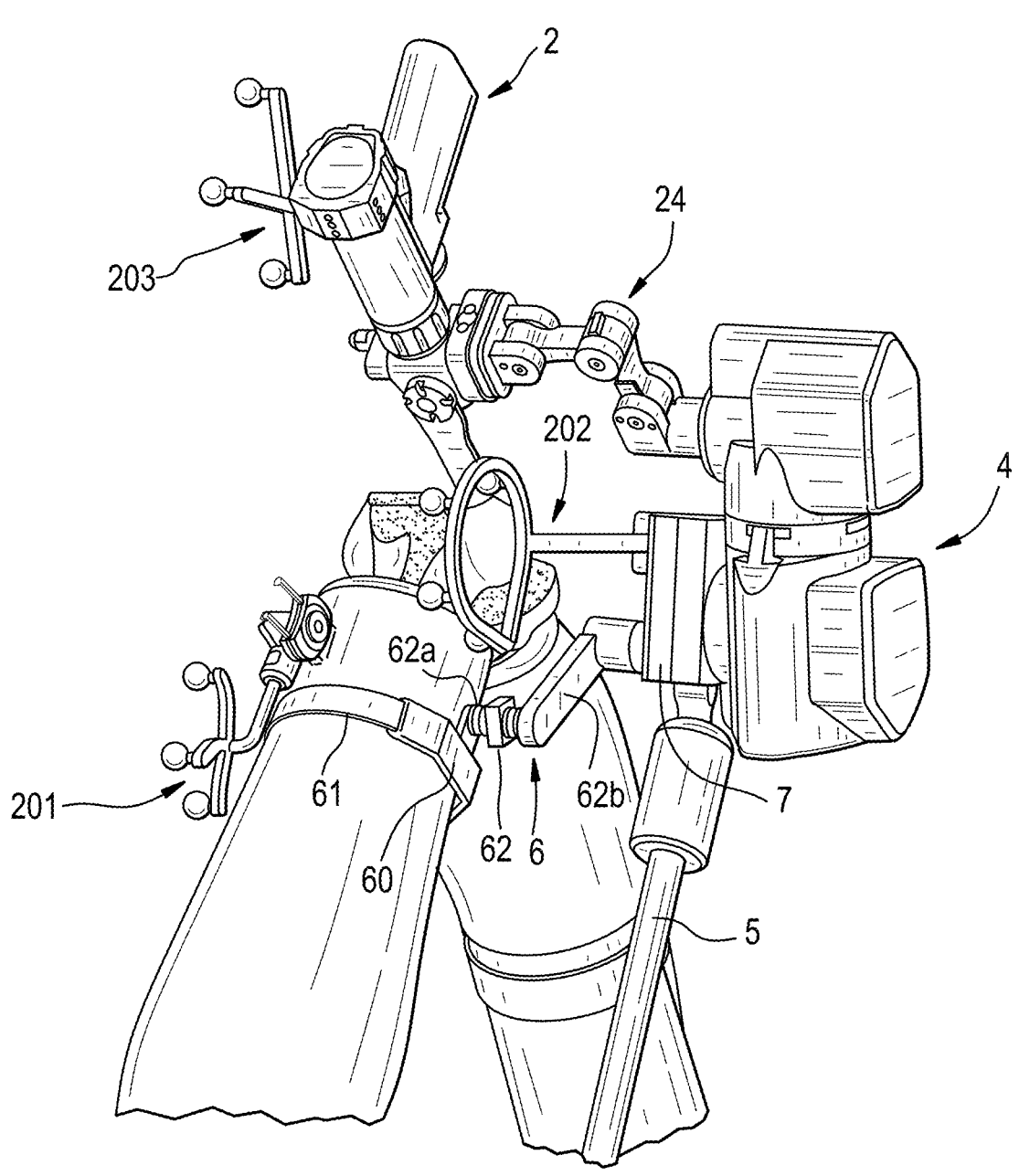
FIG. 12 illustrates an embodiment of a support unit attached to the femur.

The support unit may be attached to the tibia (see FIG. 11) or to the femur (see FIG. 12). The support unit may also be attached to both the tibia and the femur; in this case, the support unit is advantageously articulated so as to enable moving the leg (in particular adjusting the flexion of the leg) without removing the support unit.

According to an embodiment, retractors are attached to the support unit. Said retractors are pulling the soft tissues to offer a large incision and vision to the surgeon. A first retractor can be attached to the medial side of the incision and to the back part of the support unit using a link that can be tensioned. A second retractor can be attached to the lateral side of the incision and to the back part of the support unit using a link that can be tensioned. During maneuvers of the leg, the support unit is detached from the actuation unit basis or holding arm or intermediate part, using a fast but strong mechanical connection.

Figure 13:
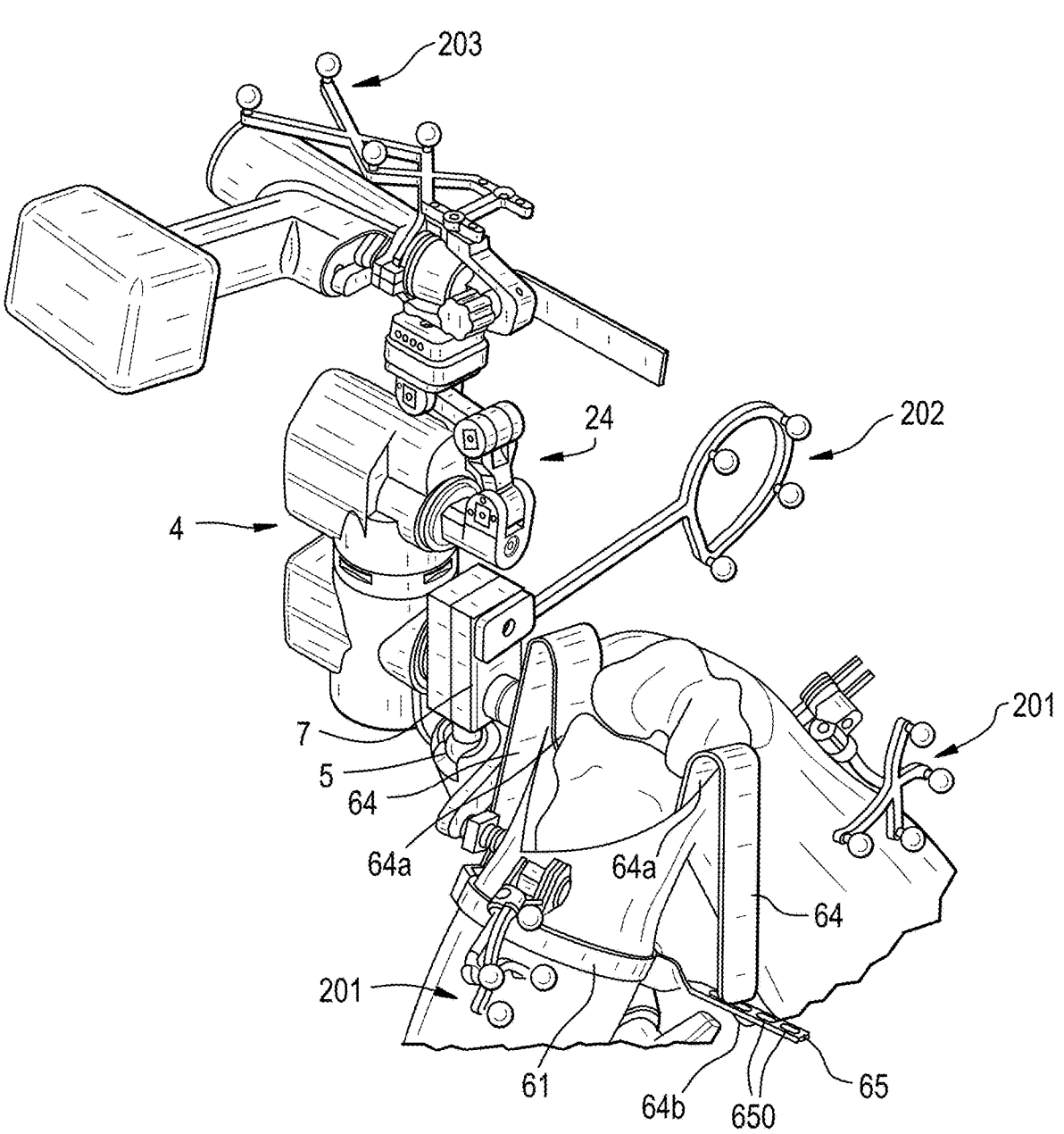
FIG. 13 illustrates an embodiment of a support unit supporting soft tissues retractors.

FIG. 13 illustrates one embodiment of retractors attached to the support unit.

The support unit 6 is attached to an intermediate part 7 that is itself removably attached to the holding arm 5. In particular, the intermediate part 7 allows making a sterile connection with the holding arm 5 over the sterile drape (not shown). The intermediate part 7 may advantageously carry a tracker 202. The support unit 6 comprises a strap 61 supporting a base 61 from which extends a first fastener 62a, and a connecting member comprising a second fastener 62b cooperating with the first fastener to create a fast and strong connector 62, the connecting member being attached to the intermediate part.

Each retractor 64 has a bent shape, with a first end 64a configured to make contact with the anatomical structure and a second end 64b configured to be attached to the strap 61 of the support unit. More precisely, two bars 65 comprise a slot through which the strap 61 passes, so that the bars 65 are maintained in a direction projecting away from the leg. Each bar comprises a plurality of holes 650. The second end 64b of each retractor is inserted into a selected hole 650 of the respective bar 65 such that the first end 64a of the retractor bears against the anatomical structure and sufficiently pulls the soft tissues.

Figure 14:
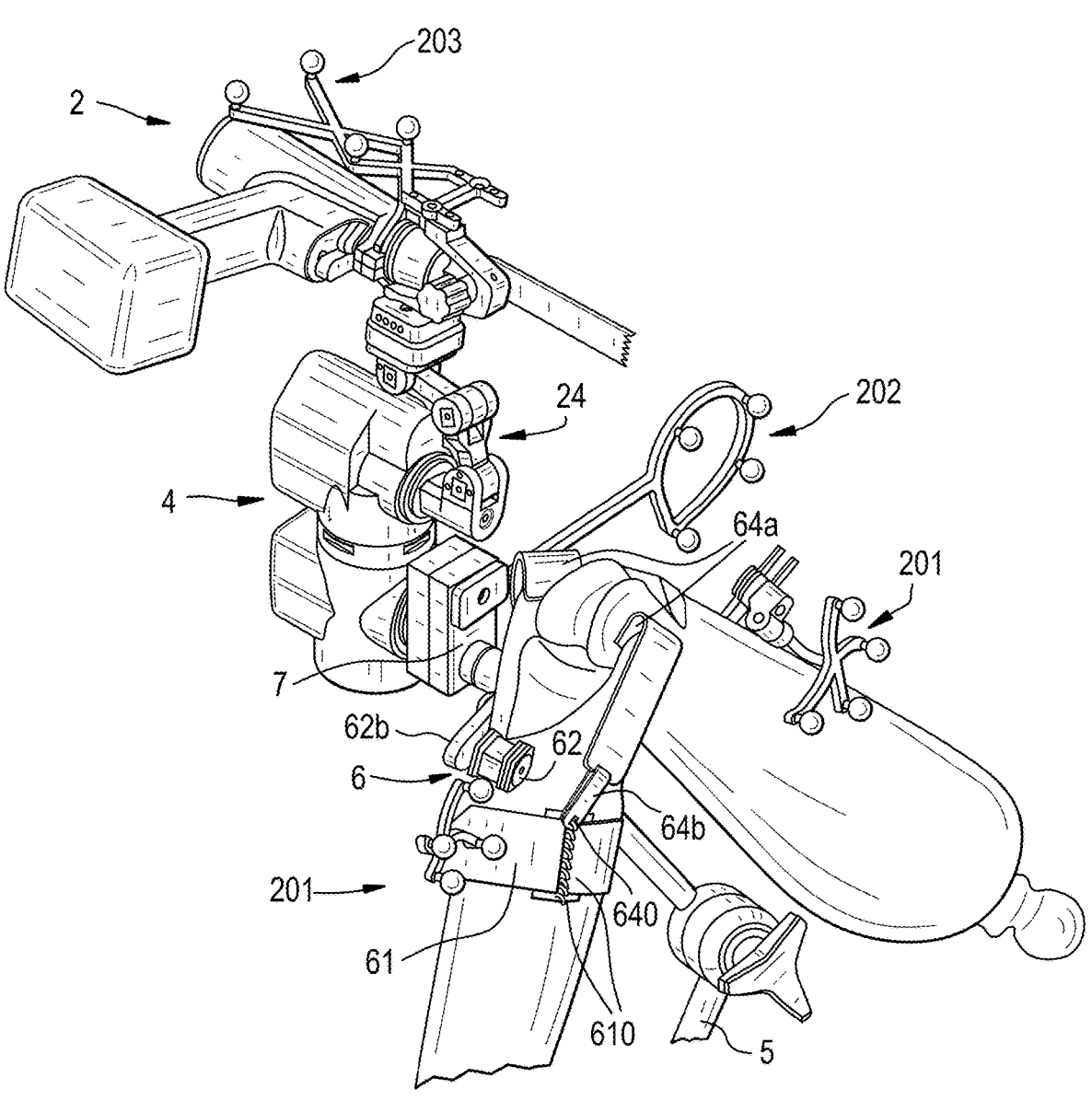
FIG. 14 illustrates another embodiment of a support unit supporting soft tissues retractors.

FIG. 14 illustrates another embodiment of retractors attached to the support unit.

The support unit 6 is attached to an intermediate part 7 that is itself removably attached to the holding arm 5. In particular, the intermediate part 7 allows making a sterile connection with the holding arm 5 over the sterile drape (not shown). The intermediate part 7 may advantageously carry a tracker. The support unit 6 comprises a strap 60 supporting a base from which extends a first fastener, and a connecting member comprising a second fastener cooperating with the first fastener to create a fast and strong connector 62, the connecting member being attached to the intermediate part.

Each retractor 64 has a bent shape, with a first end 64a configured to grip the soft tissues and a second end 64b configured to be attached to the strap 61 of the support unit. More precisely, the strap 61 may be wider than in FIG. 13 and comprises a plurality of hooks 610 on its two sides. The second end 64b of each retractor comprises a hole 640. This hole 640 is coupled with a selected hook 610 of the strap such that the first end 64a of the retractor sufficiently pulls the soft tissues.

Attaching the retractors to the support unit is particularly advantageous in that the retractors need not to be held by the surgeon's assistant, which saves space in the vicinity of the incision.

The support unit acts as a stabilizer. Said support unit may be rigid, damped (e.g. spring-loaded) and/or provide adjustable damping properties. The contact between the support unit and the patient's body may be made of one or several points or of at least one surface.

Before cutting the anatomical structure, the user plans the intervention on the planning system, based on pre-operative and/or intra-operative medical images and data.

This planning step allows determining each target plane suited to perform the cut of the anatomical structure. It is specific to each application.

Figure 15:
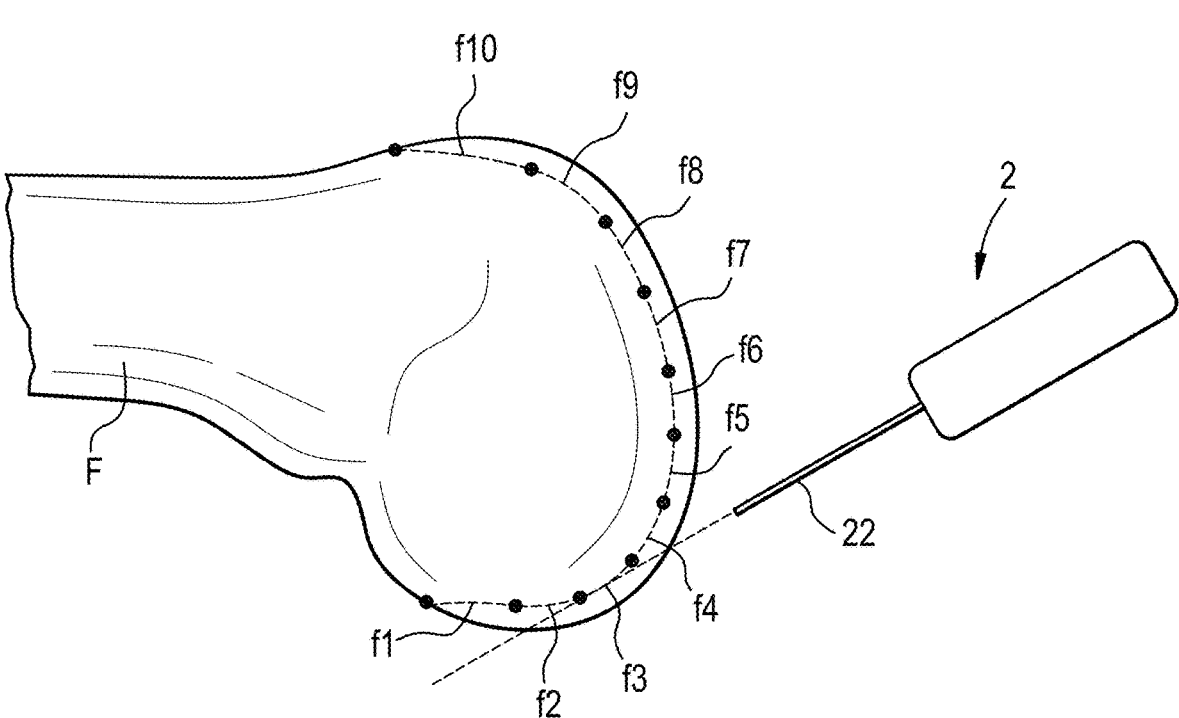
FIG. 15 schematically illustrates an embodiment with ten target planes to be cut on the femur using a robotic device according to the disclosure.

For example, as already described above, in the case of TKA, planning the implantation of a prosthesis on a knee usually results in the definition of five target planes on the femur and one on the tibia. It is also possible to define more than five cutting planes for fixing a prosthesis to a bone in order to optimize the shape of the prosthesis based on individual anatomy for example. This is illustrated in FIG. 15 wherein ten cutting planes f1-f10 are defined to fit the patient's anatomical structure on a sagittal view of a femur. It is particularly advantageous to use the robotic device according to the present disclosure for such bone preparation, to enable to quickly perform many cuts with high accuracy.

The planning system may form part of the surgical system; otherwise, the planning system may be provided separately and connected to the control unit.

During the surgical intervention, the user may either use preoperative data/images together with intra-operative registration methods, or use directly intraoperative data/images. In both cases, the result of the planning consists of at least one target plane, the pose of each plane being determined in the coordinate system of the anatomical structure to be cut.

The pose of each target plane is then transferred to the control unit.

The control unit initializes its sub-systems and the device is ready to use.

Before starting the device, the articulated holding arm is moved by a user so as to bring the actuation unit in a rough suitable position relative to the anatomical structure, and is then locked. Then, the cutting tool is attached to the planar mechanism.

In case a support unit is also used, the support unit is connected to the anatomical structure to be cut or to an adjacent region of the patient's body to provide a partial mechanical link between the actuation unit and the anatomical structure. The partial mechanical link provided by the support unit enables the user to make small movements to reposition the device, or enables the robotic device to compensate for involuntary motion of the patient. No additional invasive action (e.g. implantation of pins) on the patient is required.

Once operation of the device has been started by the user, the tracking unit continuously feeds back tracking information to the control unit for recalculation and visualization purposes.

In addition, the user interface provides information to the user about the ability to align the cutting plane with the target plane in the current device position and, if appropriate, gives indications on how to reposition the device appropriately.

The system also comprises a tracking unit 200 configured to determine in real time the pose of the saw with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of each segment of the actuation unit is known in real time thanks to encoders or sensors of the motors, and a calibrated model of the robot that includes all axes and distances of the robot segments. Using this model, and well-known geometric modeling techniques in robotics, it is possible to calculate the relative positions of all segments, so if one measurement is known in a coordinate system attached to the robot basis using an external tracker, then any segment position is also known in the same coordinate system. Additionally, if a tracker is attached to the base of the actuation unit and a second tracker is attached to the anatomical structure, then the pose of any segment of the actuation unit is known in the coordinate system attached to the tracker of the anatomical structure.

In a preferred embodiment, a first tracker is attached to the first or second segment of the actuation unit and a second tracker is attached to the end effector in order to offer a redundant and more accurate measurement of the end effector position and orientation for safety purpose, taking into account any mechanical backlash that may exist between the actuation unit and the end effector.

In addition, at least one tracker is rigidly attached to the patient's anatomical structure to be cut so as to allow localizing the cutting plane relative to the coordinate system of this anatomical structure to be cut.

Throughout the set of drawings, a tracker attached to the anatomical structure is designated by reference 201, a tracker attached to the actuation unit or to the holding arm is designated by reference 202, and a tracker attached to the end effector is designated by reference 203.

Thanks to the tracker attached to the end effector, the motion compensation is improved. This additional tracker allows determining reliably the position and orientation of the end effector in the coordinate system of the robotic device.

Instead of attaching said additional tracker to the end effector, it is possible to rigidly attach it to the end of the planar mechanism (if any) opposite the actuation unit. Said end of the planar mechanism may comprise an interface capable of receiving any type of cutting tool as mentioned above (sagittal saw, reciprocal saw, burr . . . ) but also other surgical tools such as a drill guide to be used to drill the pegs for implanting the prosthesis, and/or a cutting guide, etc. For example, the drill guide can have a toothed end intended to grip into the surface of the anatomical structure where a hole has to be drilled. Advantageously, a handle is provided at the opposite end of the drill guide to facilitate its manipulation by the surgeon. Thus, once the toothed end has been applied to the anatomical structure, the surgeon can simply change the orientation of the drill guide thanks to a navigation interface. The drill may carry a tracker, instead of having the tracker carried by the end of the planar mechanism.

The compensation of relative motion between the robotic device and the anatomical structure using the additional tracker rigidly attached to the cutting tool or to the end of the planar mechanism may be implemented as follows.

In the control loop, the actual position of the end effector or of the end of the planar mechanism (if any) is used instead of the theoretical position of the output plane of the actuation unit or of the planar mechanism.

This greatly increases the confidence in the compensation mechanism.

Moreover, the association of the tracker attached to the cutting tool and the tracker attached to the actuation unit enables dynamic estimation of the alignment error between the two. This alignment error is then used to correct the position and orientation of the planar mechanism to the target plane.

Figure 16:
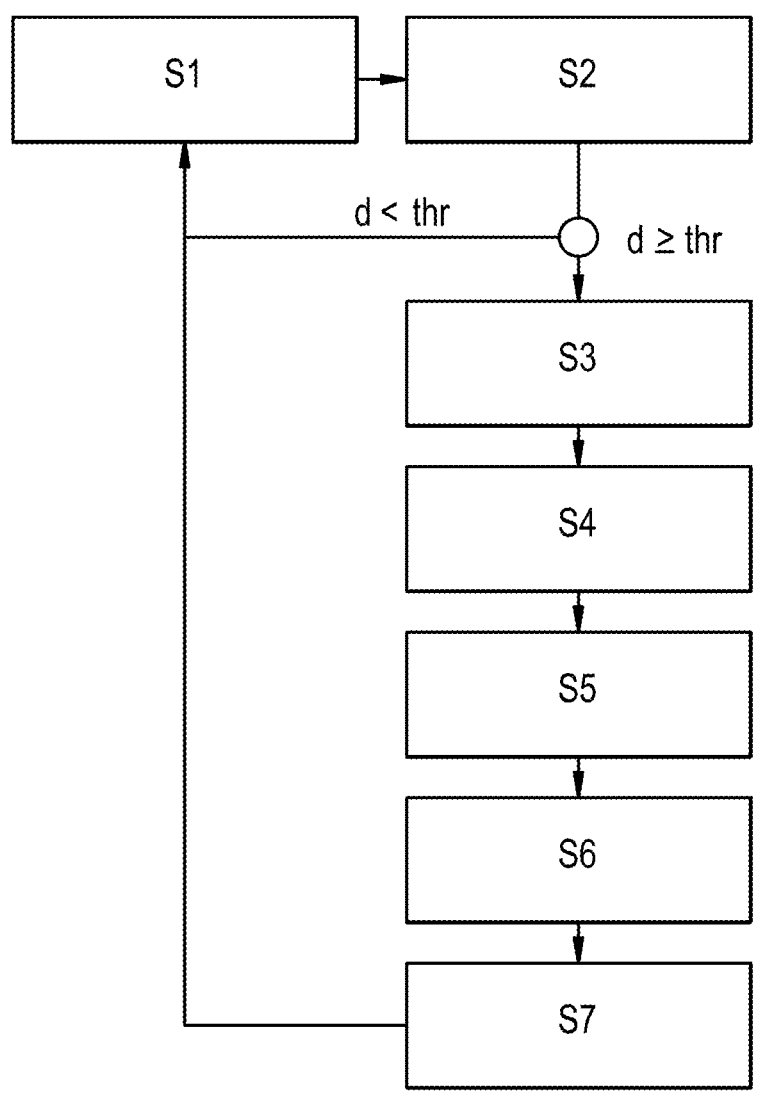
FIG. 16 represents an embodiment of a compensation control loop implemented by the control unit, making use of the tracker that is attached to the end effector.

FIG. 16 is a flowchart describing the control loop allowing the compensation.

In step S1, new poses of the robotic device, the end effector and the anatomical structure are determined using localization information provided by the trackers.

In step S2, a deviation d between the plane of the end effector (cutting plane) and the target plane is computed. In this step, both planes are known in the coordinate system of the localizing system (e.g. the tracking camera in case of optical tracking).

If the deviation d is less than a threshold thr, the cutting tool can be operated and a new pose of the robotic device and anatomical structure is determined (step S1).

If the deviation d is greater than or equal to the threshold thr, then in step S3 the plane of the end effector (cutting plane) and the target plane are projected (i.e. expressed) in the coordinate system of the robotic device. This change of coordinate system allows determining how to move the robotic device relative to the target plane (in step S6 below).

In step S4, a correction matrix Terr corresponding to a rigid transformation between the output plane of the actuation unit (or the plane of the planar mechanism if any) and the cutting plane is computed. Since the actuation unit (or planar mechanism) belongs to the robotic device, both planes are expressed in the same coordinate system which is the coordinate system of the robotic device.

In step S5, the target plane is updated with Terr.

In step S6, a new attitude of the robotic device is computed to reach the target plane. This computation determines the movements to be applied by the motors of the actuation unit.

In step S7, the motors of the actuation unit are activated in accordance with step S6.

Then, the new position of the robotic device and anatomical structure is determined (step S1).

From this base algorithm, further improvements have proven to enhance the behavior of the robotic device:

spatially filtering the positions of the various elements (for instance thanks to a Kalman filter or equivalent);

averaging the estimation of Terr in a given time frame, for instance thanks to quaternion averaging techniques. This allows reducing the potential oscillations due to small inconsistencies between the transformation estimation and the more complex reality of the mechanical links.

The correction matrix Terr may vary depending on the current extension of the planar mechanism and therefore it is not constant. It also depends on the mechanical backlash and flexion of the planar mechanism, the position of the robot, and other factors. The correction matrix is calculated in real time, such that the deviation of Terr between two calculations is not significant, considering reasonable motions of the saw by the user. This method of correction is extremely precise and efficient for compensating any mechanical defects, backlash and errors in the model.

As explained above, such a control loop may be implemented by the control unit at a high frequency, e.g. a frequency greater than 100 Hz, based on tracking information acquired at an at least twice greater frequency, e.g.

greater than 200 Hz or even greater than 300 Hz. Indeed, the implementation of this control loop does not involve complex and long computation. If necessary, parallel computing can be implemented in order to reduce the computation time.

Besides, providing the end effector with a tracker also allows operating the robotic device even if the tracker attached to the actuation unit is visible intermittently by the tracking camera. Such an intermittent visibility may be caused by a member of the medical staff or an equipment of the operating room interposed between the tracker and the camera.

Figure 17:
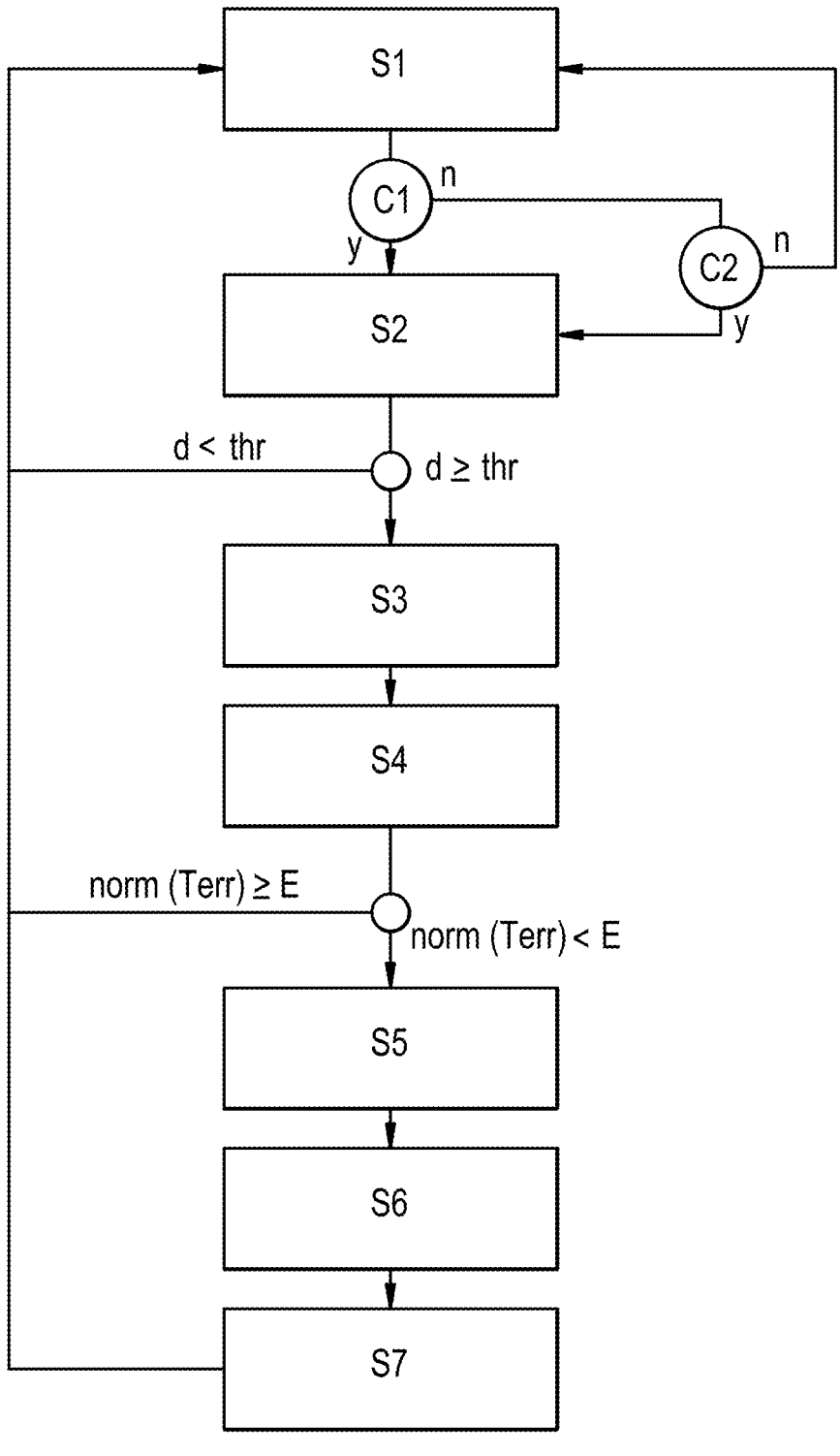
FIG. 17 represents an embodiment of the compensation control loop configured to allow operation of the robotic device in case of intermittent visibility of the tracker attached to the actuation unit.

To that end, the control loop comprises a few additional steps as compared to the one described above. This adapted control loop is represented in FIG. 17. The steps having the same numbering in both control loops are the same and will not be described in detail again.

In step S1, new poses of the actuation unit, the end effector and the anatomical structure are determined using localization information provided by the trackers.

In step C1, the control unit assesses whether a current pose of the actuation unit can be computed based on the localization information provided by the tracking unit.

If the current pose of the actuation unit can be determined, it is stored for later use in a memory of the control unit.

If the current pose of the actuation unit cannot be determined (e.g. because the tracker is not visible) the control unit assesses in step C2 whether a previous pose of the actuation unit is stored in the memory of the control unit. The previously stored pose can be used, if available. If no pose of the actuation unit is currently stored, or if the pose of the end effector or the anatomical structure cannot be determined, the robotic device stops and the system loops back to step S1.

In step S2, a deviation d between the plane of the end effector (cutting plane) and the target plane is computed.

If the deviation d is less than a threshold thr, the end effector can be operated, and new poses of the robotic device, the end effector and the anatomical structure are determined (step S1).

If the deviation d is greater than or equal to the threshold thr, then in step S3 the plane of the end effector (cutting plane) and the target plane are projected (expressed) in the coordinate system of the actuation unit according to the last known pose of the actuation unit.

In step S4, a correction matrix Terr corresponding to a rigid transformation between the output plane of the actuation unit (or the plane of the planar mechanism if any) and the plane of the end effector is computed.

A norm of the correction matrix Terr (noted norm (Terr) is then computed.

If this norm exceeds a determined threshold E (implying a too high difference between the expected position of the plane of the end-effector and the output plane of the actuation), then:

if the pose of the robotic device that is currently used was the previously stored one (i.e. the pose of the robotic device could not be determined during the current iteration of the control loop), then the robotic device stops, the previously stored pose of the robotic device is erased and the control unit loops back to step S1. The rationale is that the base of the robotic device may have moved in a non-negligible way, and the system needs to determine the new pose of the robotic device;

if the pose of the robotic device is an up-to-date one (i.e. the pose of the robotic device could be determined during the current iteration of the control loop), then the robotic device stops and an error is output by the control unit. The rationale is that in this case the discrepancy between the expected position of the plane of the end-effector and the output plane of the actuation unit (or the plane of the planar mechanism if any) is too big and a mechanical problem, which cannot be solved by rendering the tracker visible again, may have caused it.

According to an embodiment, the robotic device may comprise a light emitter configured to be activated by the control unit to emit light when the norm of the correction matrix is greater than the threshold. For example, the light emitter may comprise at least one LED that may emit a continuous light as long as the norm of the correction matrix is smaller than the threshold, and a flashing light as soon as the norm of the correction matrix exceeds the threshold. Such a light emitter is advantageously arranged in a location that is close to the cutting plane. Thus, the user can be provided with visual information that the tracker of the actuation unit is not visible.

According to an embodiment, the control unit may be configured to output a message to the user to ask him/her to make sure that the tracker of the actuation unit is in the field of view of the camera, and/or that a mechanical problem may have occurred. For example, said message may be displayed as a text on a screen coupled to the control unit.

If the norm of the correction matrix Terr is smaller than the threshold E, the target plane is updated with Terr in step S5.

In step S6, a new attitude of the robotic device is computed to reach the target plane. This computation determines the movements to be applied by the motors of the actuation unit.

In step S7, the motors of the actuation unit are activated in accordance with step S6.

Then, new poses of the robotic device, the end effector and the anatomical structure are determined (step S1).

Figure 18:
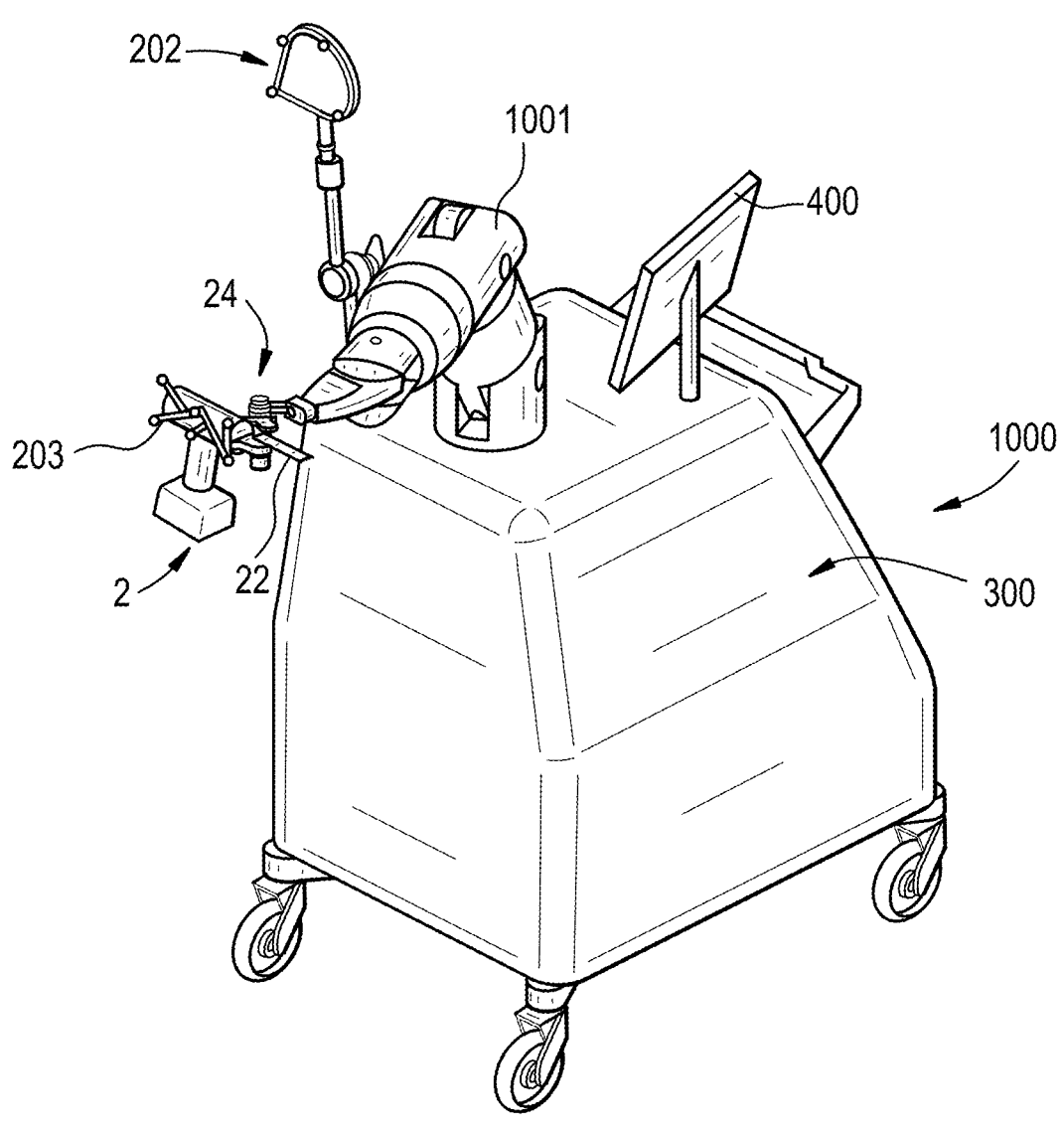
FIG. 18 illustrates a situation where a large robot with six degrees of freedom is equipped with a planar mechanism.

Incidentally, it is to be noted that the compensation methods as described above are also advantageous for large surgical robots with six degrees of freedom holding an end effector, with or without a planar mechanism. In particular, since the planar mechanism is very close to the surgical field, it has to remain compact and thus prone to bending under efforts exerted by the surgeon when cutting. Even if the large surgical robot is accurate, it cannot itself compensate for such bending of the planar mechanism. However, using a tracker on the end effector and implementing the above-mentioned compensation method allows overcoming this problem. FIG. 18 illustrates such a large robot. The robot 1000 comprises an arm 1001 having a serial architecture comprising six motorized degrees of freedom, a planar mechanism 24 connecting the last segment of the arm to a cutting tool 2. The robot is used with a tracking unit configured to determine in real time the pose of the cutting plane with respect to the coordinate system of the anatomical structure of the patient. The tracking unit comprises at least one tracker (not shown) configured to be attached to the anatomical structure, a tracker 202 attached to a segment of the arm of the robot and a tracker 203 attached to the end effector. The robot is controlled by a control unit configured to determine the pose of the cutting plane with respect to the target plane and to control the arm so as to bring the cutting plane into alignment with the target plane. The control unit is configured to implement a compensation method including the following steps:

(S1) determining poses of the arm, the end effector and the anatomical structure using localization information provided by the trackers of the tracking unit;

(S2) computing a deviation between the cutting plane and the target plane;

if the deviation is less than a threshold, allowing operation of the cutting tool and returning to step (S1) to determine a new pose of the arm, end effector and anatomical structure;

if the deviation is greater than or equal to the threshold, expressing (S3) the cutting plane and the target plane in the coordinate system of the robot, (S4) computing a transformation between the output plane of the actuation unit or of the plane of the planar mechanism and the cutting plane;

(S5) updating the target plane with the transformation computed in step (S4);

(S6) computing a new attitude of the robot to reach the updated target plane, and determining the movements to be applied by the motors of the arm.

Advantageously, the attachment of the trackers to the end effector and/or actuation unit is reversible and reproducible.

According to an embodiment, instead of the tracker being attached to the actuation unit, the system also comprises a tracker attached to the intermediate part (part 7 shown in FIGS. 11-14) connecting the support unit to the holding arm or to the actuation unit, to the holding arm provided that the connection between the robotic device and the holding arm is sufficiently rigid (without any mechanical play), and/or a tracker attached to any other component rigidly connected to the robotic device.

As mentioned previously, a user interface is defined so as to show the user a potential position and orientation of the actuation unit suitable for aligning the cutting plane with a target plane.

From time to time, the user interface may provide information to the user to guide him or her to reposition the actuation unit in an optimal pose to enable alignment of the cutting plane with a target plane. The user interface may also indicate to the user if all targeted cutting planes can be reached from the current position of the actuation unit, and if not, in which direction to move to reach an optimal position.

Said user interface may be visual and/or acoustic.

According to an embodiment, the user interface may comprise a screen connected to the control unit, e.g. the screen 400 shown on FIG. 2.

Figure 19A:
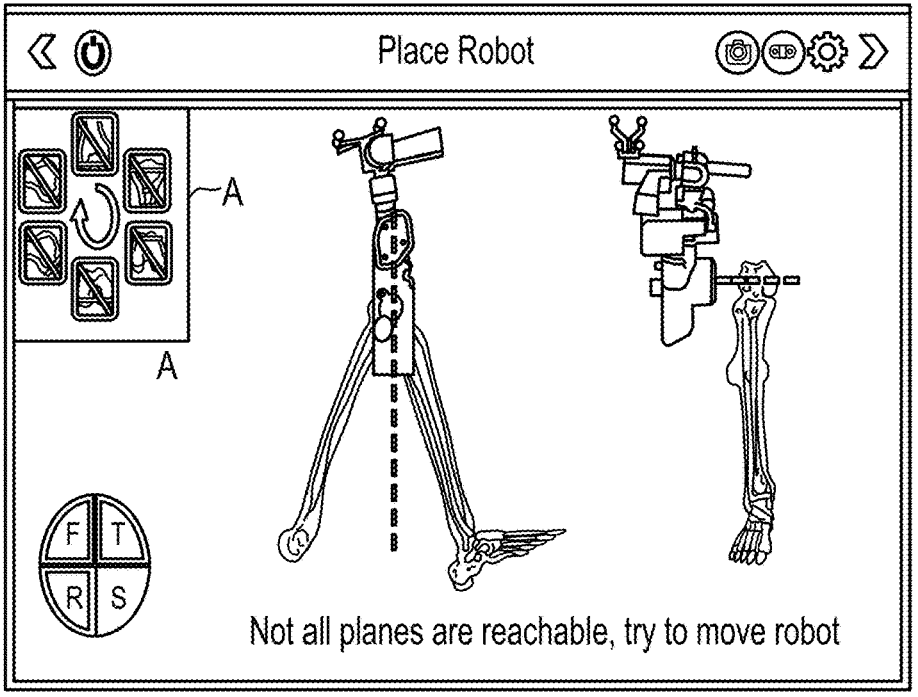
FIGS. 19A-19C illustrate an embodiment of the user interface for guiding the positioning of the robotic device to carry out several cuts on the femur and the tibia.
Figure 19B:
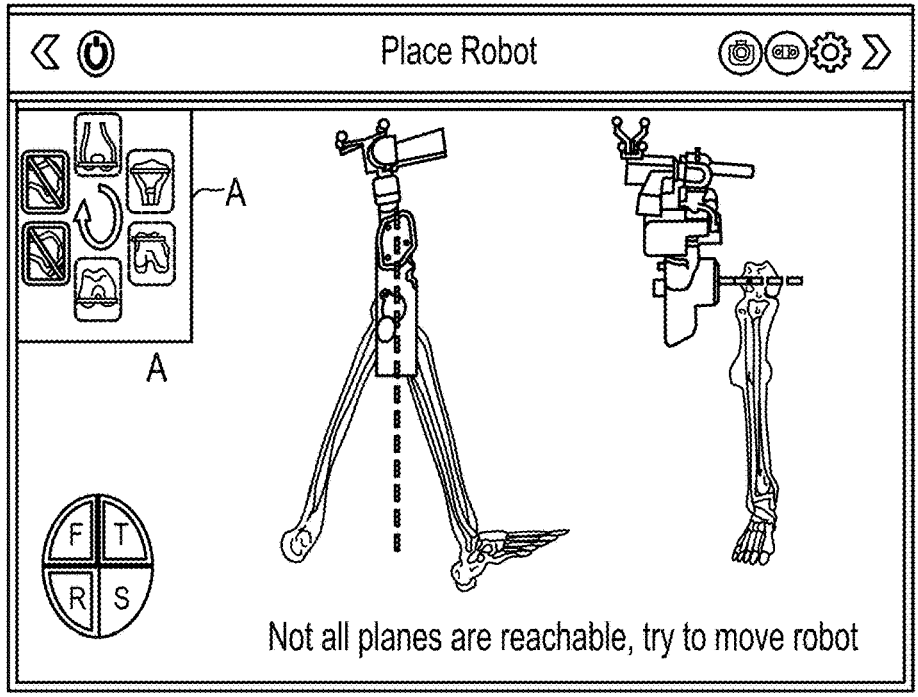
Figure 19C:
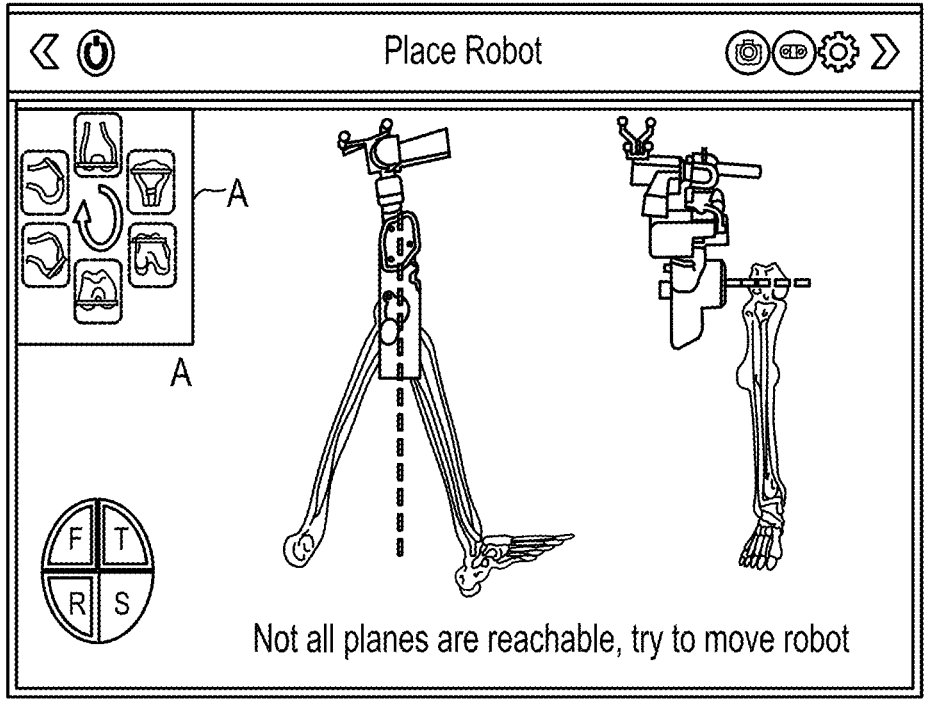

FIGS. 19A-19C show three views of the screening corresponding to different poses of the robotic device. In the situation of FIG. 19A, the robotic device is in a position and orientation that does not enable performing any of the planned cuts. This is illustrated by the icons in region A representing each of the six target planes required for TKA being crossed. In the situation of FIG. 19B, the robotic device is in a position and orientation that enables performing some of the planned cuts, but not all. This is illustrated by the icons representing two of the six target plans required for TKA being crossed in region A. In the situation of FIG. 19C, the robotic device is in a position and orientation that enables performing all of the planned cuts. This is illustrated by the fact that none of the icons of region A representing the six target planes required for TKA is crossed.

Thus, with such a user interface (other embodiments are described below), the user is able to position the robotic device so that the system is capable of performing all six cuts (five femoral cuts and one tibial cut) for TKA without requiring any repositioning of the robotic device. In this way, TKA surgery can be implemented much faster than with prior art devices.

If a realistic 3D model of the anatomical structure is available (i.e. obtained by pre-operative or per-operative imaging of the patient), it may be displayed on the screen, along with a real-time representation of the cutting tool (e.g. envelope of the oscillating blade). For instance, if the cutting tool is a saw, the user can visualize the position of the tip of the saw blade relative to the bone, to ensure that the tip of the saw blade does not exit from the bone. In case the planar mechanism connecting the saw to the actuation unit is motorized, this control may be automated.

During the use of the device the control system checks in real time if the saw can be aligned with a target plane. If the robotic device is moved such that the saw cannot be aligned with said target plane—e.g. in case of vibrations, and/or an involuntary movement of the patient—, then the information provided to the user may change, e.g. the color of the arrow is changed or an acoustical feedback is produced.

According to another embodiment (not shown), the user interface comprises visual indicators such as LEDs. These LEDs may be arranged on a supporting surface that is fixed to the robotic device. Alternatively, the LEDs may be arranged on a support separate from the robotic device and connected to it by a wire. Alternatively, the LEDs may be arranged on a support separate from the robotic device and wirelessly linked to the robotic device. Such a separate support can be placed in the vicinity of the robotic device/cutting tool, in the user's field of view.

Said indicators are intended to instruct the user not to activate the cutting tool, in case the robotic device is not able to compensate for a misalignment between the cutting plane and the target plane. For example, a red and blinking light is turned on as soon as the trackers mounted on the anatomical structure and/or the cutting tool are not visible. It is turned off or changed to a green light as soon as the visibility of trackers is restored.

Another way of providing information to the user is to use numerical displays (e.g. provided by LCD screens) that represent virtual spirit levels. The general orientation of the robotic device can be adjusted by the user based on one virtual spirit level on top of the robotic device and another one on a side (opposite to the patient's leg) of the robotic device. The distance of the robotic device can be adjusted using a support unit, and/or using indicators such as LEDs representing an arrow pointing the desired direction, and/or via the screen of the user interface.

The system further comprises a control unit which is intended to control the pose of the saw in an optimal way in order to align it with a target plane.

According to an embodiment, the control unit may be coupled to the surgical saw used to perform the cut and configured to allow the actuation of the saw only when the cutting plane is aligned with the target plane. This increases the safety of the system.

Figure 20:
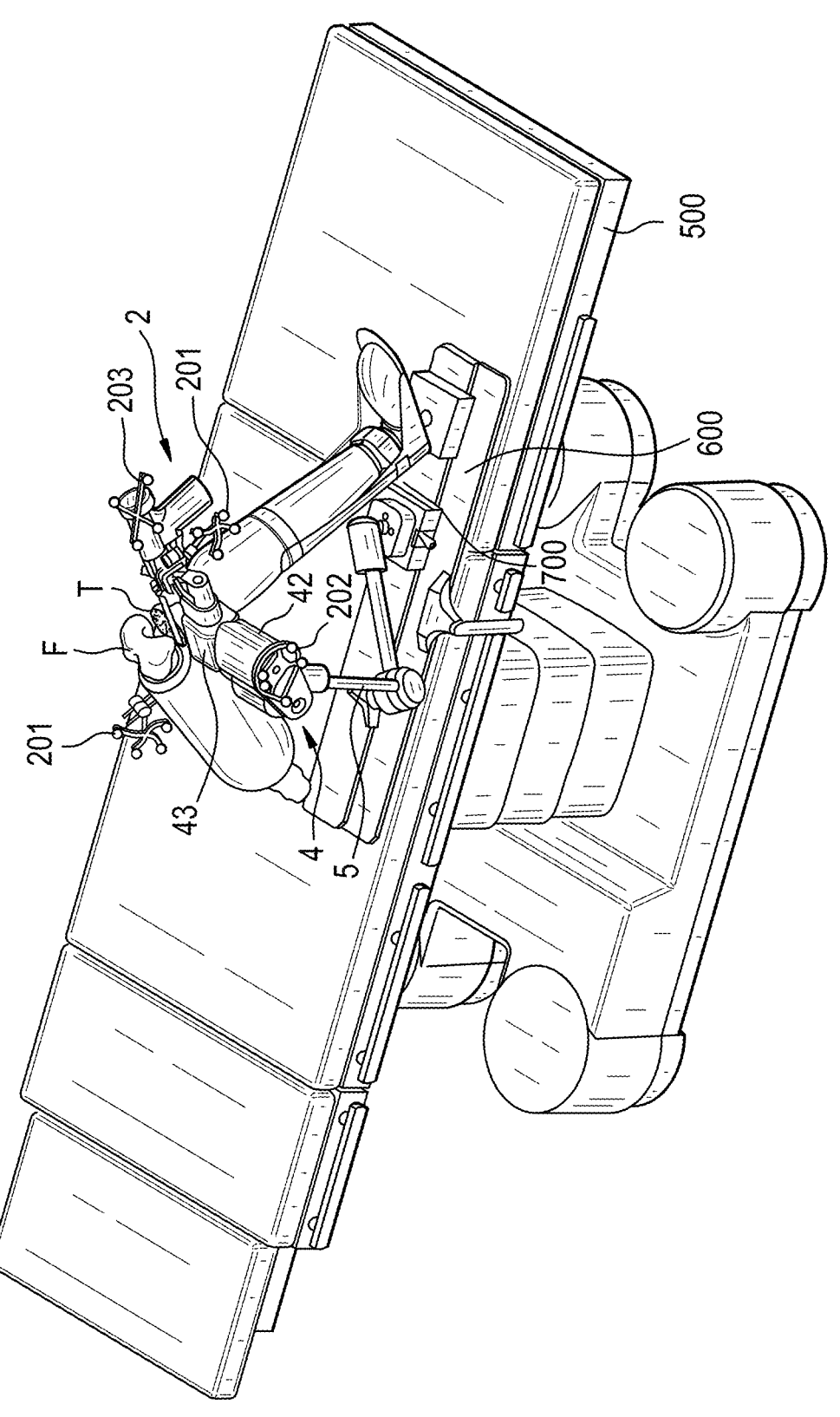
FIG. 20 shows a setup of the robotic device according to an embodiment.

FIG. 20 shows an embodiment of a setup of the robotic device illustrated in FIGS. 3-3B.

The patient (only one flexed leg is represented in FIG. 20) is lying on an operating table 500, with the lower leg supported by a leg holder 600. A tracker 201 is fixed to the femur and another tracker 201 is fixed to the tibia.

The holding arm 5 has one end attached to the leg holder 600 and the opposite end attached to the actuation unit 4.

The holding arm can be freely manipulated by the user so as to bring the robotic device in the desired position relative to the patient, and bears the weight of the robot. The arm 5 can be locked once the desired position has been achieved. The holding arm may be one of the arms described with reference to FIGS. 9 and 10.

In this setup, the robotic device does not comprise any support unit. However, a support unit could be provided (in addition to the holding arm) without departing from the scope of the invention.

A tracker 202 is fixed to the second segment of the actuation unit 4 of the robotic device.

The saw 2 is connected to the third segment by a passive planar mechanism 24.

A tracker 203 is also attached to the saw 2, which allows compensating mechanical play that may exist between the robotic device and the saw.

Figure 21:
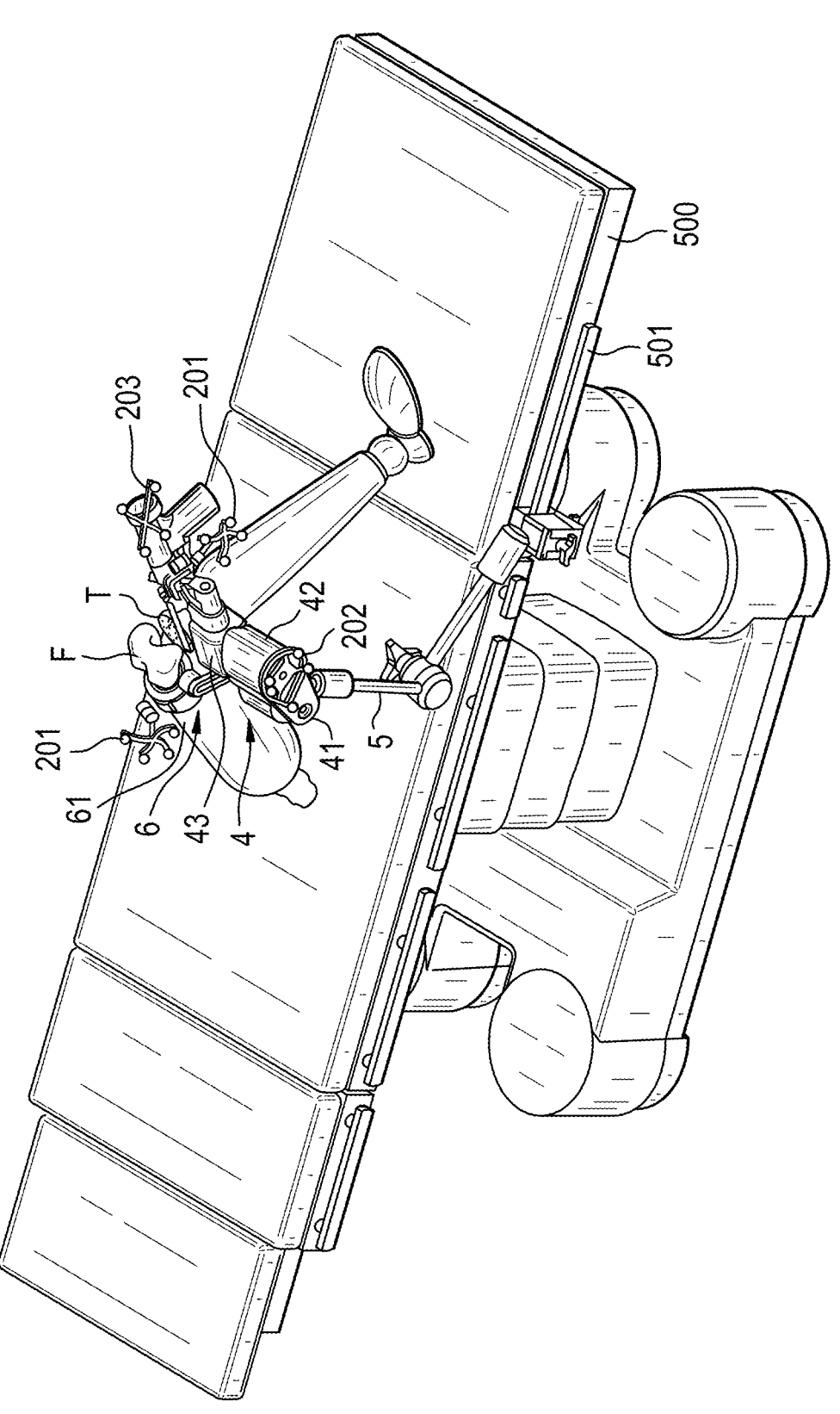
FIG. 21 shows a setup of the robotic device according to another embodiment.

FIG. 21 shows another embodiment of a setup of the robotic device illustrated in FIGS. 3A-3B.

The patient (only one leg is represented in FIG. 21) is lying on an operating table 500, with the leg in flexed position. Although not illustrated, the patient's leg can be maintained in said flexed position by wedges commonly used in surgical interventions. For example, one wedge can be placed under the foot and another one can be placed on the external side of the hip, in order to reduce inward and outward movements of the flexed leg.

A tracker 201 is fixed to the femur and another tracker 201 is fixed to the tibia.

The holding arm 5 has one end attached to a rail 501 arranged on the operating table 500 and the opposite end attached to the actuation unit 4. The rail to which the holding arm is attached may be the rail located on the same side of the table as the leg of interest, or the rail located on the side of the table opposite to the leg of interest.

The actuation unit is also attached to a strap 61 arranged around the upper leg, which provides a support unit 6 creating a partial mechanical link between the anatomical structure and the actuation unit 4. Due to the fact that the support unit makes either direct contact with the anatomical structure to be cut or indirect contact via a region of the patient's body adjacent to the anatomical structure to be cut (here, the soft tissues surrounding the femur), the support unit has the effect of a partial mechanical link that limits the movements of the user when operating the device—and, in advantageous embodiments, also damps movements of the user and/or the patient, vibrations of the cutting tool and reaction forces caused by movements of the actuation unit.

A tracker 202 is fixed to the second segment of the actuation unit 4 of the robotic device.

The saw 2 is connected to the third segment of the actuation unit 4 by a passive planar mechanism 24.

A tracker 203 is also attached to the saw 2, which allows compensating mechanical play that may exist between the robotic device and the saw.

Figure 22:
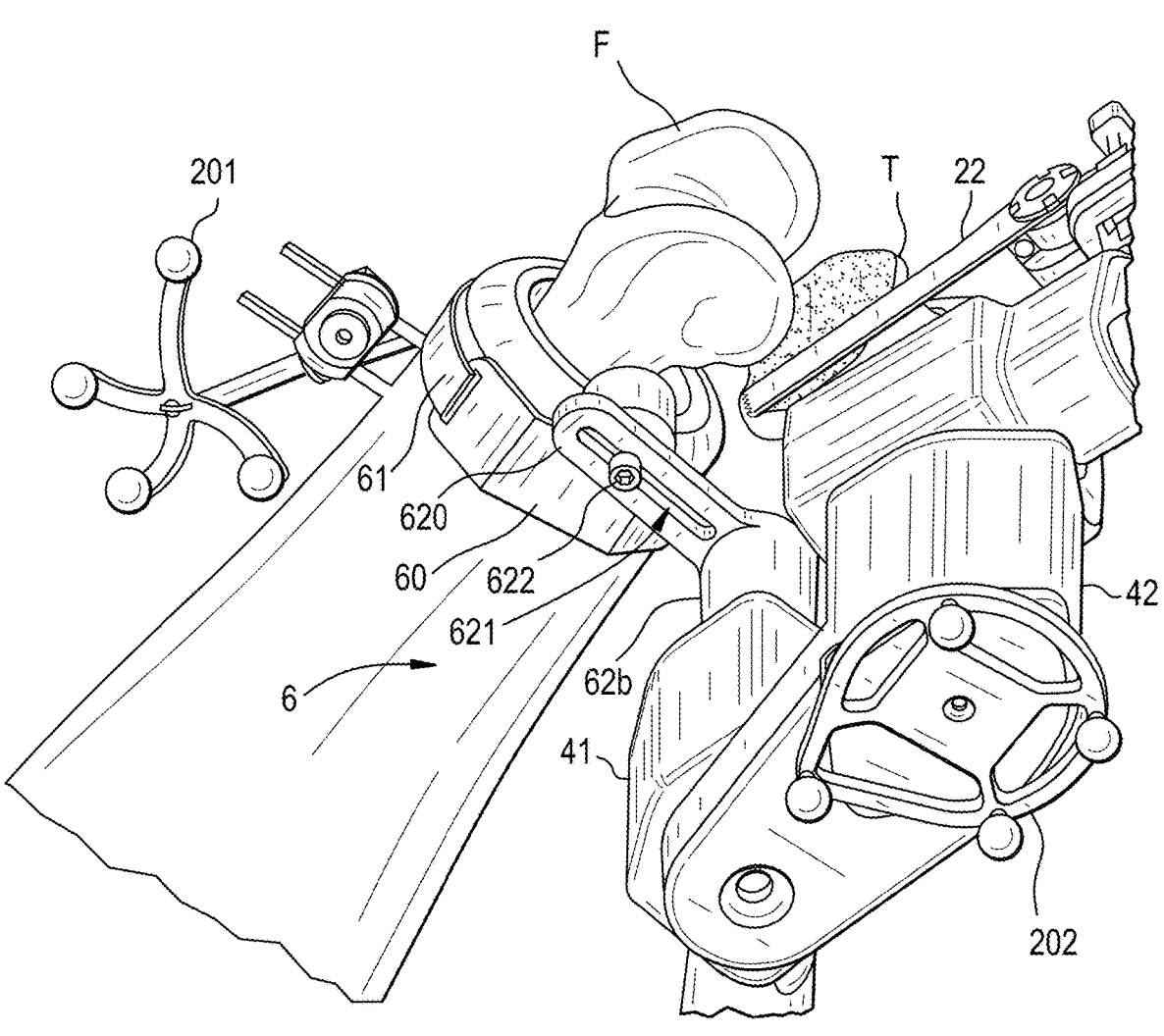
FIG. 22 shows a setup of the robotic device according to another embodiment.

FIG. 22 shows another embodiment of a setup of the robotic device illustrated in FIGS. 3A-3B.

The patient (only one flexed leg is represented in FIG. 22) is lying on an operating table 500, with the lower leg supported by a leg holder 600. A tracker 201 is fixed to the femur and another tracker 201 is fixed to the tibia.

The holding arm 5 has one end attached to the leg holder 600 and the opposite end attached to the actuation unit.

As in the embodiment of FIG. 21, the actuation unit 4 is also attached to a strap arranged around the upper leg, which provides a support unit 6 creating a partial mechanical link between the anatomical structure and the actuation unit.

Figure 23:
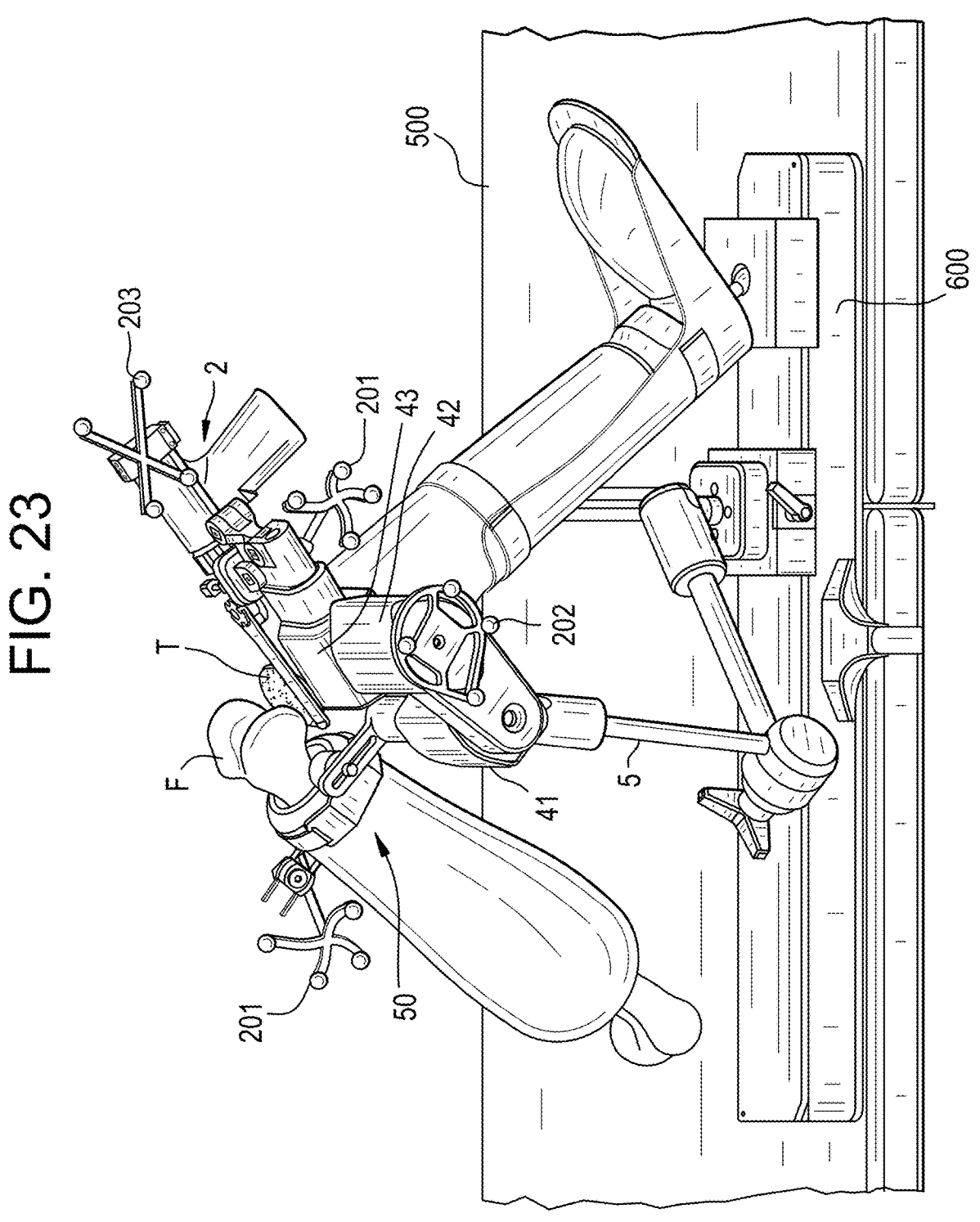
FIG. 23 is an enlarged view of FIG. 21 or 22, showing an embodiment of the support unit.

FIG. 23 is an enlarged view of FIG. 21 or 22 to better show the support unit.

The support unit 6 comprises a flexible strap 61 and a rigid support 60 that together enwrap the soft tissues around the patient's femur F. The flexible strap 61 allows tightening the rigid support 60 to the leg, the tension of the flexible strap being adjusted depending on the diameter of the patient's leg. Cushions of different thicknesses can be inserted between the rigid support and the patient's skin to adapt to various sizes of the leg. It is also possible to use a spring mechanism to exert a pressure on the side of the rigid support, which provides a variable adjustment to individual patients. Finally, a mechanical system 62 enabling to take away the rigid support 60 of the support unit from the actuation unit 4 can be used. The distance can be set by the means of discrete positions or by a clamping mechanism.

In any embodiment, the support unit attached to the thigh can be used for performing the cuts on the tibia bone since the tibia and femur are linked by soft tissues creating a mechanical link that stabilizes the motions. In another embodiment, the support unit can be attached to the lower part of the leg (tibia) and the actuation unit is used to perform all cuts on the femur and tibia bone.

A base 62b of the support unit is attached to the first segment 41 of the actuation unit 4 (which is also rigidly attached to the holding arm), so as to freely rotate around the first axis.

The base 62b comprises a radially extending member 620 provided with a central groove 621.

The base 62b is connected to the strap support 622 by a screw slidably engaging the central groove 621. The distance between the actuation unit and the leg can be adjusted by moving the base 62b relative to the screw 622. Once the desired distance has been obtained, the screw 622 is tightened so as to rigidly connect the base to the strap support 60. According to other embodiments illustrated in FIGS. 11-12, it is also possible to use a radially extending member without such a screw and groove for adjustment, providing a fixed distance between the actuation unit and the leg, and only connected to the actuation unit, the holding arm or the intermediate part by a pivot link. It is also possible to eliminate the movements and adjustments of the support unit using a fixed element relative to the base of the actuation unit.

FIG. 23 shows only one example of the support unit and the skilled person may design the support unit to include a greater number of settings (translational and/or rotational) to adjust the position of the robotic device relative to the leg.

Although the support unit is represented around the femur in FIGS. 21, 22 and 23, it could be attached to the tibia, or to both the femur and the tibia.

Figure 24A:
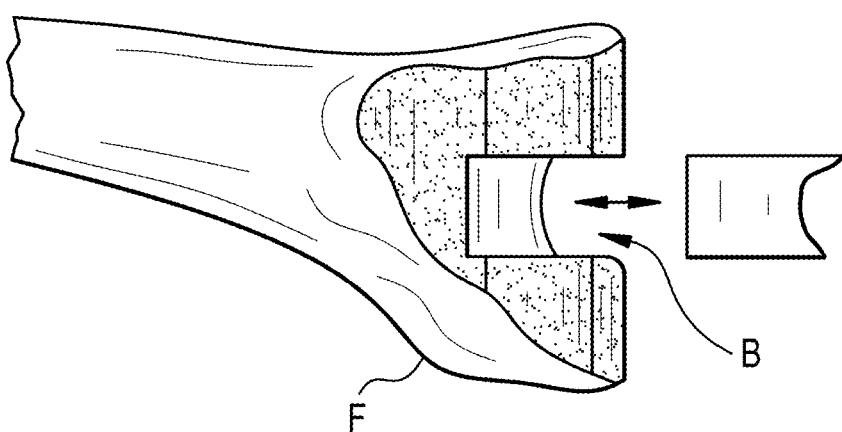
FIGS. 24A-24C illustrate an application of the robotic device to perform vertical cuts.
Figure 24B:
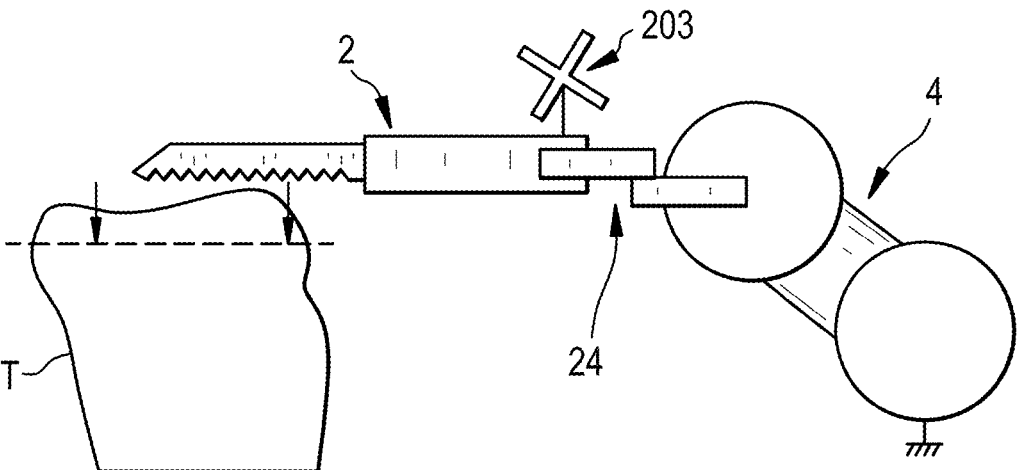
Figure 24C:
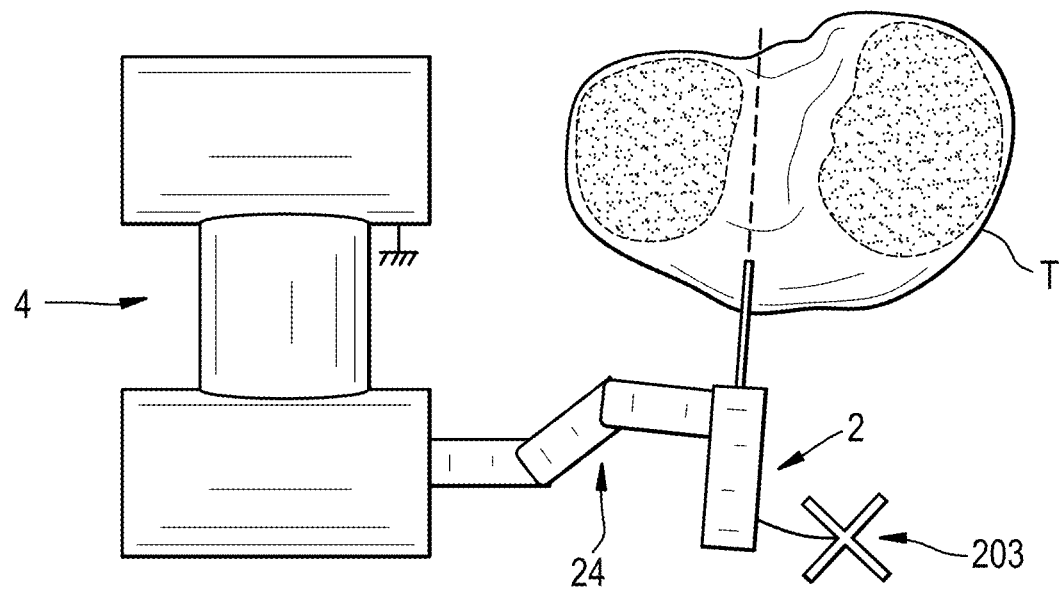

FIGS. 24A to 24C illustrate another application of the robotic device. In this embodiment, the cutting tool is a reciprocating saw orthogonal to the plane of the planar mechanism.

This saw may be used to perform so-called vertical or sagittal cuts. In particular, during a TKA surgery, these vertical cuts allow forming in the femur a box B configured to receive a postero-stabilized (PS) femoral component (see FIG. 24A). During UKA surgery, the reciprocating saw can be used to perform the sagittal cut necessary to install the tibial implant.

Before starting the cut, the first step is to align the planar mechanism 24 with a plane orthogonal to the cut (e.g. the sagittal cut on the tibia, see FIG. 24B). The actuation unit 4 constrains the planar mechanism 24 inside a given plane above or below the bone material to be cut.

If the planar mechanism is active (fully motorized), the saw can then be positioned by the system automatically/actively.

Otherwise, if the planar mechanism is partially active (with a combination of motorized and non-motorized degrees of freedom) or fully passive, the saw 2 must be localized in 3D thanks to a tracker 203. An interface showing the saw position and orientation relative to the bone and to the target plane is displayed to assist the surgeon. Then the surgeon can move the saw 2 until it reaches a target position and orientation (which is a line (hereinafter called "target line", represented by a dotted line) when considered in the plane orthogonal to the target plane) (see FIG. 24C).

Another option, if the planar mechanism is partially or fully active, or equipped with a position locking mechanism, is to let the surgeon displace the reciprocating saw to the right position, and then lock or constrain the saw blade to remain inside the target line once it has been reached.

Then, the cut can be performed, moving the reciprocating saw up or down.

According to a first option, the actuation unit displaces the saw actively, by regularly changing the planar mechanism plane (lowering or raising it). The cutting action of the saw must be enabled during this process so that the cut can be realized while the actuation unit actually moves. In a preferred embodiment, the cutting action of the saw is switched on or off by the control unit of the system. If the planar mechanism is not fully active, the surgeon may have to maintain the saw blade in the right orientation during the cut. At any time, if the planar mechanism orientation or position deviates from the target line more than a predetermined threshold (e.g. 2 degrees or 2 mm), the actuation unit will stop lowering or raising the planar mechanism plane. Additionally, for the sake of safety, the displacement of the planar mechanism plane should only be possible if the surgeon maintains the cutting action enabled, e.g. using a foot switch and/or a trigger pressed. As soon as the foot switch or trigger is released, the actuation unit will stop lowering or raising the planar mechanism plane. Optionally, the speed of displacement of the planar mechanism plane may be modified during the cut based on its level of advancement. For instance: the speed may be low at the beginning to avoid slipping or other causes of a loss of alignment due to the initial contact between the saw blade and the bone surface; then the actuation unit can move faster in the middle of the cut; and eventually it can progressively slow down to zero until the cutting limit (e.g. the tibial cut plane) is reached, with various predefined speed profiles.

According to another option, the surgeon pushes up or down on the saw to perform the cut. The robotic device detects the direction and strength of the force applied by the surgeon and the actuation unit shifts the planar mechanism plane accordingly (maintaining its orientation so that it always remains orthogonal to the target plane). If the blade reaches a limit (for instance the planned or already performed transverse tibial cut in case of UKA), then the actuation unit does not move anymore, preventing the saw from being lowered or raised anymore, so that the surgeon feels that the limit has been reached. In the same spirit as the previous section, the counter-force applied by the actuation unit may vary depending on the level of advancement of the cutting process.

By default, it is assumed in the above description that the reciprocating saw is rigidly fastened to the planar mechanism. However, it would be possible to only use a partial mechanical link (for instance the saw could even only rest on the planar mechanism, maybe with a simple interface with complementary features to prevent unwanted translation between the saw and the planar mechanism). This way the planar mechanism will mainly serve as a guard to prevent the saw from cutting too low or too high. It can also partially guide the saw as it is displaced orthogonally to the sagittal cut. Moreover, to prevent wrong cuts, the actuation unit may move only if the saw position and orientation is maintained within a predefined range (e.g. 2 mm and 2 degrees) relatively to the target line.

Figure 25:
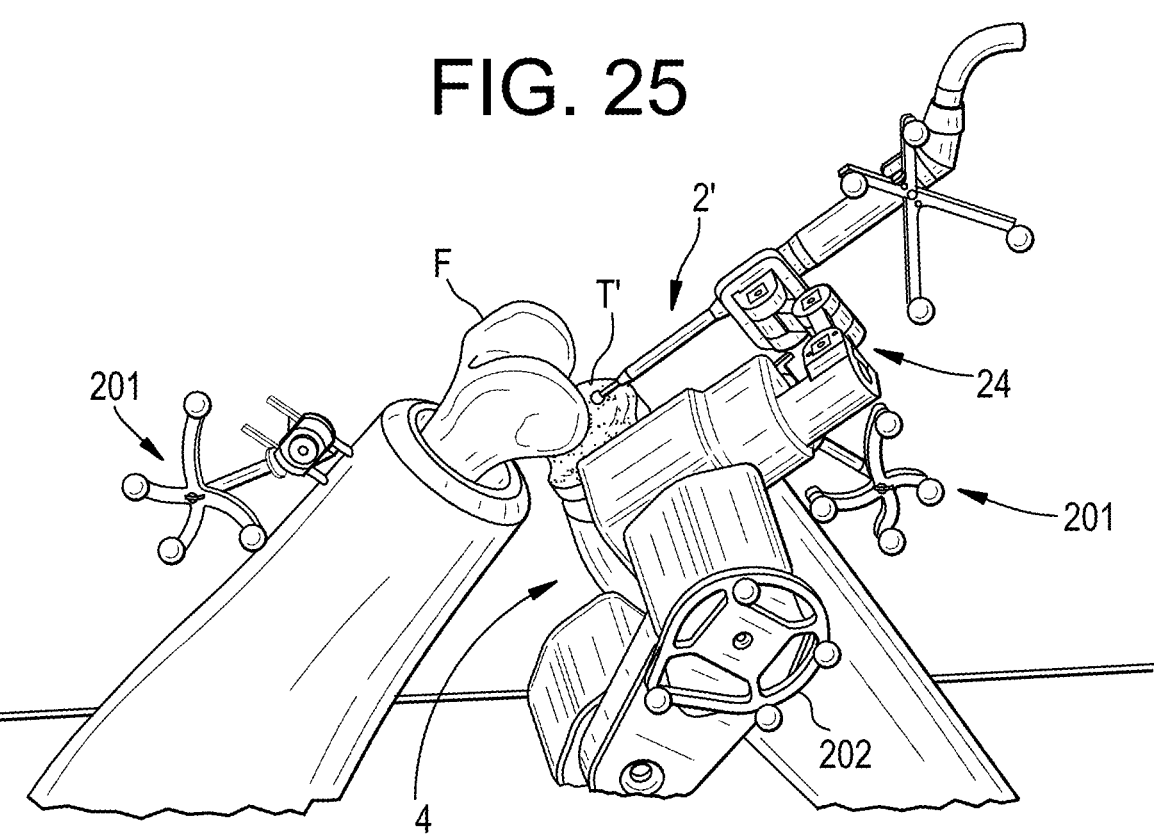
FIG. 25 illustrates an embodiment of the robotic device wherein the cutting tool is a burr.

FIG. 25 illustrates a setup of the robotic device illustrated in FIGS. 3A-3B, with a burr 2' as the cutting tool.

Although the trackers illustrated in the figures are optical trackers, it should be noted that any other tracking technology (e.g. electromagnetic) may be used.

It should be noted that the embodiments described above may be combined.

In addition, the holding arm—and, if any, the support unit which only provides a partial mechanical link—does not require any invasive action onto the patient while fully supporting the weight of the robotic device.

Thus, as compared to the large screws and pins that are implanted in the bone (i.e. that penetrate the bone on several centimeters) in document US 2011/0130761, the robotic device described herein is not fixed directly to the patient but held by the holding arm which is attached to a component (operating table, leg holder . . . ) non-invasively fixed to the patient, and may only be coupled directly to the patient by non-invasive attachment means (e.g. a strap, etc.).

Micro or macro motions of the robotic device with respect to the anatomical structure to be cut, including slow and fast motions, are compensated within a tolerance range and a given time frame that defines the precision of the device.

Typically, for bone surgery applications, motions in the range of a few tenths of a millimeter need to be compensated to obtain sufficient precision; such a compensation requires ultrafast motion detection and measurement, as well as calculation of the compensation motion to be applied and execution of the desired compensation motion.

Large surgical robots with six degrees of freedom are very stiff but are very cumbersome and expensive; besides, they have a considerable inertia (especially on the first mobile segment), which is not compatible with real time control of the cutting plane. On the other hand, existing small, lightweight robots cannot be used if they are not rigidly attached to the anatomical structure. By contrast, the present disclosure provides a compact, lightweight robotic device that allows real time control of the cutting plane without requiring any invasive fixation to the patient.

Figure 27:
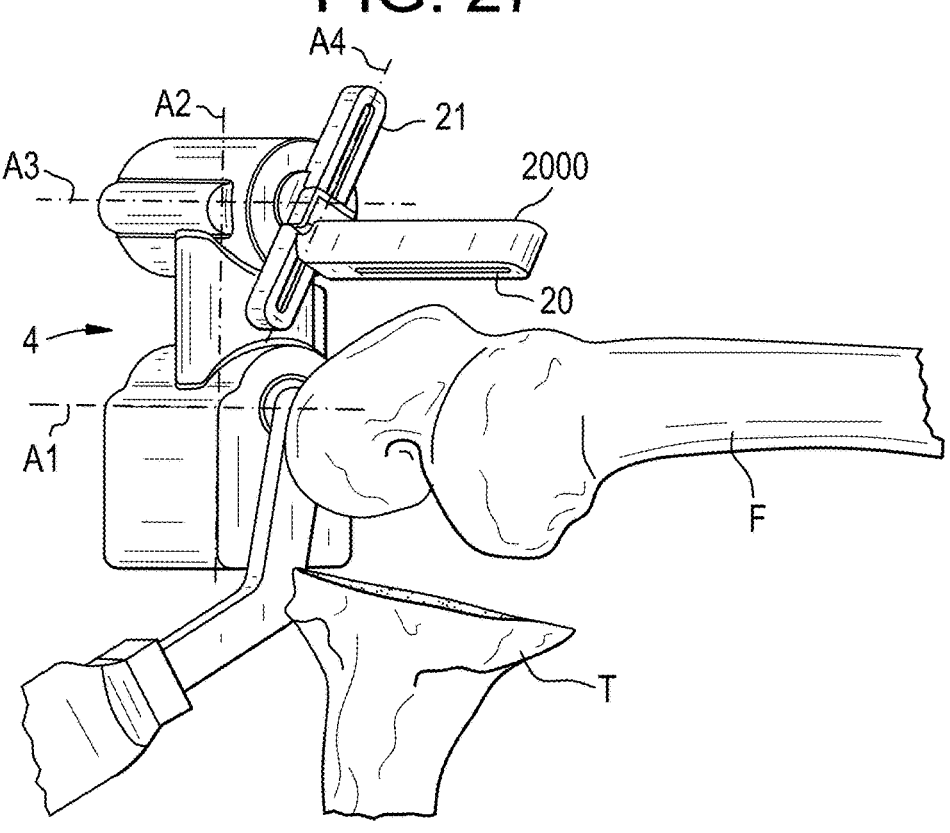
FIG. 27 shows an embodiment of the device wherein the cutting block is mounted on a slider intended to adjust the distance between the cutting block and the bone to be cut.

Although the previous description has been made with reference to a cutting tool mounted on an end effector that is attached to the actuation unit, embodiments comprise a cutting block mounted on the end effector which is itself attached to the actuation unit, e.g. via the planar mechanism described above or via a slider (see FIG. 27). The cutting block comprises at least one slot that defines a guiding plane which corresponds to the cutting plane of the cutting tool. Each slot allows constraining a cutting tool held in a user's hand in the respective guiding plane. This cutting tool can be a sagittal saw, a reciprocating saw, or even a burr as described above.

Figure 28A:
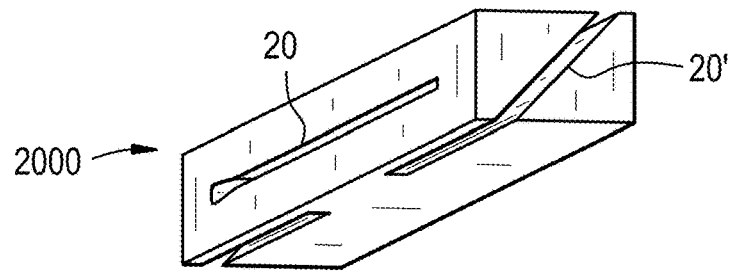
FIGS. 28A-28B show perspective views of a cutting block comprising respectively two and three slots for insertion of a cutting tool.
Figure 28B:
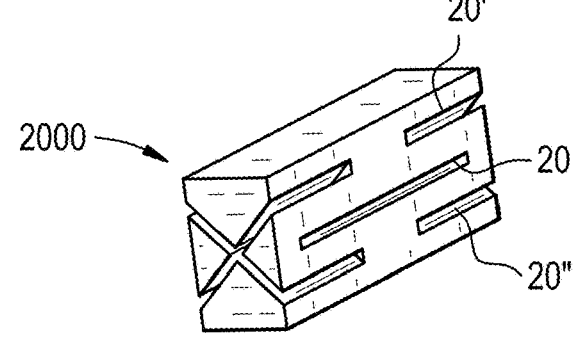
Figure 29A:
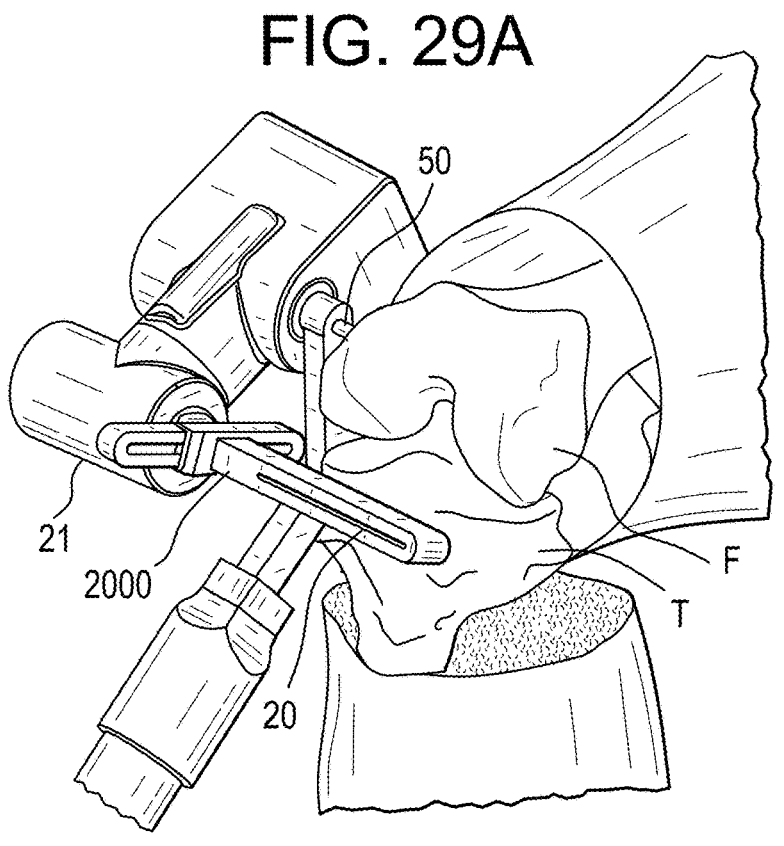
FIGS. 29A-29F show perspective views of the robotic device with the cutting block positioned to cut the tibia and to carry out the femur distal cut, the anterior cut, the posterior cut, the anterior chamfer and the posterior chamfer cuts, respectively.
Figure 29B:
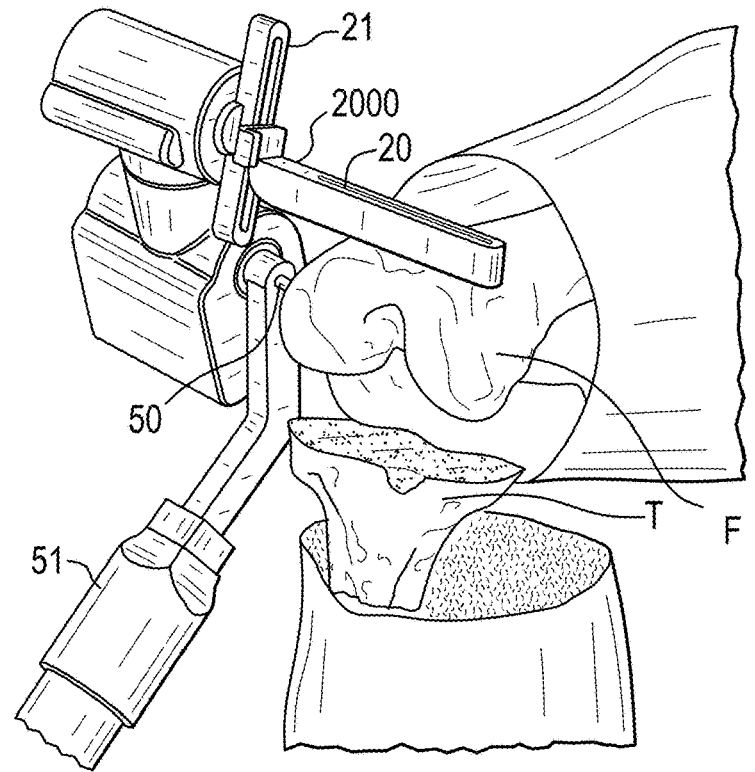
Figure 29C:
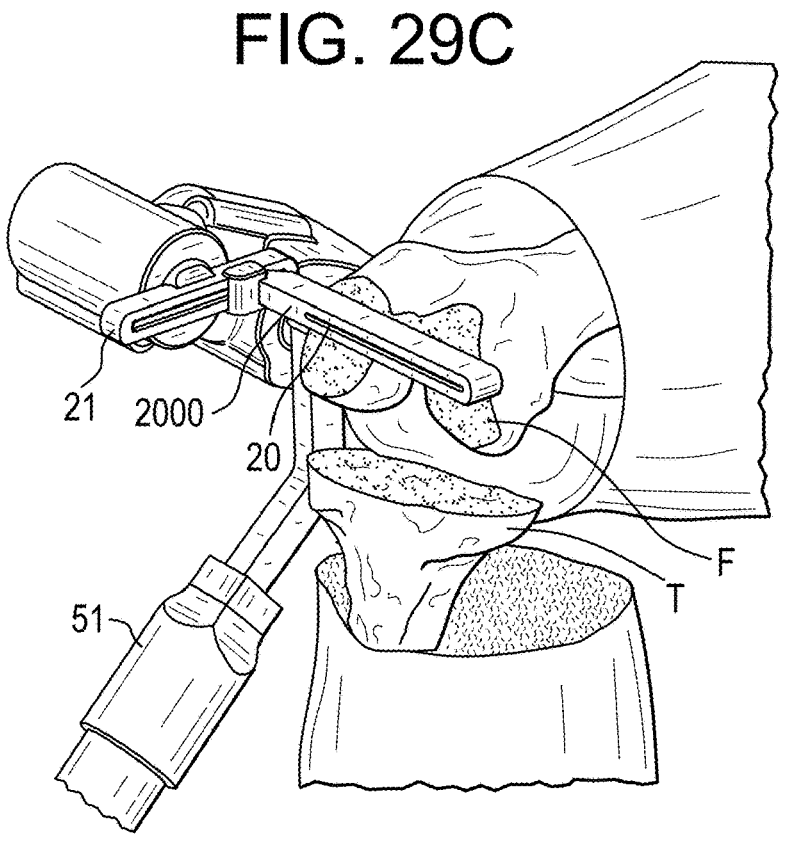
Figure 29D:
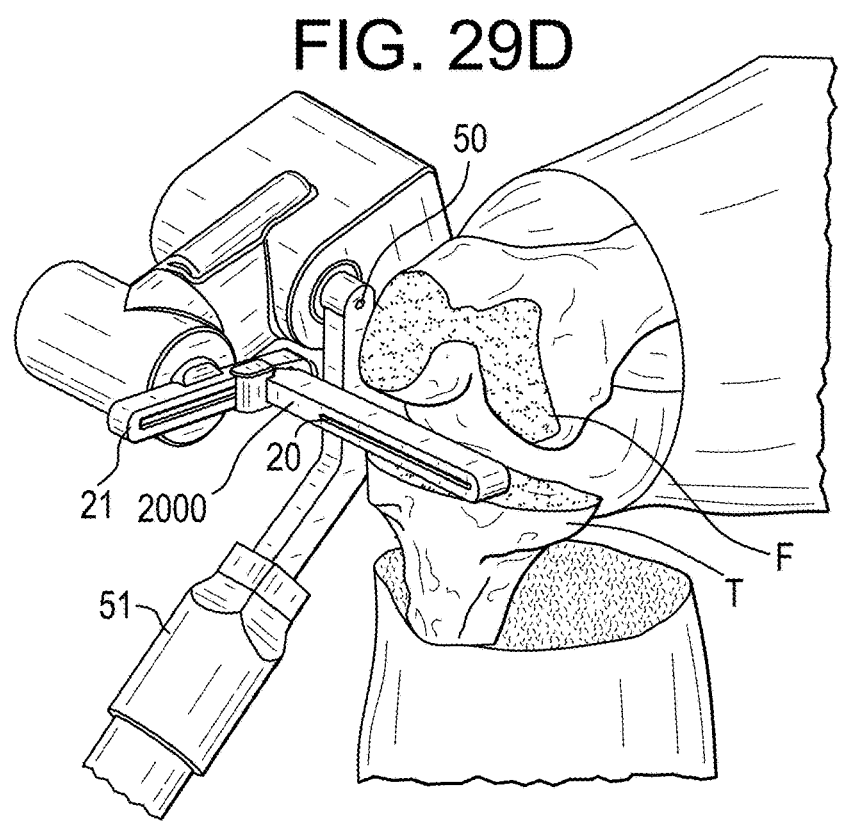
Figures 29E, 29F:
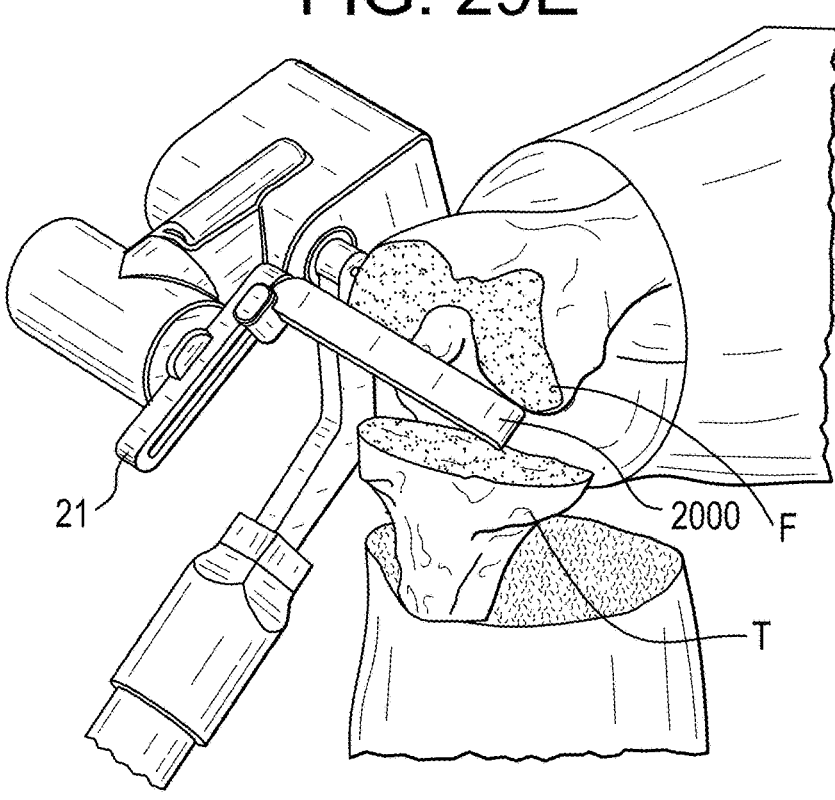

According to particular embodiments, the cutting block 2000 may comprise two slots 20, 20' (see FIG. 28A) or three slots 20, 20', 20'' (see FIG. 28B). Thus, once the cutting block has been positioned with one slot in alignment with a target plane, only a slight adjustment of the pose of the cutting block is necessary to align another slot with another target plane. The slots may even be arranged in a given relative position such that, once one slot has been placed in alignment with a target plane, at least one other slot is also aligned with another target plane. In this way, it is possible to carry out several cuts without moving the cutting block and the robotic device.

In order to provide an optimal guidance of the saw blade and avoid any deviation of the saw blade, the width w of the slot is as large as possible. For example but not limited to, the width of the slot may range from 10 to 25 mm.

Figure 30:
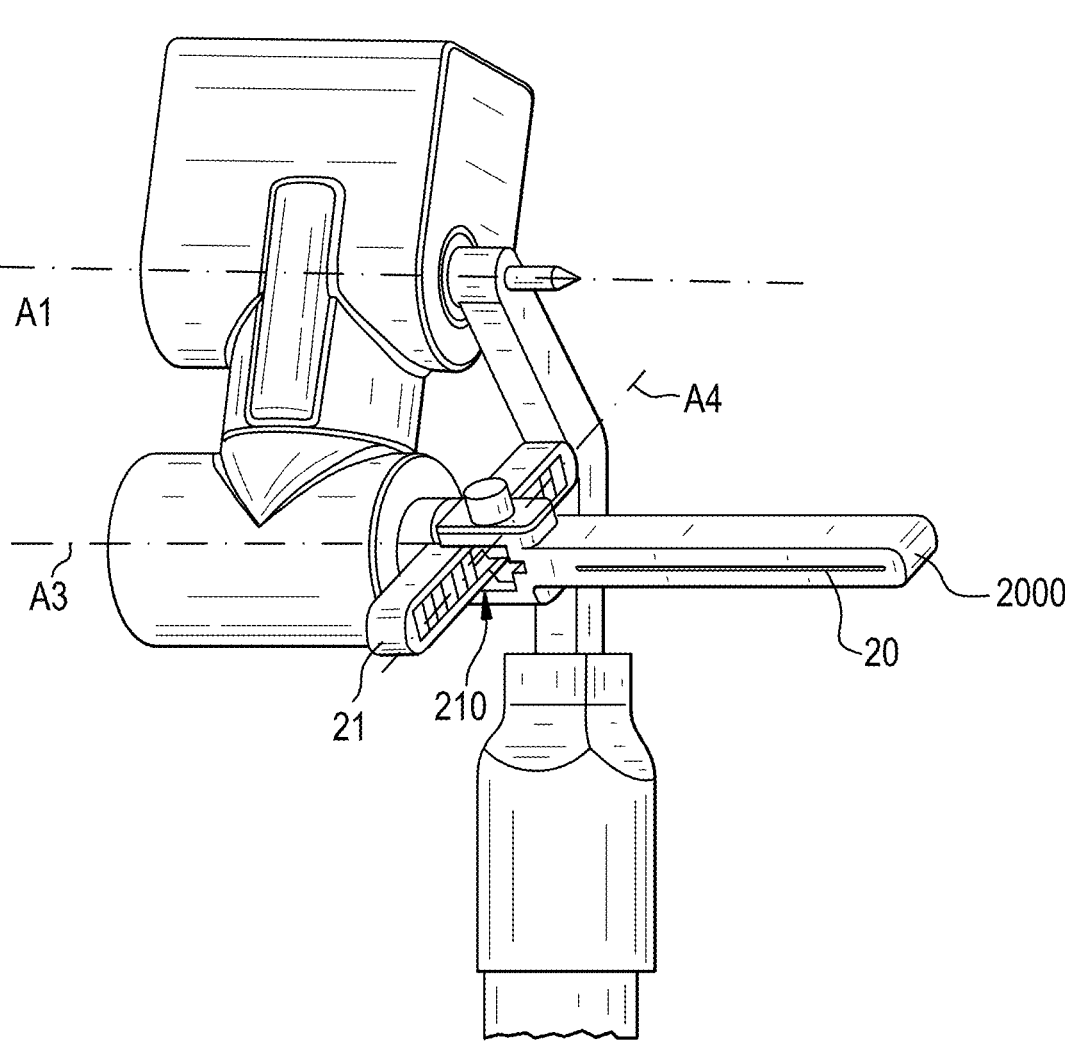
FIG. 30 shows an embodiment of the device wherein the slider onto which the cutting block is mounted comprises a plurality of determined positions provided by a rack and pinion mechanism.

The planar mechanism or the slider provides an additional degree of freedom in translation along an axis A4 which is parallel to the plane defined by the slot 20 (see FIGS. 29A-29F and 27). Such a slider allows maintaining the distance between the rotation axes of the actuation unit to a small distance, the additional translation along the slider providing access of the cutting block to farther regions of the anatomical structure. According to an embodiment, the slider is manually operated. As shown in FIG. 30, the slider may be provided with a rack and pinion mechanism 210 in order to provide a plurality of determined positions. According to an embodiment, the slider may be biased by an elastic member such as a spring (not shown). According to an embodiment, the slider may be motorized, thus providing a fourth motorized degree of freedom controlled by the control unit, within the target plane. Once the position of the cutting block has been adjusted, the slider may be blocked to avoid any further movement of the cutting block.

The planar mechanism may further allow pivoting the cutting block around a fifth axis A5 which is substantially orthogonal to the plane defined by the slot 20. This enables placing the cutting block closer to the bone without changing the orientation of the guiding plane. This rotational degree of freedom of the cutting block can also be combined with the translational degree of freedom provided by the above-mentioned slider.

In some embodiments, the support unit may be arranged between the cutting block and the patient.

For example, as shown in FIG. 31A, the cutting block 2000 comprises at least one flexible interface (e.g. one or more silicone cushions 56) configured to contact the anatomical structure. In this way, the cutting block may be pressed against the anatomical structure (e.g. using a slider as described above), thus ensuring a partial mechanical link. The pressure can be applied against the holding arm 5 in combination with a leg holder that holds the knee substantially still. However, it is still possible to slide by a few degrees or millimeters the flexible interface along the anatomical structure to adjust its position. In this embodiment, the actuation unit is connected to the anatomical structure via the cutting block 2000 and the support unit is made of the silicone cushion(s) 56. According to a preferred embodiment, the flexible interface comprises two silicone cushions disposed on both sides of the slot 20 of the cutting block, with a sufficient distance between both cushions so as to avoid damaging them when cutting with the saw. Instead of silicone, any soft biocompatible material can be used.

According to another embodiment (not shown), the cutting block may comprise an interface made of a plurality of sharp teeth. In this way, the cutting block may be pressed and retained against the anatomical structure by the teeth, thus ensuring a partial mechanical link.

According to another embodiment, the cutting block may be fixed to the anatomical structure by small pins 57 (see FIG. 31B). Said pins can be drilled and removed automatically using dedicated motors controlled by the control unit.

The tracking unit may comprise a tracker attached to the cutting block or to the cutting tool.

Such a cutting block may in particular enable cutting the lateral walls of a box within the anatomical structure in order to create a notch. This is necessary to position femoral implants that are postero-stabilized and include a box in their design which necessitates to create a notch in the bone for perfect fitting.

Figure 32:
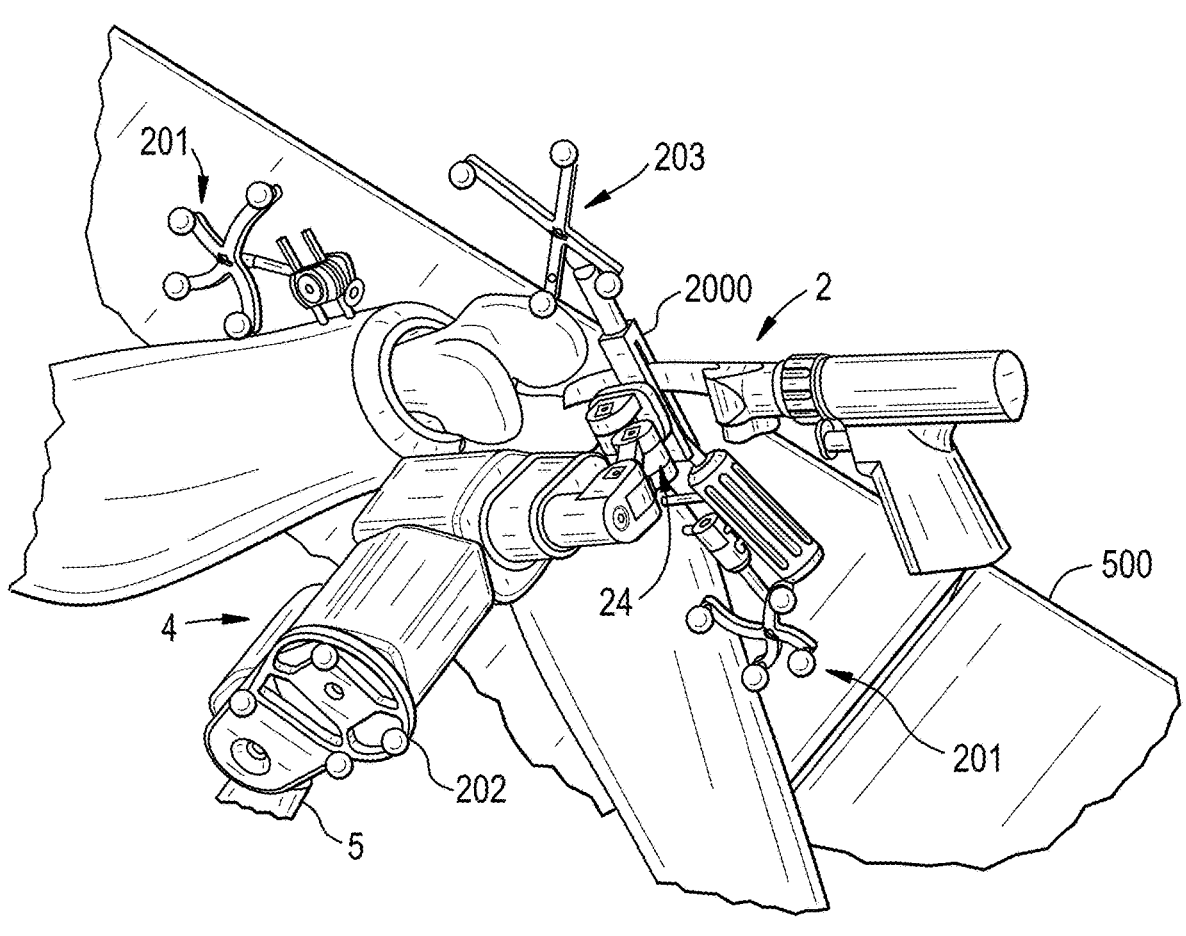
FIG. 32 illustrates a setup of the robotic device with a cutting block.

FIG. 32 illustrates a setup of the robotic device in such a situation.

The patient (only one flexed leg is represented in FIG. 32) is lying on an operating table 500. A tracker 201 is fixed to the femur and another tracker 201 is fixed to the tibia.

The holding arm 5 has one end attached to the table and the opposite end attached to the actuation unit.

In this setup, the robotic device does not comprise any support unit. However, a support unit could be provided, in addition to the holding arm 5.

A tracker 202 is fixed to the second segment of the actuation unit of the robotic device.

The cutting block 2000 is connected to the third segment of the actuation unit 4 by a passive planar mechanism 24.

A tracker 203 is also attached to the cutting block, which allows compensating mechanical play that may exist between the robotic device and the cutting block.

The cutting tool is a reciprocating saw 2 whose blade passes through the slot of the cutting block 2000.

Operation of the control unit will be described in more detail below.

Figure 33:
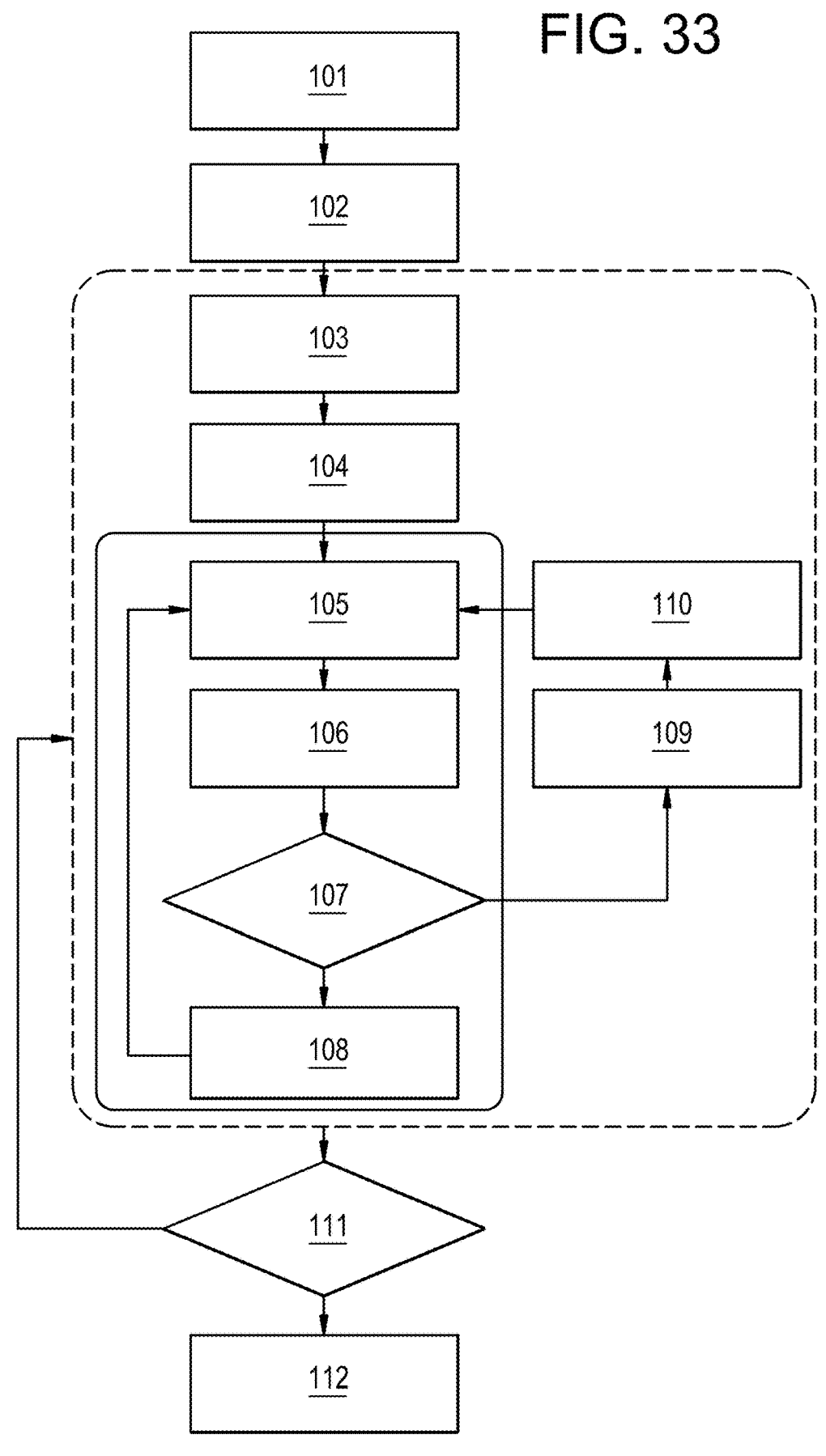
FIG. 33 is a flowchart of a surgical procedure for performing at least one osteotomy implementing an embodiment described herein.

FIG. 33 is a flowchart of a complete surgical intervention intended to implement at least one osteotomy, such as total knee arthroplasty. It is to be noted that the initial and final steps may not form part of the claimed invention.

In step 101, the patient's anatomy in the region to be treated by the surgical intervention is acquired. Said acquisition may be made, in a manner known per se, for example using imaging means for acquiring an image of the bones and/or a localized pointer (digitization probe) for acquiring a plurality of points of the bone surfaces as it is commonly used in image-free surgical navigation techniques.

In step 102, a surgical planning is carried out based on the acquired patient's anatomy. This planning step results in the definition of the pose of target planes intended to carry out the cuts.

In step 103, a user positions the robotic device with the holding arm in a rough position intended to allow performing the cuts according to the target planes. In this step, the patient's anatomy is also equipped with at least one tracker. The robotic device and the end effector are also equipped with at least one tracker, so as to enable localizing the relative positions of the robotic device, end effector and anatomical structure to be cut. In this step, especially if several cuts are to be made without repositioning the robotic device, the user may use the user interface to determine a suitable position and orientation of the robotic device.

In step 104, the order of the cuts to be carried out is selected. To that end, the control unit retrieves the pose of the corresponding target plane. If several cuts are to be performed, they may be memorized in the system in a specific order, and loaded one after the other. Otherwise, the user interface may allow the user to select a specific cut. It is to be noted that this step may be carried out at any time before step 105.

In step 105, the control unit receives the tracking data of the trackers. Thus, the control unit is able to compute the current positions of the robotic device and end effector relative to the anatomical structure to be cut.

Based on the current position of the robotic device, the end effector, the pose of the target plane and the kinematic design of the robotic device, the control computes in step 106 a movement of the actuation unit allowing reaching the target plane. In step 107, the control unit checks whether the target plane is reachable by the robotic device in its current position (i.e. without moving the support unit). If so, the control unit commands the actuation unit to move the cutting tool or the cutting guide to the required position so as to have the cutting plane in alignment with the target plane (step 108).

If the current position of the robotic device does not allow achieving alignment on the target plane, the control unit warns the user that he cannot and must not perform the cut (step 109) and computes in step 110 a new position of the robotic device to reach the target plane (said new position implying moving the holder unit), and steps 105 to 107 are carried out again.

In step 108, once the cutting plane has been aligned with the target plane, the cut is allowed by the control unit (e.g. by providing an indication to the user that the cutting plane is aligned with the target plane, and/or by allowing the start of actuation of the cutting tool by the user). The user can perform the cut by operating a cutting tool within the cutting plane. During this cutting step, the control unit uses the tracking data to check whether the cutting plane remains aligned with the target plane (see the loop between steps 105 and 108).

Once the cut has been completed (after step 108), the user indicates to the control unit that the cut is finished. Said indication can be made for example by pressing a footswitch or a button.

In step 111, the user or the control unit checks whether there remain any cuts to be carried out.

If not, postoperative checks may be carried out in step 112.

If cuts remain to be carried out, steps 105-108 (and, if appropriate, 109 and 110) are iterated until all the planned cuts have been carried out.

The invention claimed is:

1. A surgical system, comprising:

an end effector operably attached to the holding arm, the end effector for holding or guiding a cutting tool for cutting a bone of a patient, wherein a pose of the end effector defines a cutting plane;

a robotic device connected to the end effector to adjust the pose of the end effector, and therefore, adjust the cutting plane;

a first tracker attached to the robotic device, a second tracker attached to the end effector, and a third tracker attached to the patient; and a control unit configured to:

receive a planned target plane for cutting the bone;

determine the pose of the end effector and a pose of the patient;

determine whether a pose of the robotic device can be determined, and, if the pose of the robotic device can be determined, storing the determined pose of the robotic device, and, if the pose of the robotic device cannot be determined, retrieving a previously stored pose of the robotic device;

determine a deviation between the cutting plane and the target plane, wherein:

if the deviation is less than a threshold, allow operation of the cutting tool; and if the deviation is greater than or equal to the threshold:

determine a movement for the robotic device to align the cutting plane with the target plane;

move the robotic device to adjust the cutting plane;

determine an updated pose of the end effector and therefore an updated cutting plane; and determine an updated deviation between the updated cutting plane and the target plane, and if the updated deviation is less than the threshold, allow operation of the cutting tool.

2. The surgical system of claim 1, wherein the control unit is further configured to, if the pose of the robotic device cannot be determined, and there is no previously stored pose of the robotic device, repeat the determination of the pose of the end effector and the pose of the patient.

3. The surgical system of claim 1, wherein the control unit is further configured to, if the pose of the robotic device cannot be determined, and there is no previously stored pose of the robotic device, output a message to a user.

4. The surgical system of claim 1, wherein the control unit is further configured not to determine the deviation between the cutting plane and the target plane before determining the pose of the end effector.

5. The surgical system of claim 1, further comprising a planar mechanism interposed between the robotic device and the end effector to constrain the end effector within the cutting plane.

6. The surgical system of claim 5, wherein the control unit is further configured to determine the deviation between the cutting plane and the target plane by accounting for at least one of a mechanical backlash or a flexion of the planar mechanism.

7. The surgical system of claim 1, wherein the control unit is further configured to display feedback information to a user.

8. The surgical system of claim 7, wherein the feedback information is an indication of a distance between the cutting plane and the target plane or an indication of an angle between the cutting plane and the target plane.

9. The surgical system of claim 7, wherein the feedback information is an indication that the robotic device or the patient has moved to an extent that the cutting plane cannot be aligned with the target plane.

10. The surgical system of claim 7, wherein the feedback information is an indication to the user to check that the first tracker is in a field of view of a camera for detecting a position of the first tracker.

11. The surgical system of claim 1, wherein a position of the first tracker and a position of the second tracker are determined using an optical camera configured to operate at a frequency at least twice greater than a frequency at which the control unit is configured to implement a control loop.

12. A surgical system, comprising:

a holding arm;

an end effector operably attached to the holding arm, the end effector for holding or guiding a cutting tool for cutting a bone of a patient, wherein a pose of the end effector defines a cutting plane;

a robotic actuation unit interposed between the holding arm and the end effector to adjust the pose of the end effector, and therefore, adjust the cutting plane;

a first tracker attached to the actuation unit, a second tracker attached to the end effector, and a third tracker attached to the patient; and a control unit configured to:

receive a planned target plane for cutting the bone;

determine the pose of the end effector and a pose of the patient;

determine whether a pose of the actuation unit can be determined, and, if the pose of the actuation unit can be determined, storing the determined pose of the actuation unit, and, if the pose of the actuation unit cannot be determined, retrieving a previously stored pose of the actuation unit;

determine a deviation between the cutting plane and the target plane, wherein:

if the deviation is less than a threshold, allowing operation of the cutting tool; and if the deviation is greater than or equal to the threshold:

determine a movement for the actuation unit to align the cutting plane with the target plane;

move the actuation unit to adjust the cutting plane;

determine an updated pose of the end effector and therefore an updated cutting plane; and determine an updated deviation between the updated cutting plane and the target plane, and if the updated deviation is less than the threshold, allow operation of the cutting tool.

13. The surgical system of claim 12, wherein the control unit is further configured to, if the pose of the actuation unit cannot be determined, and there is no previously stored pose of the actuation unit, output a message to a user.

14. The surgical system of claim 12, wherein the control unit is further configured to, if the pose of the actuation unit cannot be determined, and there is no previously stored pose of the actuation unit, repeat the determination of the pose of the end effector and the pose of the patient.

15. The surgical system of claim 12, wherein the control unit is further configured not to determine the deviation between the cutting plane and the target plane before determining the pose of the end effector.

16. The surgical system of claim 12, wherein the control unit is further configured to display feedback information to a user, the feedback information comprising at least one indication of:

a distance between the cutting plane and the target plane;

an angle between the cutting plane and the target plane;

a movement of the holding arm, actuation unit, or the patient has occurred to an extent that the cutting plane cannot be aligned with the target plane; or a reminder to the user to check that the first tracker is in a field of view of a camera for detecting a position of the first tracker.

17. The surgical system of claim 12, further comprising a planar mechanism interposed between the actuation unit and the end effector to constrain the end effector within the cutting plane.

18. The surgical system of claim 17, wherein the control unit is further configured to determine the movement for the actuation unit to align the cutting plane with the target plane by accounting for at least one of a mechanical backlash or a flexion of the planar mechanism.

19. The surgical system of claim 17, further comprising a fourth tracker attached to the planar mechanism, wherein an actual position of the planar mechanism is used when the pose of the end effector is determined.

20. The surgical system of claim 17, wherein the control unit is further configured to dynamically estimate an alignment error between the actuation unit and the end effector and move the planar mechanism to correct the alignment error.

21. A surgical system, comprising:

an end effector operably attached to a holding arm, the end effector for holding or guiding a cutting tool for cutting a bone of a patient, wherein a pose of the end effector defines a cutting plane;

a robotic actuation unit interposed between the holding arm and the end effector to adjust the pose of the end effector, and therefore, adjust the cutting plane;

a first tracker attached to the actuation unit, a second tracker attached to the end effector, and a third tracker attached to the patient; and a control unit configured to:

determine whether a pose of the actuation unit can be determined or whether a previously stored pose of the actuation unit can be retrieved;

determine the pose of the end effector and a pose of the patient; and determine a deviation between the cutting plane and a pose of a planned target plane transferred to or retrieved by the control unit, wherein:

if the deviation is less than a threshold, allowing operation of the cutting tool; and if the deviation is greater than or equal to the threshold:

move the actuation unit to adjust the cutting plane;

determine an updated pose of the end effector and therefore an updated cutting plane; and determine an updated deviation between the updated cutting plane and the target plane, and if the updated deviation is less than the threshold, allow operation of the cutting tool.

22. The surgical system of claim 21, wherein the control unit is further configured to, if the updated deviation is greater than the threshold, stop the actuation unit.

23. The surgical system of claim 22, wherein the control unit is further configured to, if the pose of the actuation unit was the previously stored pose, erase the previously stored pose.

24. The surgical system of claim 22, wherein the control unit is further configured to, if the pose of the actuation unit was determined, output an error message.

* * * * *